United States Patent
Ertle et al.

(10) Patent No.: US 12,226,411 B2
(45) Date of Patent: Feb. 18, 2025

(54) SOLUBLE GUANYLATE CYCLASE ACTIVATORS FOR TREATING PORTAL HYPERTENSION

(71) Applicant: Boehringer Ingelheim International GmbH, Ingelheim am Rhein (DE)

(72) Inventors: Judith Maria Ertle, Ingelheim am Rhein (DE); Jochen Huber, Mittelbiberach (DE); Leo John Seman, Cheshire, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 77 days.

(21) Appl. No.: 18/123,359

(22) Filed: Mar. 20, 2023

(65) Prior Publication Data

US 2023/0293513 A1    Sep. 21, 2023

Related U.S. Application Data

(60) Provisional application No. 63/321,780, filed on Mar. 21, 2022.

(51) Int. Cl.
| | | |
|---|---|---|
| *A61K 31/4709* | (2006.01) | |
| *A61K 31/351* | (2006.01) | |
| *A61P 1/16* | (2006.01) | |

(52) U.S. Cl.
CPC ........ *A61K 31/4709* (2013.01); *A61K 31/351* (2013.01); *A61P 1/16* (2018.01)

(58) Field of Classification Search
None
See application file for complete search history.

(56) References Cited

U.S. PATENT DOCUMENTS

| | | | | |
|---|---|---|---|---|
| 8,906,904 | B2 * | 12/2014 | Brenneman | A61P 13/12 514/211.09 |
| 11,690,848 | B2 * | 7/2023 | Ertle | A61K 31/55 514/229.2 |

FOREIGN PATENT DOCUMENTS

| | | | | |
|---|---|---|---|---|
| WO | 2014039434 | A1 | 3/2014 | |
| WO | 2017200857 | A1 | 11/2017 | |
| WO | WO-2020011804 | A1 * | 1/2020 | ............. A61K 31/44 |

OTHER PUBLICATIONS

Andersen, Karl et al. "The Effects of Aldosterone Synthase Inhibition on Aldosterone and Cortisol in Patients With Hypertension: A Phase II, Randomized, Double-Blind, Placebo-Controlled, Multicenter Study" (2012) The Journal of Clinical Hypertension, vol. 14, No. 9, 580-587.
Chen, Hongxing, et al. "Soluble Guanylate Cyclase Activator BI 685509 Reduces Portal Hypertension and Portosystemic Shunting in a Rat Thioacetamide-Induced Cirrhosis Model" (2022) Hepatology, vol. 76, p. 1190.
Clinical Trials: NCT05161481 "A Study to Test whether Two Different Doses of BI 685509 Help People with Liver Cirrhosis and High Blood Pressure in the Portal Vein (Main Vessel Going to the Liver)" Sponsor: Boehringer Ingelheim, Jan. 12, 2022, 8 pages.
Clinical Trials: NCT05161481 "A Study to Test whether Two Different Doses of BI 685509 Help People with Liver Cirrhosis and High Blood Pressure in the Portal Vein (Main Vessel Going to the Liver)" Sponsor: Boehringer Ingelheim, Retrieved from the internet, https://clinicaltrials.gov/ct2/show/NCT05161481, retrieved on May 31, 2023, 5 pgs.
Clinical Trials: NCT05282121 "A Study to Test whether BI 685509 Alone or in Combination with Empagliflozin Helps People with Liver Cirrhosis Caused by Viral Hepatitis or Non-Alcholic Steatohepatitis who have High Blood Pressure in the Portal Vein (Main Vessel Going to the Liver)," Sponsor: Boehringer Ingelheim, Retrieved from the internet, https://www.clinicaltrials.gov/ct2/show/NCT05282121, May 31, 2023.
D'Amico, G. et al. "Competing Risks and Prognostic Stages of Cirrhosis: a 25 year inception cohort study of 494 patients", (2014) APT Alimentary Pharmacology and Therapeutics, vol. 39, 1180-1193.
Epstein, Murray "Hyperkalemia constitutes a constraint for implementing renin-angiotensin-aldosterone inhibition: the widening gap between mandated treatment guidelines and the real-world clinical arena" (2016) Kidney International Supplements, vol. 6, 20-28.
Ferreira, Joao Pedro, et al. "Empagliflozin and serum potassium in heart failure: an analysis from Emperor-Pooled" (2022) European Heart Journal, vol. 43, 2984-2993.
Ferreira, Joao Pedro, et al. "Interplay of Mineralocorticoid Receptor Antagonists and Empagliflozin in Heart Failure" (2021) Journal of American College of Cardiology, vol. 77, No. 11, 1397-1407.
Garcia-Tsao, Guadalupe et al., "Portal Hypertensive Bleeding in Cirrhosis: Risk Stratification, Diagonis, and Management, 2016 Practice Guidance by the American Association for the Study of Liver Disease" (2017) Hepatology, vol. 65, No. 1, 310-335.
Groszmann, Roberto J. et al. "Beta-Blockers to Prevent Gastroesophageal Varices in Patients with Cirrhosis" (2005), The New England Journal of Medicine, vol. 353, 21, 2254-2261.
Hargovan, Milan et al. "Aldosterone synthase inhibitors in hypertension: current status and future possibilities" (2014) Journal of the Royal Society of Medicine Cardiovascular Disease, 0(0), 1-9.
Herrington, William G. et al. "The potential for improving cardiorenal outcomes by sodium-glucose co-transporter-2 inhibition in people with chronic kidney disease: a rationale for the EMPA-Kidney study" (2018) Clinical Kidney Journal, 749-761.
Hunter, Robert W. et al. "Hyperkalemia: pathophysiology, risk factors and consequences" (2019) Nephrology Dialysis Transplantation, 34, iii2-iii11.
International Search Report and Written Opinion PCT/US2023/015604 mailed on Mar. 20, 2023.

(Continued)

*Primary Examiner* — Zinna Northington Davis
(74) *Attorney, Agent, or Firm* — David L. Kershner

(57) ABSTRACT

The present invention relates to methods for treating patients with compensated cirrhosis, comprising administering to a patient in need thereof a therapeutically effective amount of a soluble guanylate cyclase (sGC) activator, or a pharmaceutically acceptable salt thereof.

13 Claims, 1 Drawing Sheet

(56) References Cited

OTHER PUBLICATIONS

Jones, Amanda K. et al., "Soluble Guanylyl Cyclase Activator BI 685509 Reduces Portal Hypertension and Portosystemic Shunting in a Rat Thioacetamide-Induced Cirrhosis Model" (2023), J. of Pharmacology and Experimental Therapeutics, vol. 25, 36 pgs.

Lancet, "Global, regional, and national age-sex specific all-cause and cause-specific mortality for 240 causes of death, 1990-2013: a systematic analysis for the global burden of Disease study", Europe PMC Founders Group, Lancet, vol. 385, 2015, 117-171.

Mandorfer, Mattias et al., "Changes in Hepatic Venous Pressure Gradient Predict Hepatic Decompensation in Patients Who Achieved Sustained Virologic Response to Interferon-Free Therapy", (2020) Hepatology, vol. 71, No. 3, 1023-1036.

Mandorfer, Mattias, et al., "Hepatic Venous Pressure Gradient Response in Non-Selective Beta-Blocker Treatment, Is it Worth Measuring" (2019) Current Hepatology Reports, vol. 18, 174-186.

Merkel, Carlo et al., "A Placebo-Controlled Clinical Trial of Nadolol in the Prophylaxis of Growth of Small Esophageal Varices in Cirrhosis" (2004) Gastroenterology, vol. 127, 2004, 476-484.

Neuen, Brendon L. et al "Sodium-Glucose Cotransporter 2 Inhibitors and Risk of Hyperkalemia in People With Type 2 Diabetes: A Meta-Analysis of Individual Participant Data From Randomized, Controlled Trials" (2022) Circulation, 145, 1460-1470.

Reiberger, Thomas et al., "Measurement of the Hepatic Venous Pressure Gradient and Transjugular Liver Biopsy" (2020), Jove, J. Vis. Exp., vol. 160, e58819, doi:103791/58819, 16 pages.

Reiberger, Thomas et al., "The rationale and study design of two phase II trials examining the effects of BI 685,509, a soluble guanylyl cyclase activator, on clinically significant portal hypertension in patients with compensated cirrhosis", (2023) Trials, vol. 24,293, pp. 1-17.

Reiberger, Thomas, et al., Austrian consensus guidelines on the management and treatment of portal hypertension (Billroth III), (2017) Wien Klin Wochenschr, vol. 129, S3, S135-S158.

Rodan, Allyn "Potassium: friend or foe?" (2017) Pediatric Nephrology, 32, 1109-1121.

Villanueva, Candid et al., "Development of Hyperdynamic Circulation and Response to β-Blockers in Compensated Cirrhosis with Portal Hypertenstion" (2016), Hepatology, vol. 63, 197-206.

Wanner, Christoph et al. "Empagliflozin and Progression of Kidney Disease in Type 2 Diabetes" (2016) NEJM, vol. 375, 323-334.

\* cited by examiner

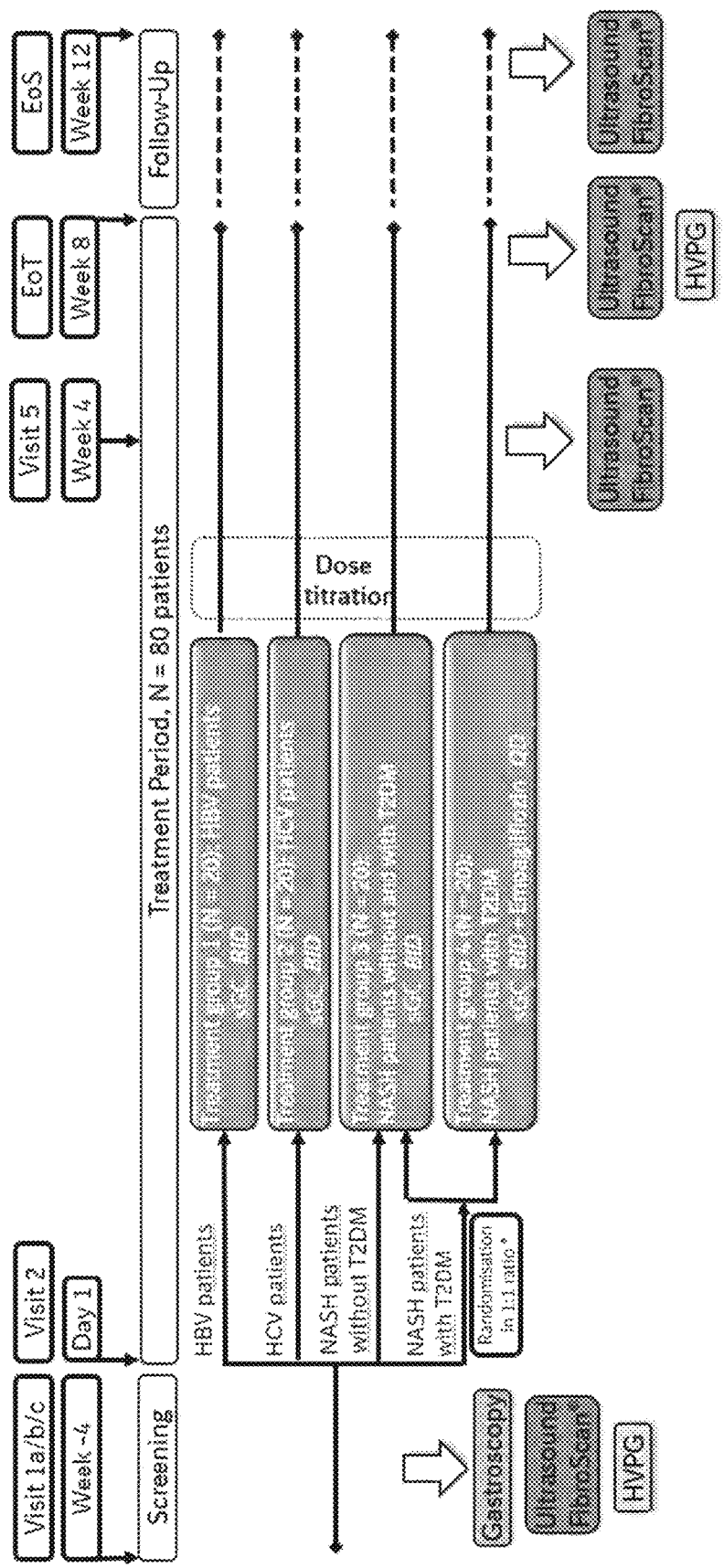

SOLUBLE GUANYLATE CYCLASE ACTIVATORS FOR TREATING PORTAL HYPERTENSION

FIELD OF THE INVENTION

The invention relates to the use of certain soluble guanylate cyclase activators for treating certain disorders including portal hypertension. The invention further relates to the use of the soluble guanylate cyclase activators in combination with sodium-glucose cotransporter-2 (SGLT2) inhibitors.

BACKGROUND

Cirrhosis is the end-stage liver condition caused by multiple chronic diseases, like hepatitis C virus infection (HCV), chronic alcohol abuse, or metabolic syndrome with non-alcoholic fatty liver disease (NAFLD). Cirrhosis by itself is a chronic condition with a high mortality. It is a heterogenous disease that is classified into two main prognostic stages: compensated and decompensated cirrhosis. This classification depends on the presence or absence of clinically evident decompensating events (specifically ascites [more than perihepatic ascites]), variceal haemorrhage (VH) and/or apparent hepatic encephalopathy (HE). (See, e.g., G. Garcia-Tsao et al., "Portal hypertensive bleeding in cirrhosis: Risk stratification, diagnosis, and management": 2016 practice guidance by the American Association for the Study of Liver Diseases. Hepatology 2017;65(1):310-335.) Currently, there is no treatment available for cirrhosis for reduction of fibrotic tissue or regeneration of hepatocytes. The main treatment goal is to delay decompensation, improve quality of life, and treat the symptoms of cirrhosis and especially decompensation.

Portal hypertension (PH) is the initial and main consequence of cirrhosis and is responsible for the majority of its complications. (See, e.g. GBD 2013 Mortality and Causes of Death Collaborators. Global, regional, and national age-sex specific all-cause and cause-specific mortality for 240 causes of death, 1990-2013: a systematic analysis for the Global Burden of Disease Study 2013. Lancet 2015;385(9963):117-171). The only currently recommended clinical approaches to prevent PH-related decompensating events in patients with compensated cirrhosis are endoscopic variceal ligations or off-label use of non-selective beta-blockers (NSBBs) or carvedilol for the prophylaxis of a first variceal bleeding. However, not all patients with PH achieve a haemodynamic response with these current treatment options. NSBBs and carvedilol are currently used to prevent complications of cirrhosis and improve survival in patients, but these benefits only occur in less than half of patients treated, and mostly in those who achieve a significant decrease in portal pressure. An unmet need remains for a substantial number of patients who cannot tolerate treatment with NSBBs or carvedilol due to decreased systemic blood pressure (BP) and heart rate (HR), and who have a higher risk for further progression into decompensation.

Therefore, there is an existing unmet medical need to reduce portal pressure and improve liver perfusion in this population of patients with PH and especially clinically significant portal hypertension (CSPH) and compensated cirrhosis. CSPH is associated with an increased risk of developing varices, overt clinical decompensation (ascites, VH, and HE), postsurgical decompensation, and hepatocellular carcinoma. (See, e.g., C. Villanueva et al., "Development of hyperdynamic circulation and response to beta-blockers in compensated cirrhosis with portal hypertension. Hepatology, 2016;63(1):197-206; G. D'Amico et al., "Competing risks and prognostic stages of cirrhosis: a 25-year inception cohort study of 494 patients. Aliment Pharmacol Ther 2014;39(10):1180-1193; and G. Garcia-Tsao et al., "Portal hypertensive bleeding in cirrhosis: Risk stratification, diagnosis, and management: 2016 practice guidance by the American Association for the Study of Liver Diseases. Hepatology 2017;65(1):310-335).

BRIEF SUMMARY OF THE INVENTION

The present invention relates to methods for treating patients with compensated cirrhosis, comprising administering to the patient a pharmaceutically effective amount of a soluble guanylate cyclase (sGC) activator, or a pharmaceutically acceptable salt thereof.

The invention also relates to a sGC activator, or a pharmaceutically acceptable salt thereof, for use in treating a patient with compensated cirrhosis, wherein the sGC activator, or a pharmaceutically acceptable salt thereof.

In another embodiment, the invention relates to methods for treating a patient with clinically significant portal hypertension in compensated cirrhosis, comprising administering to the patient a therapeutically effective amount of a sGC activator, or a pharmaceutically acceptable salt thereof.

In another embodiment, the invention relates to a sGC activator, or a pharmaceutically acceptable salt thereof, for use in treating a patient with clinically significant portal hypertension in compensated cirrhosis.

In another embodiment, the invention relates to methods for reducing the portal pressure in a patient with clinically significant portal hypertension in compensated cirrhosis, comprising administering to the patient a therapeutically effective amount of a sGC activator, or a pharmaceutically acceptable salt thereof, wherein the In one embodiment, the CSPH in compensated cirrhosis due to or caused by, Hepatitis B Virus (HBV), Hepatitis C Virus (HCV), or Non-Alcoholic Steatohepatitis (NASH).

In another embodiment, the present invention relates to methods for treating a patient with clinically significant portal hypertension in compensated cirrhosis, comprising administering to the patient a therapeutically effective amount of a sGC activator, or a pharmaceutically acceptable salt thereof, wherein the CSPH in compensated cirrhosis due to or caused by HBV, HCV, or NASH.

In one embodiment, the invention relates to methods for treating patients with clinically significant portal hypertension in compensated cirrhosis due to HBV.

In another embodiment, the invention relates to methods for treating patients with clinically significant portal hypertension in compensated cirrhosis due to HCV.

In another embodiment, the invention relates to methods for treating patients with clinically significant portal hypertension in compensated cirrhosis due to NASH.

In another embodiment, the invention relates to methods for treating patients with clinically significant portal hypertension in compensated cirrhosis due to NASH, wherein said patient has type 2 diabetes mellitus.

In another embodiment, the invention relates to methods for treating a patient with clinically significant portal hypertension in compensated cirrhosis due to NASH, wherein said patient does not have type 2 diabetes mellitus.

In another embodiment, the invention relates to any of the methods or uses described above, further comprising administering a pharmaceutically effective amount of a SLGT2 inhibitor, or a pharmaceutically acceptable salt thereof.

In another embodiment, the invention relates to a method for treating a patient with compensated cirrhosis due to NASH, the method comprising administering to the patient a pharmaceutically effective amount of a sGC activator of the invention, or a pharmaceutically acceptable salt thereof, in combination with a pharmaceutically effective amount of a SLGT2 inhibitor, or a pharmaceutically acceptable salt thereof.

In another embodiment, the invention relates to a method for treating a type 2 diabetes mellitus patient with CSPH in compensated cirrhosis due to NASH, the method comprising administering to the patient a pharmaceutically effective amount of a sGC activator of the invention, or a pharmaceutically acceptable salt thereof, in combination with a pharmaceutically effective amount of a SGLT2 inhibitor, or a pharmaceutically acceptable salt thereof.

In another embodiment, the SLGT2 inhibitor when used, is selected from the group consisting of group consisting of empagliflozin, dapagliflozin, canagliflozin, ertugliflozin, sotagliflozin, licogliflozin and ipragliflozin.

In another embodiment, the invention relates to the embodiment immediately above, wherein the SGLT2 inhibitor is selected from the group consisting of group consisting of empagliflozin, dapagliflozin and canagliflozin.

In another embodiment, the invention relates to the embodiment immediately above, wherein the SGLT2 inhibitor is empagliflozin.

In another embodiment, the invention relates to a method for treating a patient with CSPH in compensated cirrhosis due to NASH, the method comprising administering to the patient a pharmaceutically effective amount of a sGC activator of the invention, or a pharmaceutically acceptable salt thereof, in combination with a pharmaceutically effective amount of empagliflozin.

In another embodiment, the invention relates to a method for treating a type 2 diabetes mellitus patient with CSPH in compensated cirrhosis due to NASH, the method comprising administering to the patient a pharmaceutically effective amount of a sGC activator of the invention, or a pharmaceutically acceptable salt thereof, in combination with a pharmaceutically effective amount of empagliflozin.

Within the scope of the invention, the SGLT2 inhibitor may also inhibit SGLT1, that is, a dual SGLT1/SGLT2 inhibitor. In one embodiment, the SGLT2 inhibitor, when used, is a dual SGLT1/SGLT2 inhibitor selected from the group consisting of sotagliflozin and licogliflozin.

WO 2014/039434 and WO 2020/011804 describe oral, small-molecule activators of sGC useful in the methods of the invention ("the sGC activators of the invention"). Unless otherwise stated herein, the terms the "sGC activators of the invention," "the compounds of the invention" and "the compounds of formula (I)" are used interchangeably.

In one embodiment of the invention, the sGC activator used in the methods of the invention is a compound of formula (I)

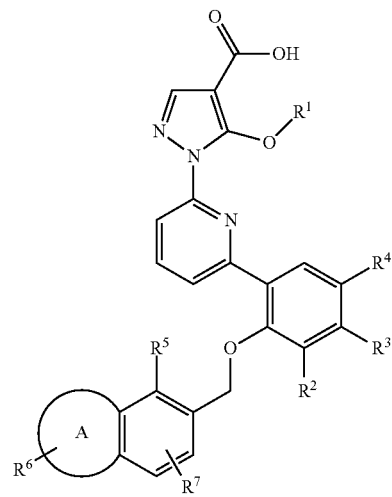

wherein:
A is a 5-7 membered saturated heterocyclyl group containing one nitrogen and optionally one oxygen, wherein one carbon of said heterocyclyl group is optionally substituted with one or two groups selected from $C_{1-3}$alkyl and oxo;
$R^1$ is $C_{1-4}$ alkyl optionally substituted with a methoxy group;
$R^2$ is selected from H, F, Cl, $C_{1-3}$alkyl, —CN, —OMe and —$CF_3$;
$R^3$ is selected from H and —$CH_3$;
$R^4$ is selected from H, F, —$CH_3$ and —OMe;
$R^5$ is selected from H, Cl, —$CH_3$, —CH2CH$_3$, —$CF_3$, F, and —OMe;
$R^6$ is bonded to the nitrogen on A and is selected from H, $C_{1-6}$alkyl, —$(CH_2)_nC_{3-6}$cycloalkyl, —$C(O)C_{1-6}$alkyl, —$(CH_2)_n$ heterocyclyl, —$(CH_2)_n$ aryl—$(CH_2)_n$ heteroaryl, —$SO_2$aryl, $SO_2C_{1-6}$alkyl wherein said $C_{1-6}$alkyl, —$(CH_2)_n$ heterocyclyl, —$(CH_2)_n$ cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH, oxo, —$(CH_2)_{1-3}O(CH_2)_{2-3}OH$, and —$SO_2CH_3$;
$R^7$ is selected from H, —$CH_3$, —$CH_2CH_3$, —$CF_3$, F, and —CN;
n is 0, 1 or 2
or a salt thereof.

In another embodiment, the invention relates to the method described in the embodiment above, wherein:
A is a 5-7 membered saturated heterocyclyl group containing one nitrogen, wherein one carbon of said heterocyclyl group is optionally substituted with one or two $C_{1-3}$alkyl groups;
$R^1$ is $C_{1-3}$alkyl;
$R^2$ is selected from H, F, Cl, $C_{1-3}$alkyl, —CN, —OMe and —$CF_3$;
$R^3$ is selected from H and —$CH_3$;
$R^4$ is selected from H and F;
$R^5$ is selected from H, Cl and —$CH_3$;
$R^6$ is bonded to the nitrogen on A and is selected from H, $C_{1-6}$alkyl, —$(CH_2)_nC_{3-6}$cycloalkyl, —$C(O)C_{1-6}$alkyl, —$(CH_2)_n$ heterocyclyl, —$(CH_2)_n$ aryl and —$(CH_2)_n$ heteroaryl, wherein said $C_{1-6}$alkyl, —$(CH_2)_n$ heterocyclyl, —$(CH^2)_n$ cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH and —$SO_2CH_3$, $R^7$ is H;

and n is 0, 1 or 2;

or a salt thereof.

In another embodiment, the invention relates to the methods as described in any of the embodiments above, wherein:

$R^1$ is methyl, ethyl or isopropyl; and the group

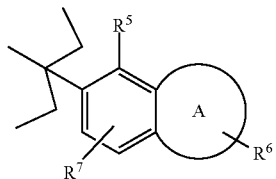

is selected from:

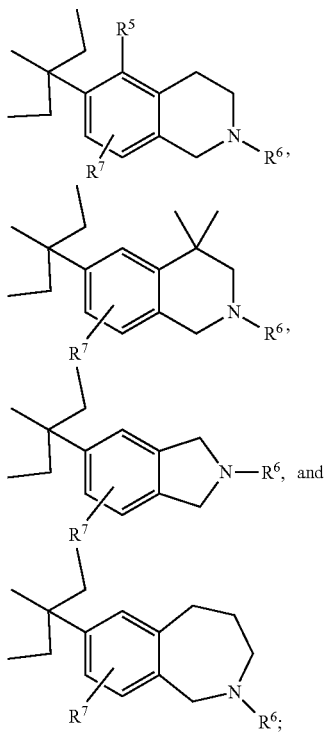

or a salt thereof.

In another embodiment, the invention relates to the methods as described in any of the embodiments above, wherein:

$R^2$ is selected from —$CH_3$, F, Cl, and —$CF_3$; and $R^6$ is selected from H, $C_{1-6}$alkyl, —$(CH_2)_nC_{3-6}$cycloalkyl, —$C(O)C_{1-6}$alkyl and —$(CH_2)_n$ heterocyclyl, wherein said $C_{1-6}$alkyl, —$(CH_2)_n$ cycloalkyl and —$(CH_2)_n$ heterocyclyl are optionally substituted with one to four groups independently selected from $C_{1-3}$alkyl, halogen, $C_{1-3}$alkoxy, —$CF_3$, —OH and —$SO_2CH_3$;

or a salt thereof.

In another embodiment, the invention relates to the methods as described in any of the embodiments above wherein said heterocyclyl referred to in $R^6$ is selected from oxetanyl, tetrahydrofuranyl, tetrahydropyranyl, 2-oxabicyclo[3.2.0]heptanyl, [1,4]dioxanyl, 8-oxabicyclo[3.2.1]octanyl, 1-oxaspiro[4.5]decanyl and pyrrolidin-2-one;

said heteroaryl referred to in $R^6$ is selected from imidazolyl, isoxazolyl, pyrazinyl, pyrazolyl, pyridinyl, pyrimidinyl, thiazolyl and 4,5,6,7-tetrahydrobenzothiazolyl;

and said aryl referred to in $R^6$ is phenyl;

or a salt thereof.

In another embodiment, the invention relates to the methods as described in any of the embodiments above, wherein:

$R^6$ is —$(CH^2)_n$ heterocyclyl, wherein said heterocyclyl is selected from oxetanyl, tetrahydrofuranyl, tetrahydropyranyl, 2-oxabicyclo[3.2.0]heptanyl, [1,4]dioxanyl, 8-oxabicyclo[3.2.1]octanyl and 1-oxaspiro[4.5]decanyl;

or a salt thereof.

In another embodiment, the invention relates to the methods as described in any of the embodiments above, wherein:

$R^2$ is —$CH^3$;

$R^3$ is H;

$R^4$ is H or —$CH_3$;

$R^5$ is H, or —$CH_3$;

$R_7$ is in the position para to $R^5$ and is H, —$CH_3$ or —$CH_2CH_3$;

or a salt thereof.

In another embodiment, the invention relates to the methods as described in any of the embodiments above, wherein:

the group

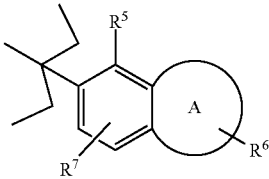

is

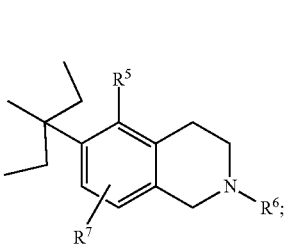

or a salt thereof.

In another embodiment, the invention relates to the methods as described in any of the embodiments above, wherein:

$R^3$ is H; and $R^4$ is H;

or a salt thereof.

Table 1 shows representative compounds of the invention which can be used according to the methods of the invention.

TABLE 1

| Cpd No. | Structure |
|---|---|
| 1 | (structure) |
| 2 | (structure) |
| 3 | (structure) |
| 4 | (structure) |
| 5 | (structure) |

TABLE 1-continued

| Cpd No. | Structure |
|---|---|
| 6 | (structure) |
| 7 | (structure) |
| 8 | (structure) |
| 9 | (structure) |
| 10 | (structure) |
| 11 | (structure) |

TABLE 1-continued
| Cpd No. | Structure |
|---|---|
| 12 | 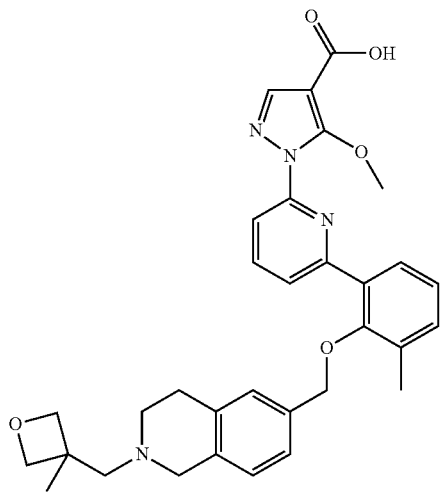 [SMILES: COc1c(C(=O)O)cnn1-c1cccc(-c2cccc(C)c2OCc2ccc3c(c2)CCN(CC2(C)COC2)C3)n1] |
| 13 | 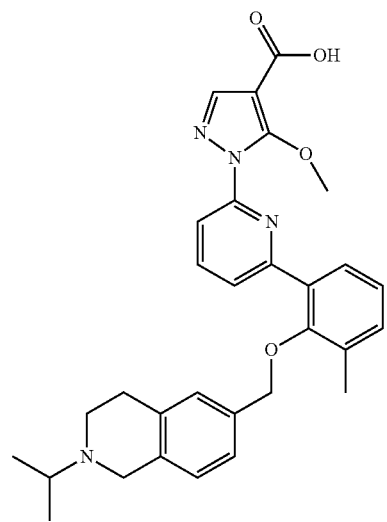 [SMILES: COc1c(C(=O)O)cnn1-c1cccc(-c2cccc(C)c2OCc2ccc3c(c2)CCN(C(C)C)C3)n1] |
| 14 | 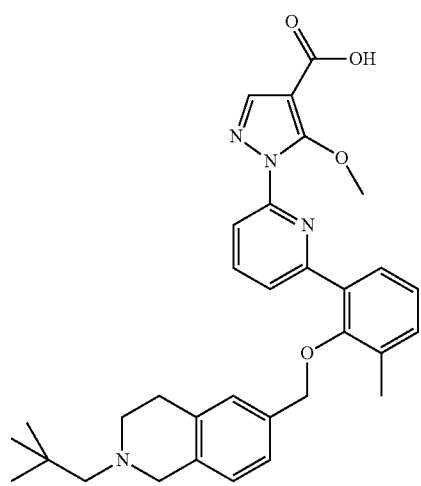 [SMILES: COc1c(C(=O)O)cnn1-c1cccc(-c2cccc(C)c2OCc2ccc3c(c2)CCN(CC(C)(C)C)C3)n1] |
| 15 | 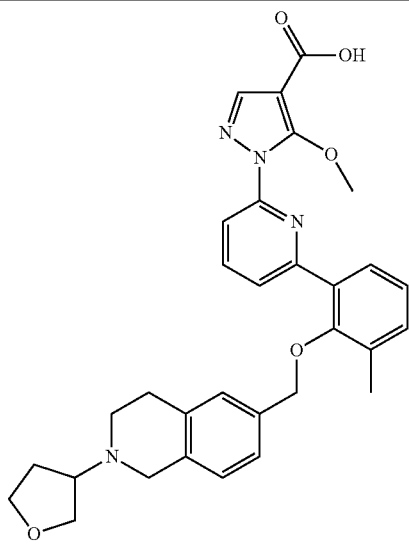 |
| 16 | 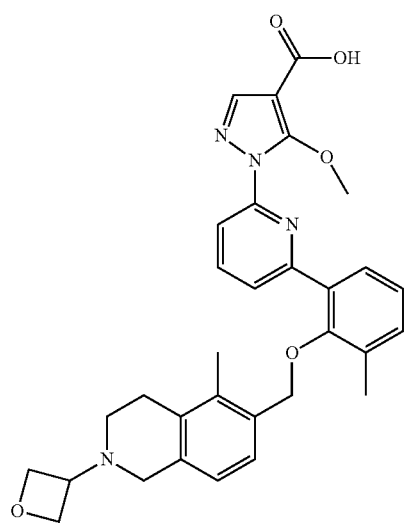 [SMILES: COc1c(C(=O)O)cnn1-c1cccc(-c2cccc(C)c2OCc2ccc3c(c2C)CCN(C2COC2)C3)n1] |
| 17 | 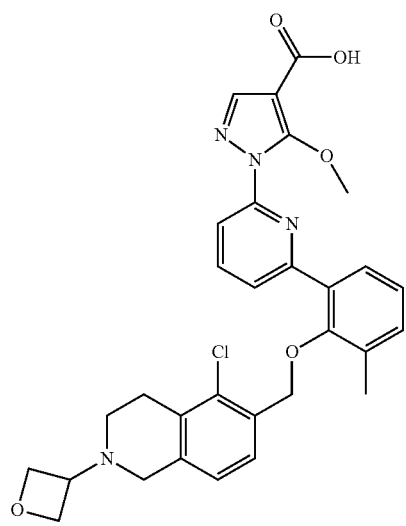 |

TABLE 1-continued
| Cpd No. | Structure |
|---|---|
| 18 | 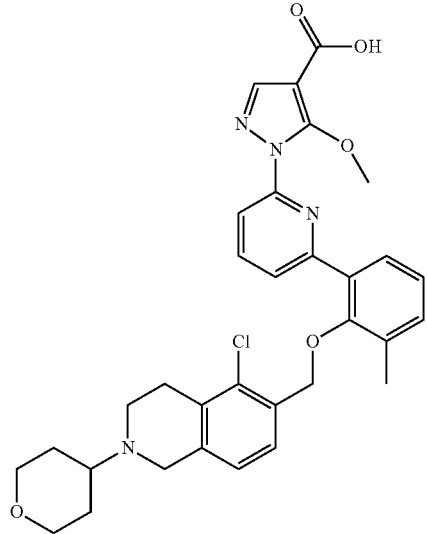 [SMILES: COc1c(C(=O)O)cnn1-c1cccc(-c2cccc(C)c2OCc2ccc3c(c2Cl)CCN(C2CCOCC2)C3)n1] |
| 19 | 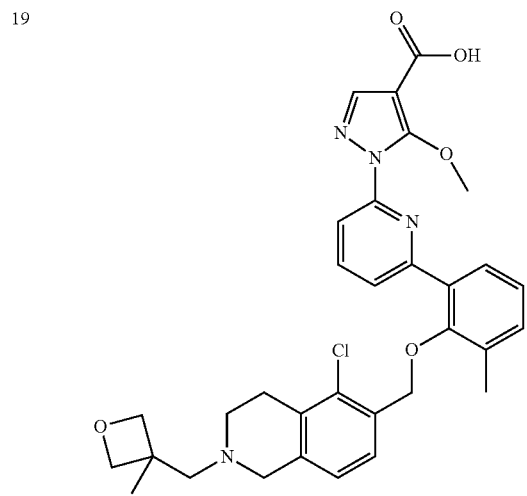 |
| 20 | 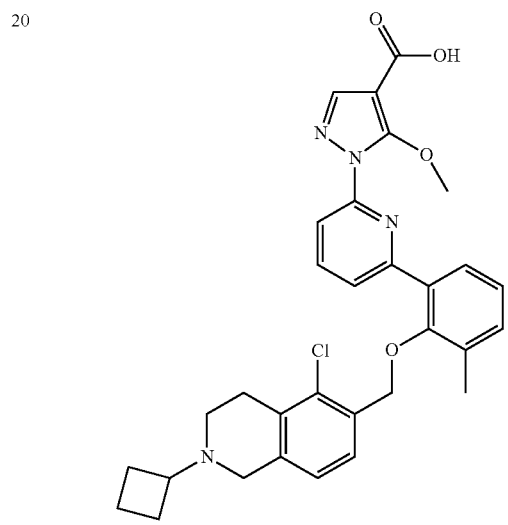 |
TABLE 1-continued
| Cpd No. | Structure |
|---|---|
| 21 | 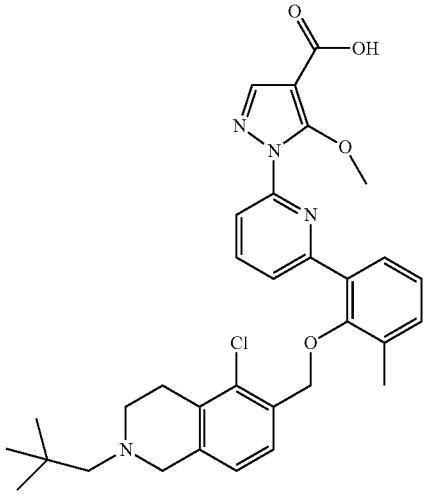 [SMILES: COc1c(C(=O)O)cnn1-c1cccc(-c2cccc(C)c2OCc2ccc3c(c2Cl)CCN(CC(C)(C)C)C3)n1] |
| 22 | 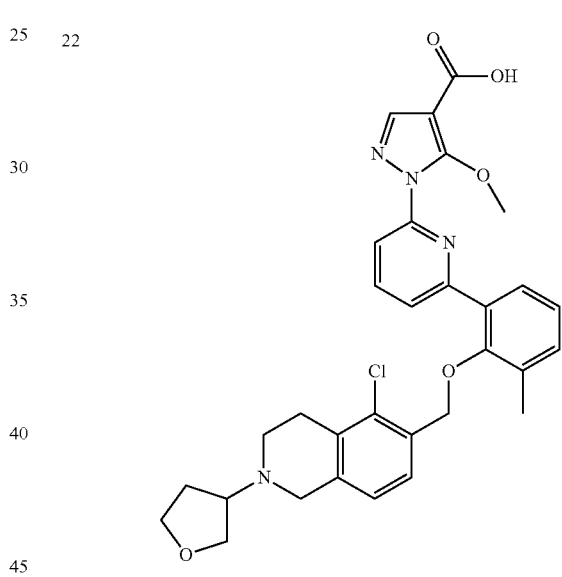 |
| 23 | 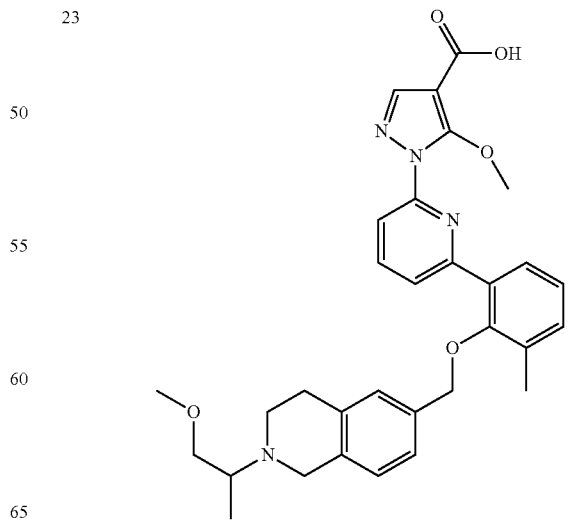 |

TABLE 1-continued

| Cpd No. | Structure |
|---|---|
| 24 | (structure) |
| 25 | (structure) |
| 26 | (structure) |
| 27 | (structure) |
| 28 | (structure) |
| 29 | (structure) |

TABLE 1-continued
| Cpd No. | Structure |
|---|---|
| 30 | 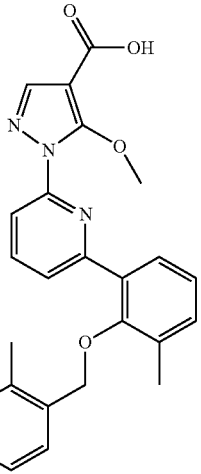 |
| 31 | 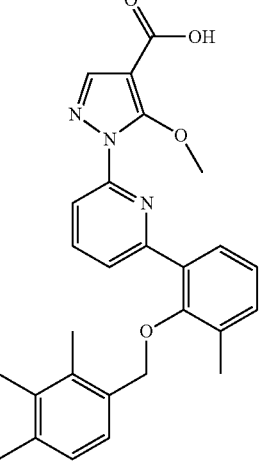 |
| 32 | 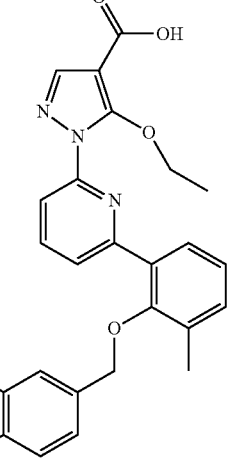 |
| 33 | 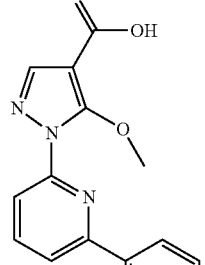 |
| 34 | 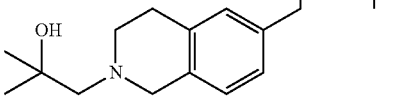 |
| 35 | 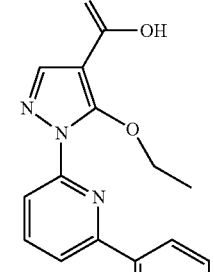 |

TABLE 1-continued
| Cpd No. | Structure |
|---|---|
| 336 | 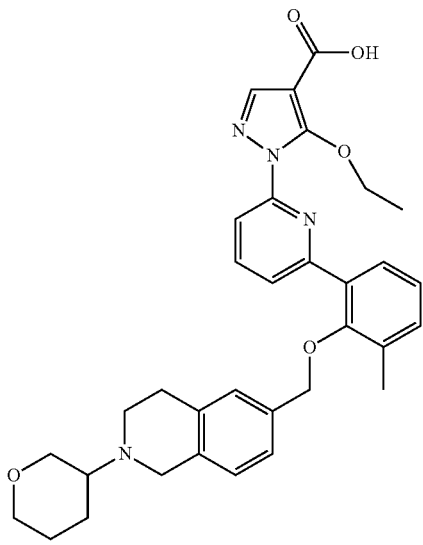 [SMILES: CCOc1c(C(=O)O)cnn1-c1cccc(-c2cccc(C)c2OCc2ccc3c(c2)CCN(C2CCCOC2)C3)n1] |
| 37 | 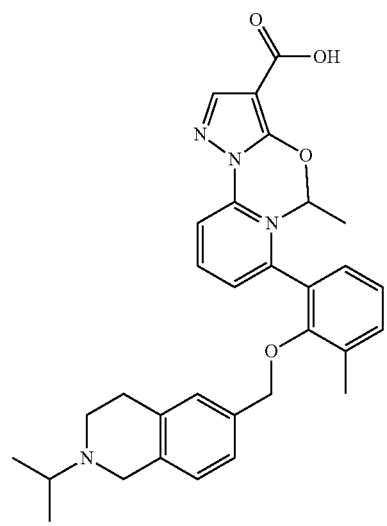 |
| 38 | 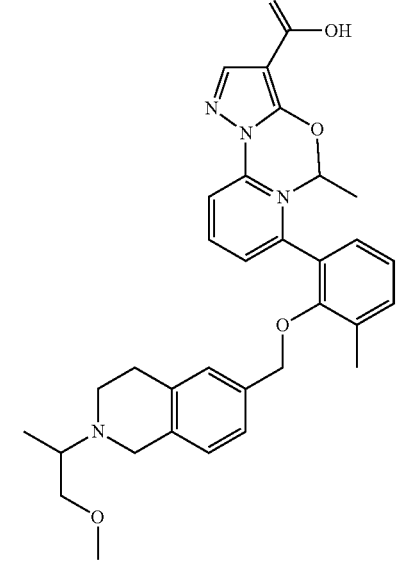 |
| 39 | 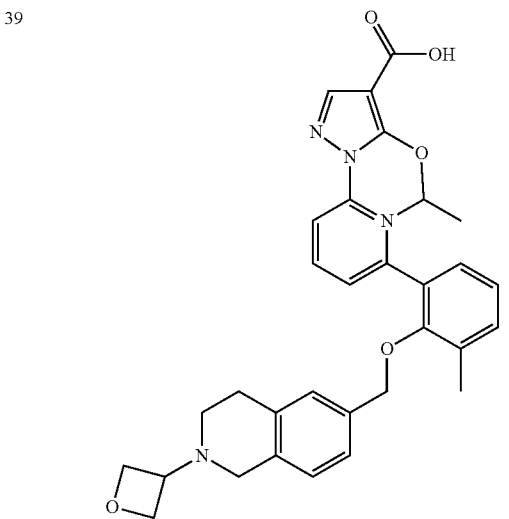 |
| 40 | 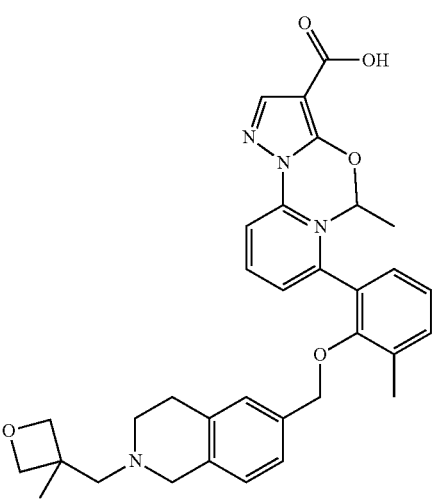 |

TABLE 1-continued
| Cpd No. | Structure |
|---|---|
| 41 | 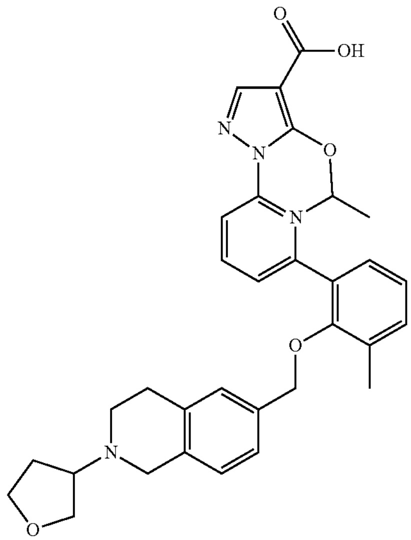 |
| 42 | 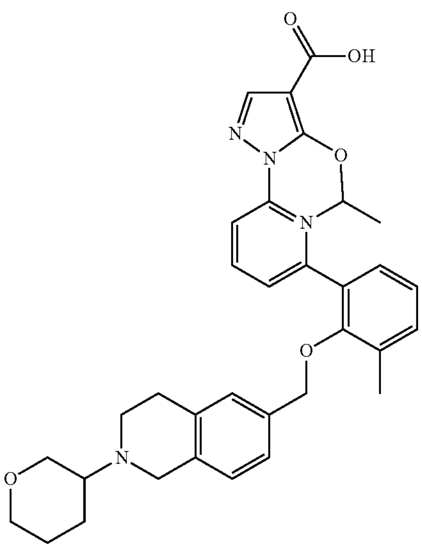 |
| 43 | 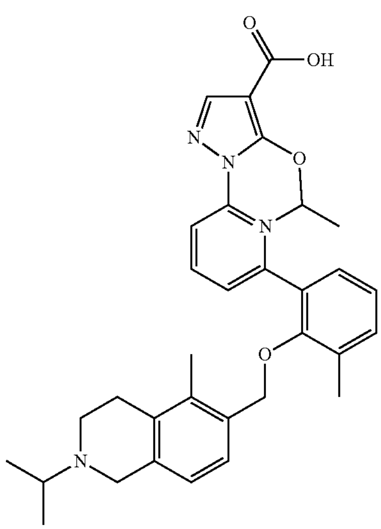 |
| 44 | 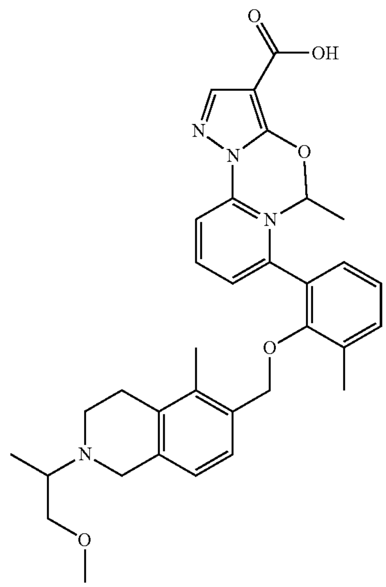 |
| 45 | 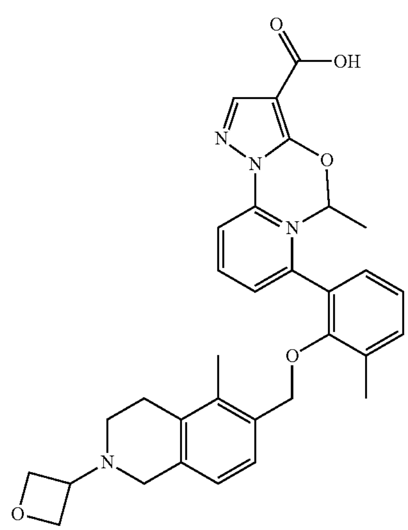 |

TABLE 1-continued

| Cpd No. | Structure |
|---|---|
| 46 | (structure) |
| 47 | (structure) |
| 48 | (structure) |
| 49 | (structure) |
| 50 | (structure) |
| 51 | (structure) |

TABLE 1-continued
| Cpd No. | Structure |
|---|---|
| 52 | 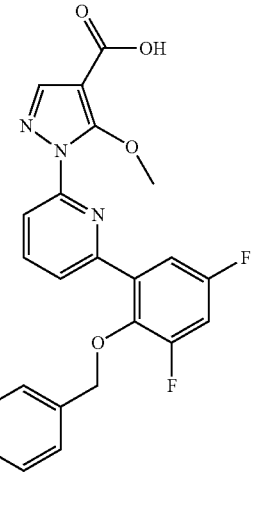 |
| 53 | 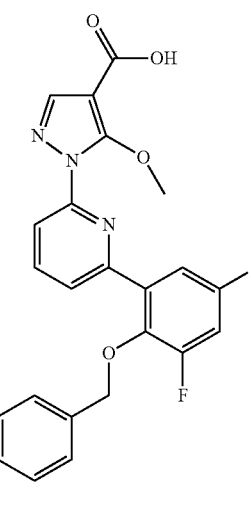 |
| 54 | 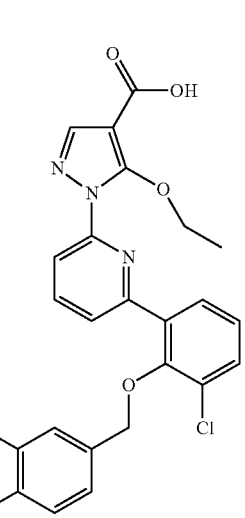 |"
TABLE 1-continued
| Cpd No. | Structure |
|---|---|
| 55 | 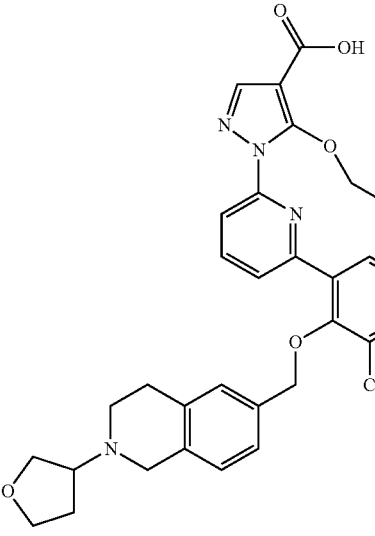 |
| 56 | 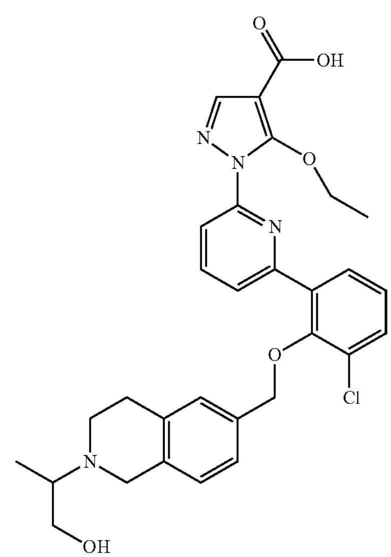 [SMILES: CCOc1c(C(=O)O)cnn1-c1cccc(-c2cccc(Cl)c2OCc2ccc3c(c2)CCN(C(C)CO)C3)n1] |

TABLE 1-continued

| Cpd No. | Structure |
|---|---|
| 57 | 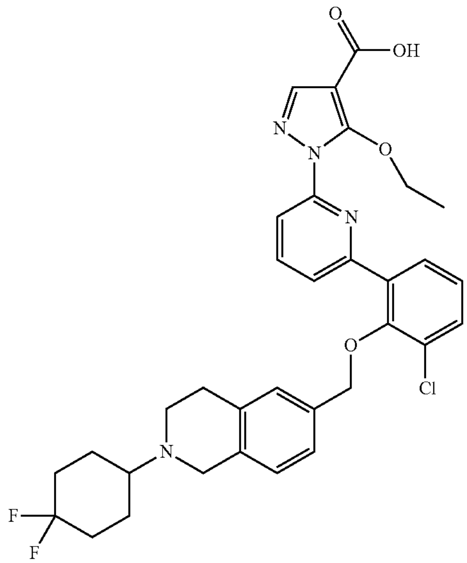 [SMILES: CCOc1c(C(=O)O)cnn1-c1cccc(-c2cccc(Cl)c2OCc2ccc3c(c2)CCN(C2CCC(F)(F)CC2)C3)n1] |
| 58 | 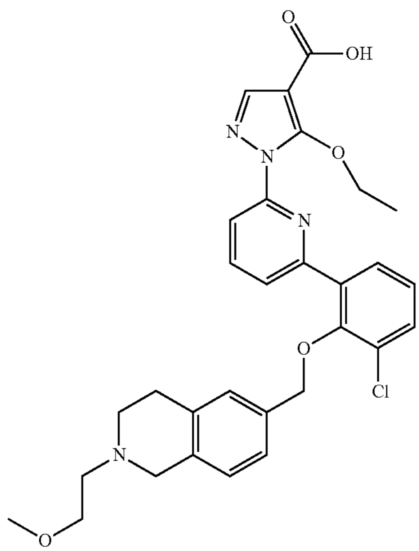 [SMILES: CCOc1c(C(=O)O)cnn1-c1cccc(-c2cccc(Cl)c2OCc2ccc3c(c2)CCN(CCOC)C3)n1] |
| 59 | 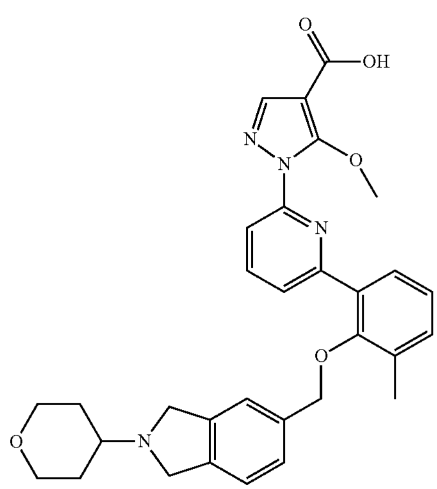 [SMILES: COc1c(C(=O)O)cnn1-c1cccc(-c2cccc(C)c2OCc2ccc3c(c2)CN(C2CCOCC2)C3)n1] |
| 60 | 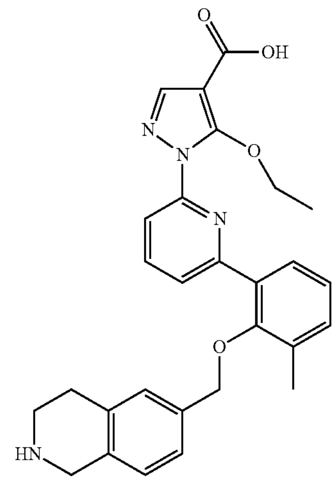 [SMILES: CCOc1c(C(=O)O)cnn1-c1cccc(-c2cccc(C)c2OCc2ccc3c(c2)CCNC3)n1] |
| 61 | 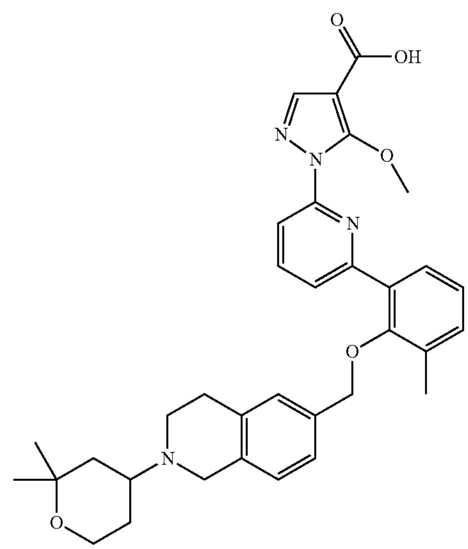 [SMILES: COc1c(C(=O)O)cnn1-c1cccc(-c2cccc(C)c2OCc2ccc3c(c2)CCN(C2CCOC(C)(C)C2)C3)n1] |
| 62 | 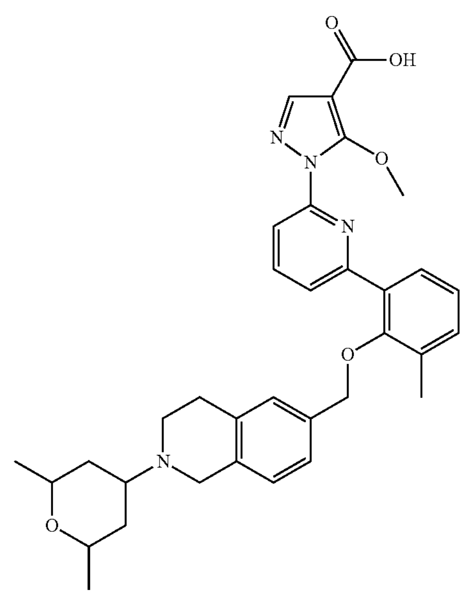 [SMILES: COc1c(C(=O)O)cnn1-c1cccc(-c2cccc(C)c2OCc2ccc3c(c2)CCN(C2CC(C)OC(C)C2)C3)n1] |

TABLE 1-continued
| Cpd No. | Structure |
|---|---|
| 63 | 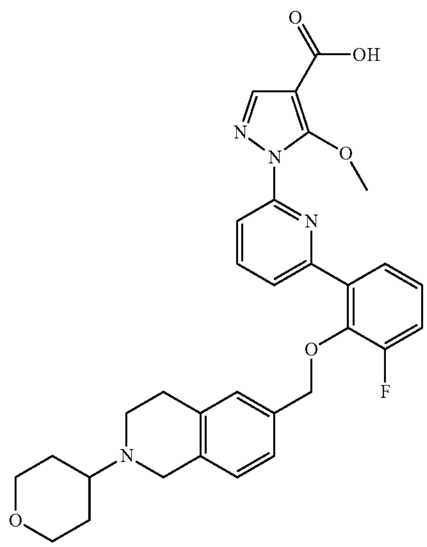 [SMILES: COc1c(C(=O)O)cnn1-c1cccc(-c2cccc(F)c2OCc2ccc3c(c2)CCN(C2CCOCC2)C3)n1] |
| 64 | 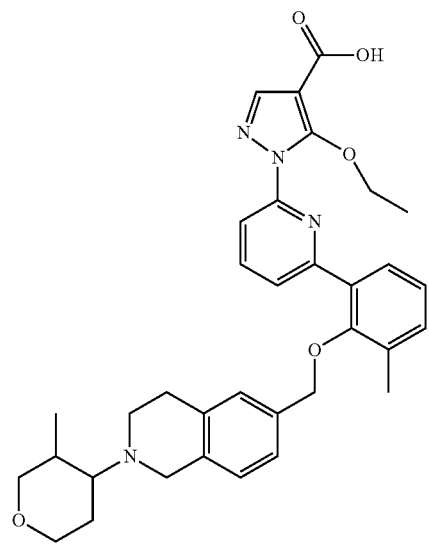 [SMILES: CCOc1c(C(=O)O)cnn1-c1cccc(-c2cccc(C)c2OCc2ccc3c(c2)CCN(C2CCOCC2C)C3)n1] |
| 65 | 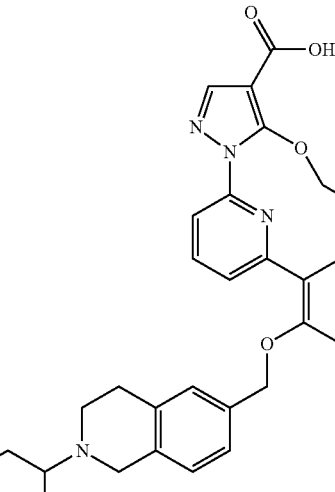 |
| 66 | 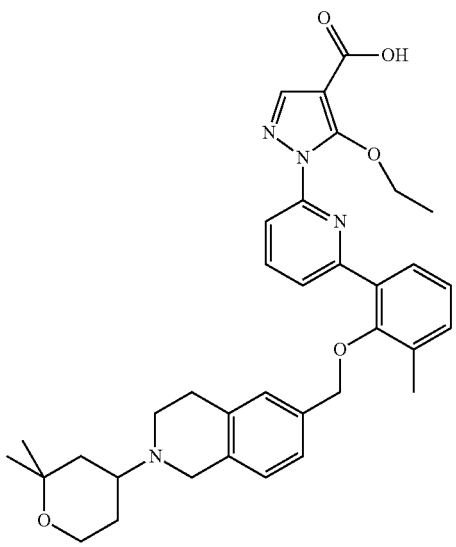 [SMILES: CCOc1c(C(=O)O)cnn1-c1cccc(-c2cccc(C)c2OCc2ccc3c(c2)CCN(C2CCOC(C)(C)C2)C3)n1] |

TABLE 1-continued
| Cpd No. | Structure |
|---|---|
| 67 | 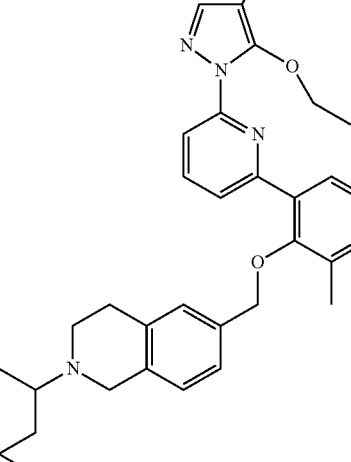 |
| 68 | 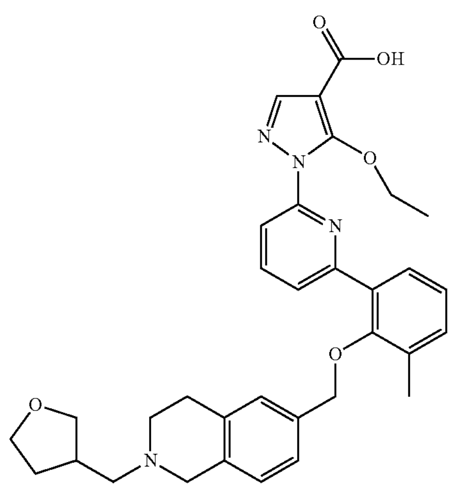 [SMILES: CCOc1c(C(=O)O)cnn1-c1cccc(-c2cccc(C)c2OCc2ccc3c(c2)CCN(CC2CCOC2)C3)n1] |
| 69 | 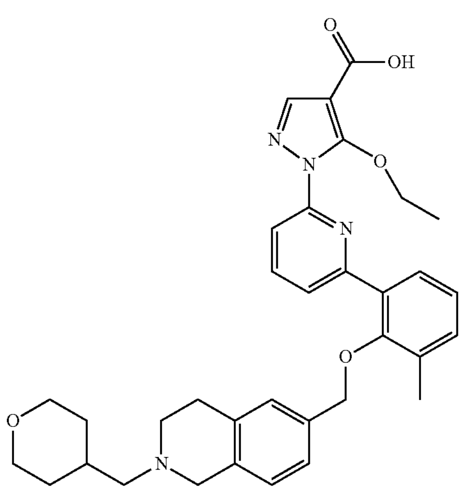 [SMILES: CCOc1c(C(=O)O)cnn1-c1cccc(-c2cccc(C)c2OCc2ccc3c(c2)CCN(CC2CCOCC2)C3)n1] |
| 70 | 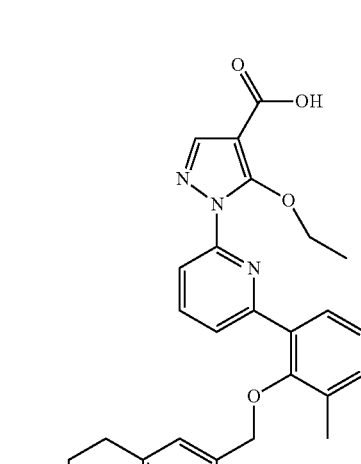 |
| 71 | |
| 72 | 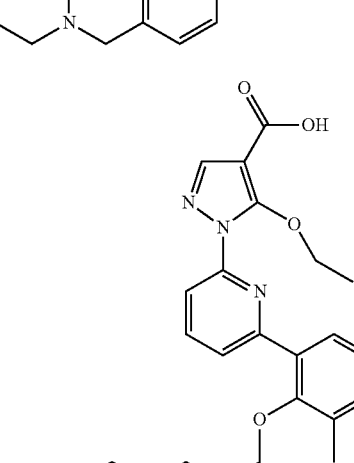 |

TABLE 1-continued

| Cpd No. | Structure |
|---|---|
| 73 | 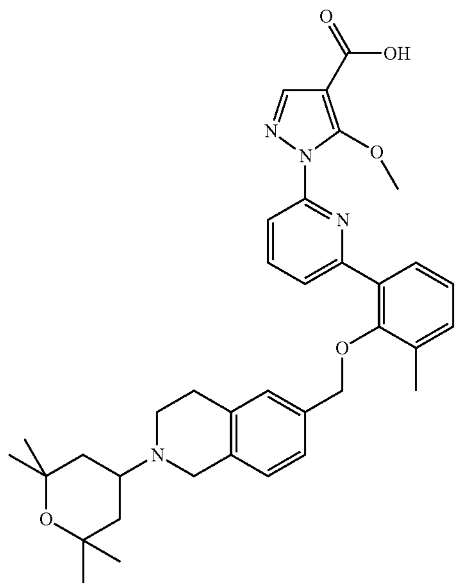 [SMILES: COc1c(C(=O)O)cnn1-c1cccc(-c2cccc(C)c2OCc2ccc3c(c2)CCN(C2CC(C)(C)OC(C)(C)C2)C3)n1] |
| 74 | 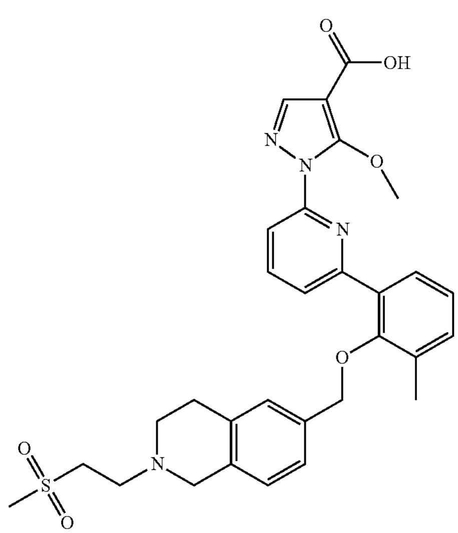 [SMILES: COc1c(C(=O)O)cnn1-c1cccc(-c2cccc(C)c2OCc2ccc3c(c2)CCN(CCS(C)(=O)=O)C3)n1] |
| 75 | |
| 76 | |

TABLE 1-continued

| Cpd No. | Structure |
|---|---|
| 77 | 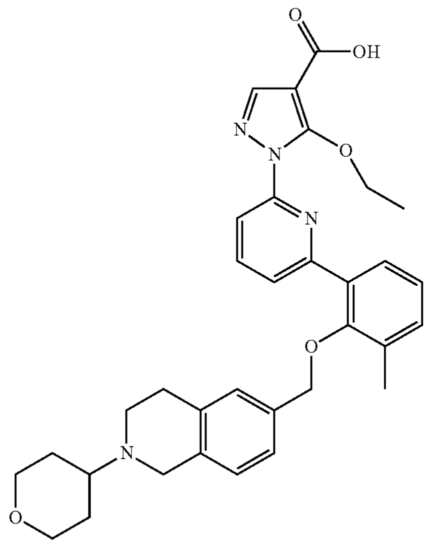 [SMILES: CCOc1c(C(=O)O)cnn1-c1cccc(-c2cccc(C)c2OCc2ccc3c(c2)CCN(C2CCOCC2)C3)n1] |
| 78 | 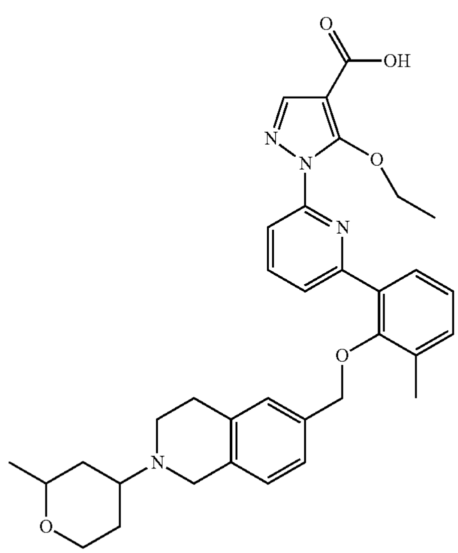 [SMILES: CCOc1c(C(=O)O)cnn1-c1cccc(-c2cccc(C)c2OCc2ccc3c(c2)CCN(C2CCOC(C)C2)C3)n1] |
| 79 | |
| 80 | |

TABLE 1-continued

| Cpd No. | Structure |
|---|---|
| 81 | 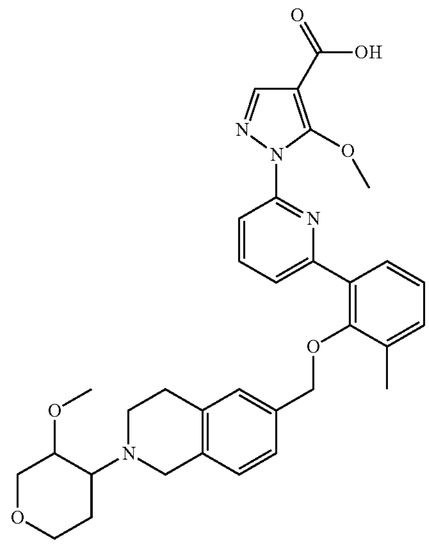 [SMILES: COc1c(C(=O)O)cnn1-c1cccc(-c2cccc(C)c2OCc2ccc3c(c2)CCN(C2CCOCC2OC)C3)n1] |
| 82 | 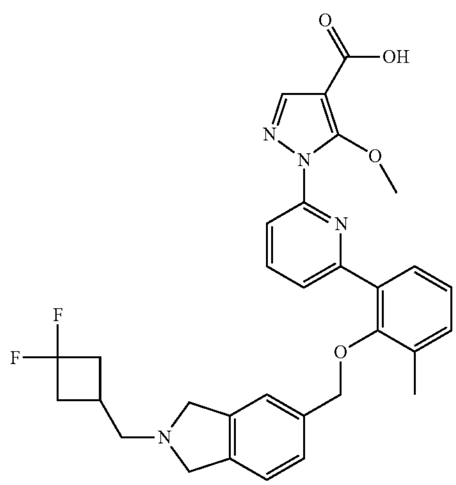 [SMILES: COc1c(C(=O)O)cnn1-c1cccc(-c2cccc(C)c2OCc2ccc3c(c2)CN(CC2CC(F)(F)C2)C3)n1] |
| 83 | 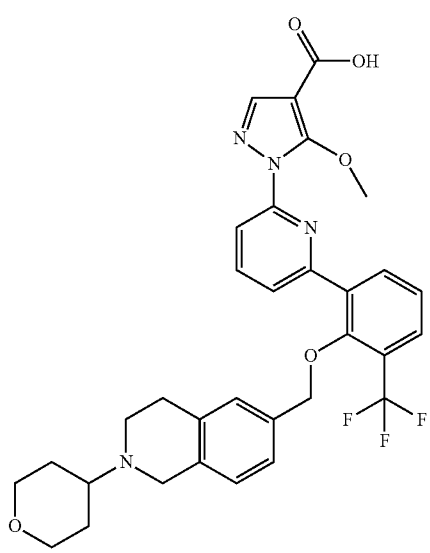 [SMILES: COc1c(C(=O)O)cnn1-c1cccc(-c2cccc(C(F)(F)F)c2OCc2ccc3c(c2)CCN(C2CCOCC2)C3)n1] |
| 84 | |
| 85 | |
| 86 | |

TABLE 1-continued
| Cpd No. | Structure |
|---|---|
| 87 | 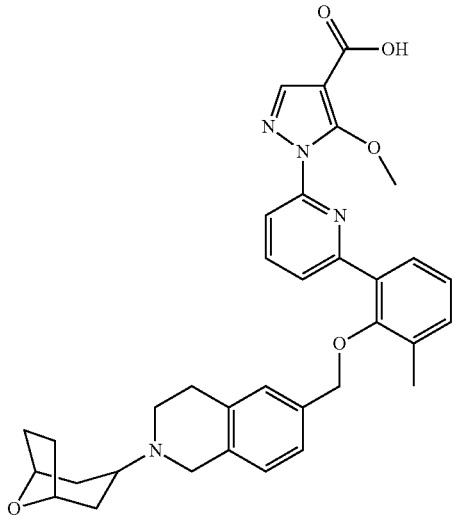 [SMILES: COc1c(C(=O)O)cnn1-c1cccc(-c2cccc(C)c2OCc2ccc3c(c2)CCN(C2CC4CCC(C2)O4)C3)n1] |
| 88 | 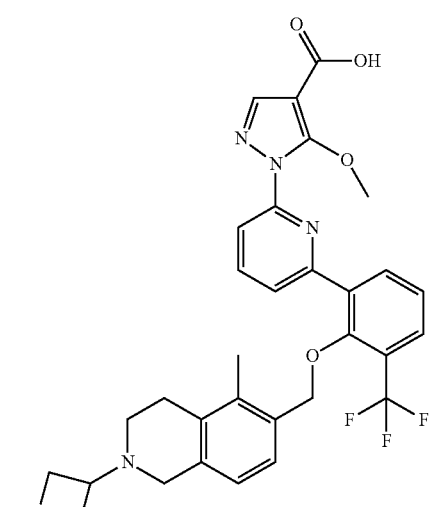 |
| 89 | 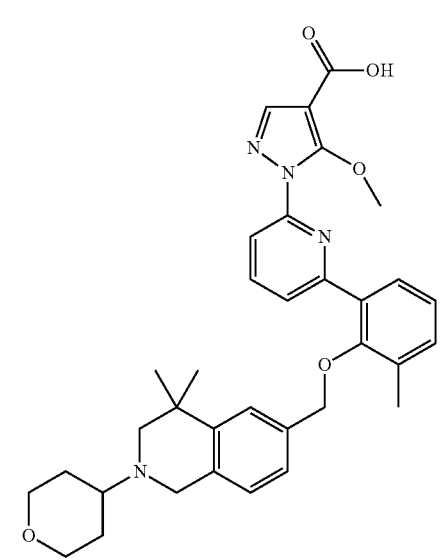 [SMILES: COc1c(C(=O)O)cnn1-c1cccc(-c2cccc(C)c2OCc2ccc3c(c2)C(C)(C)CN(C2CCOCC2)C3)n1] |
| 90 | 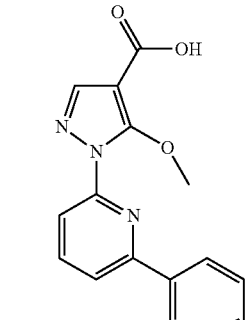 |
| 91 | 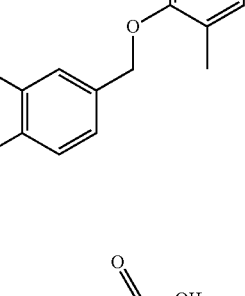 |
| 92 | 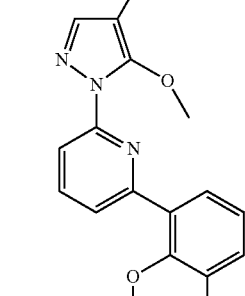 |

TABLE 1-continued
| Cpd No. | Structure |
|---|---|
| 93 | 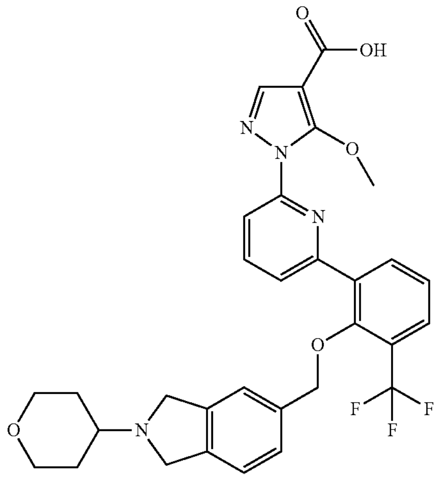 [SMILES: COc1c(C(=O)O)cnn1-c1cccc(-c2cccc(C(F)(F)F)c2OCc2ccc3c(c2)CN(C2CCOCC2)C3)n1] |
| 94 | 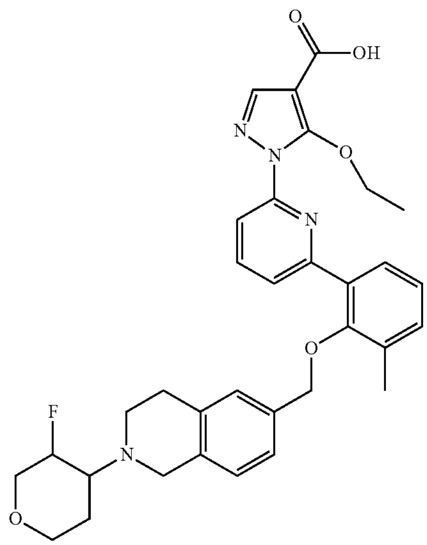 [SMILES: CCOc1c(C(=O)O)cnn1-c1cccc(-c2cccc(C)c2OCc2ccc3c(c2)CCN(C2CCOCC2F)C3)n1] |
| 95 | 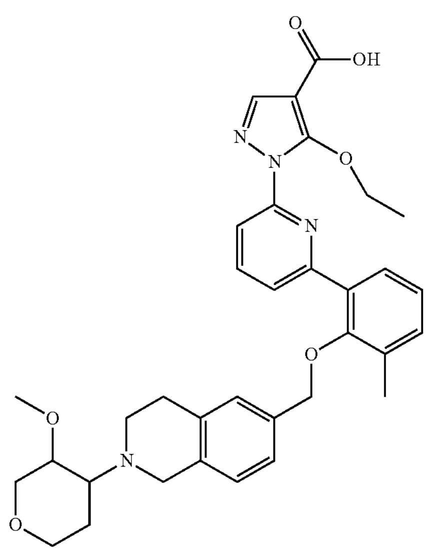 [SMILES: CCOc1c(C(=O)O)cnn1-c1cccc(-c2cccc(C)c2OCc2ccc3c(c2)CCN(C2CCOCC2OC)C3)n1] |
| 96 | |
| 97 | |
| 98 | |
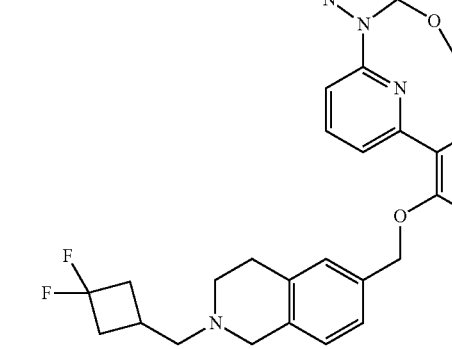

TABLE 1-continued

| Cpd No. | Structure |
|---|---|
| 99 | 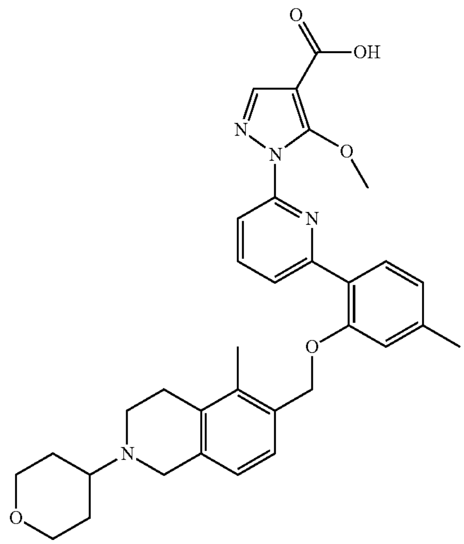 [SMILES: COc1c(C(=O)O)cnn1-c1cccc(-c2ccc(C)cc2OCc2ccc3c(c2C)CCN(C2CCOCC2)C3)n1] |
| 100 | 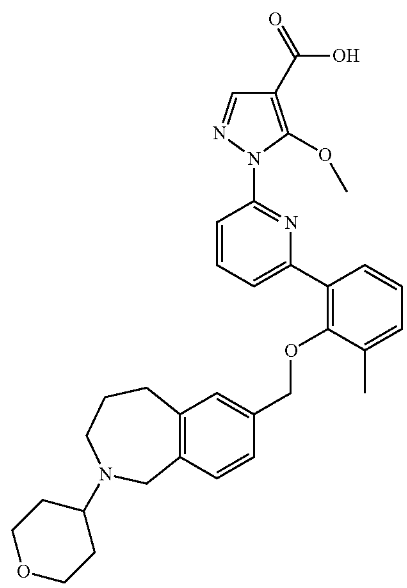 [SMILES: COc1c(C(=O)O)cnn1-c1cccc(-c2cccc(C)c2OCc2ccc3c(c2)CCCN(C2CCOCC2)C3)n1] |
| 101 | 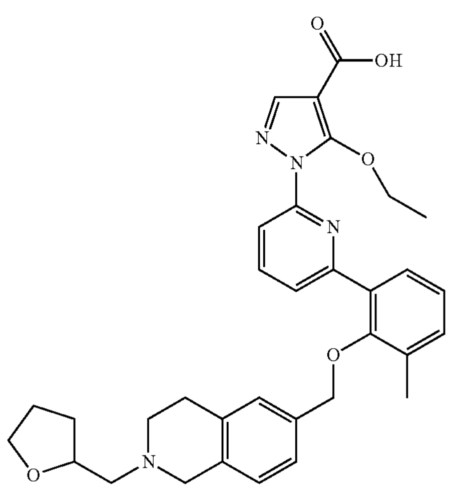 [SMILES: CCOc1c(C(=O)O)cnn1-c1cccc(-c2cccc(C)c2OCc2ccc3c(c2)CCN(CC2CCCO2)C3)n1] |
| 102 | |
| 103 | |

TABLE 1-continued

| Cpd No. | Structure |
|---|---|
| 104 | *(chemical structure)* |
| 105 | *(chemical structure)* |
| 106 | *(chemical structure)* |
| 107 | *(chemical structure)* |

TABLE 1-continued
| Cpd No. | Structure |
|---|---|
| 108 | 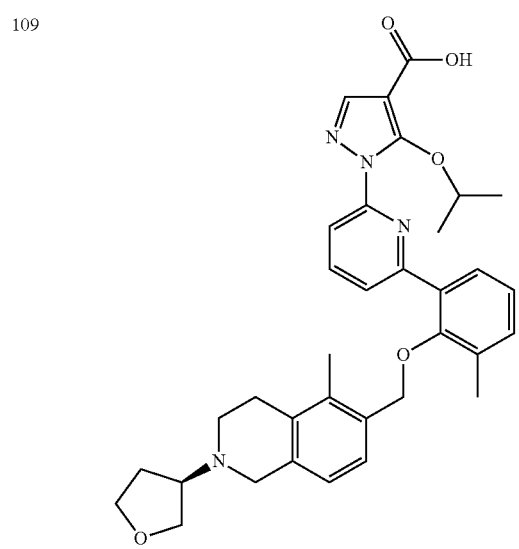 |
| 109 | 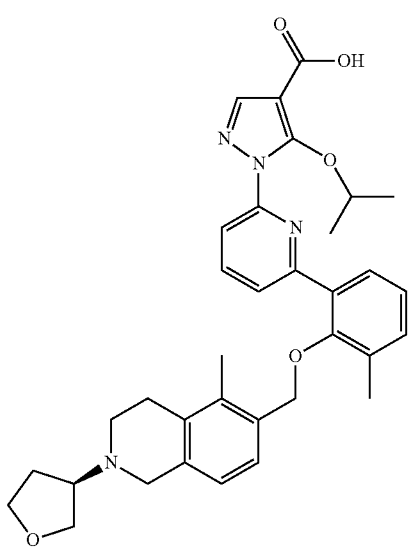 [SMILES: Cc1cccc(-c2cccc(-n3ncc(C(=O)O)c3OC(C)C)n2)c1OCc1ccc2c(c1C)CCN([C@@H]1CCOC1)C2] |
| 110 | 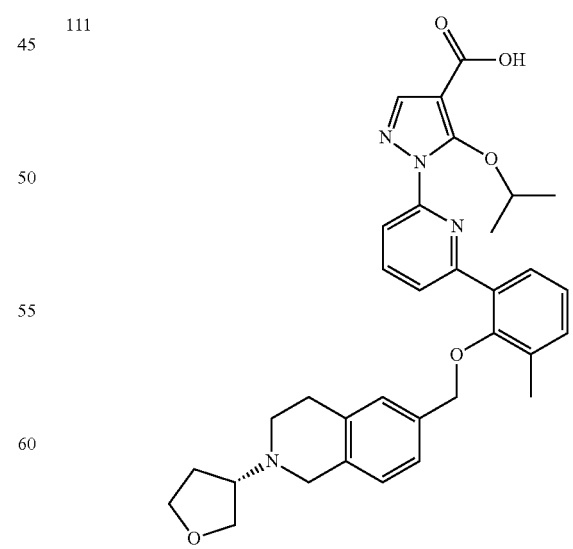 |
| 111 | 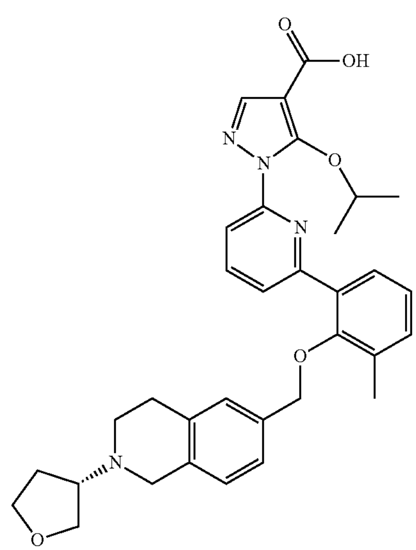 [SMILES: Cc1cccc(-c2cccc(-n3ncc(C(=O)O)c3OC(C)C)n2)c1OCc1ccc2c(c1)CCN([C@H]1CCOC1)C2] |

TABLE 1-continued
| Cpd No. | Structure |
|---|---|
| 112 | 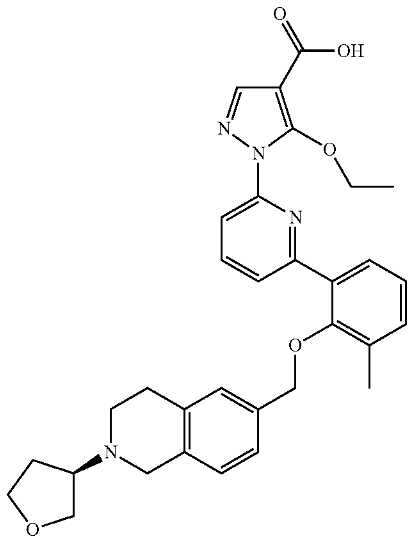 [SMILES: CCOc1c(C(=O)O)cnn1-c1cccc(-c2cccc(C)c2OCc2ccc3c(c2)CCN([C@@H]2CCOC2)C3)n1] |
| 114 | |
| 113 | 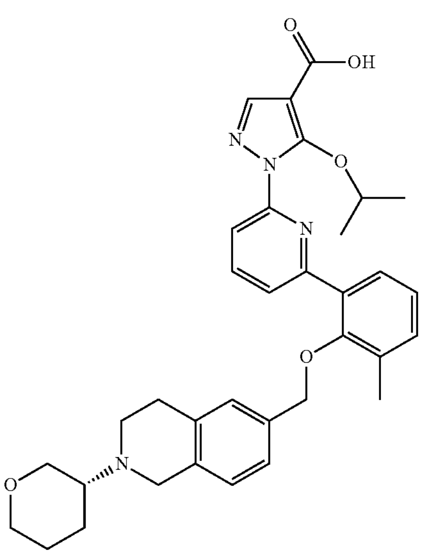 [SMILES: Cc1cccc(-c2cccc(-n3ncc(C(=O)O)c3OC(C)C)n2)c1OCc1ccc2c(c1)CCN([C@@H]1CCCOC1)C2] |
| 115 | |
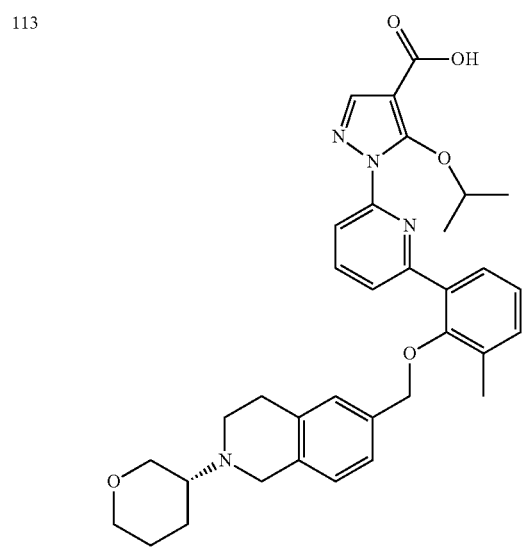
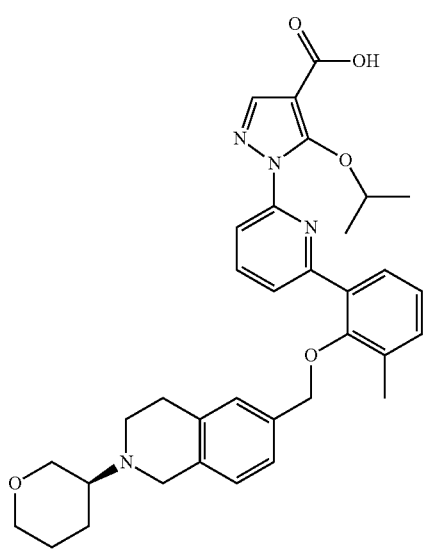 [SMILES: Cc1cccc(-c2cccc(-n3ncc(C(=O)O)c3OC(C)C)n2)c1OCc1ccc2c(c1)CCN([C@H]1CCCOC1)C2]

TABLE 1-continued

| Cpd No. | Structure |
|---|---|
| 116 | 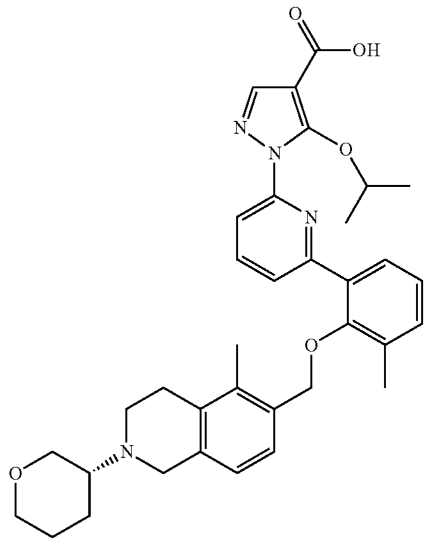 [SMILES: Cc1cccc(-c2cccc(-n3ncc(C(=O)O)c3OC(C)C)n2)c1OCc1ccc2c(c1C)CCN([C@@H]1CCCOC1)C2] |
| 117 | 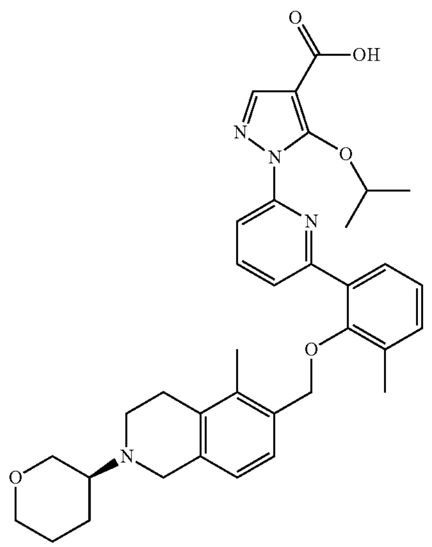 [SMILES: Cc1cccc(-c2cccc(-n3ncc(C(=O)O)c3OC(C)C)n2)c1OCc1ccc2c(c1C)CCN([C@H]1CCCOC1)C2] |
| 118 | 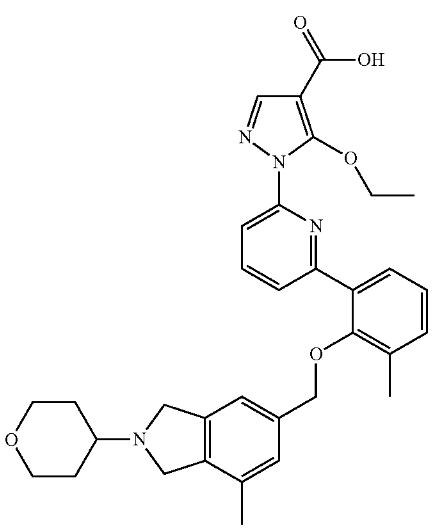 [SMILES: CCOc1c(C(=O)O)cnn1-c1cccc(-c2cccc(C)c2OCc2cc(C)c3c(c2)CN(C2CCOCC2)C3)n1] |
| 119 | |
| 120 | |
| 121 | |

TABLE 1-continued
| Cpd No. | Structure |
|---|---|
| 122 | 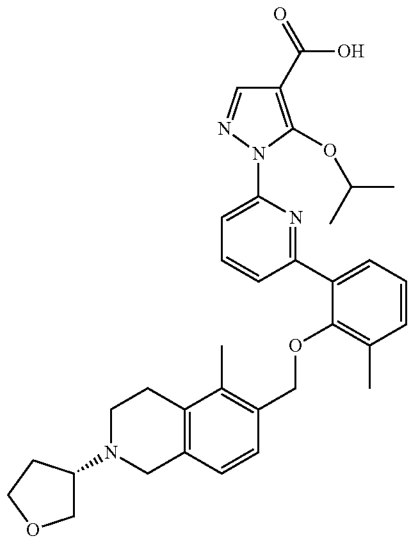 [SMILES: Cc1cccc(-c2cccc(-n3ncc(C(=O)O)c3OC(C)C)n2)c1OCc1ccc2c(c1C)CCN([C@H]1CCOC1)C2] |
| 123 | 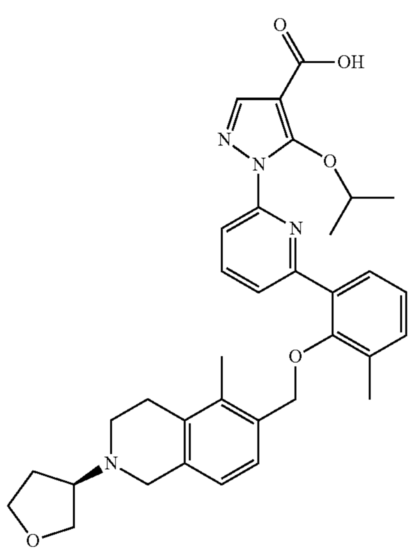 [SMILES: Cc1cccc(-c2cccc(-n3ncc(C(=O)O)c3OC(C)C)n2)c1OCc1ccc2c(c1C)CCN([C@@H]1CCOC1)C2] |
| 124 | |
| 125 | |
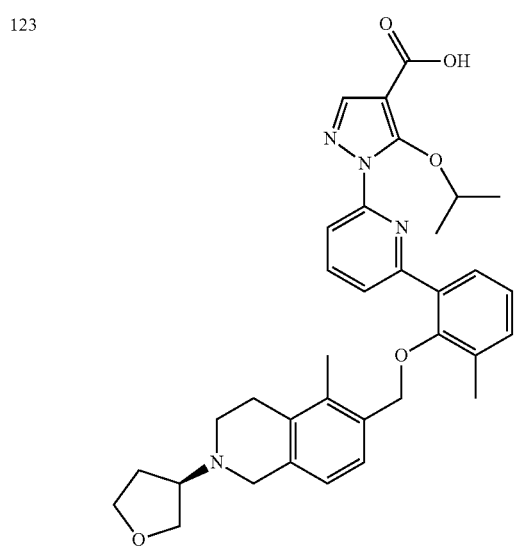
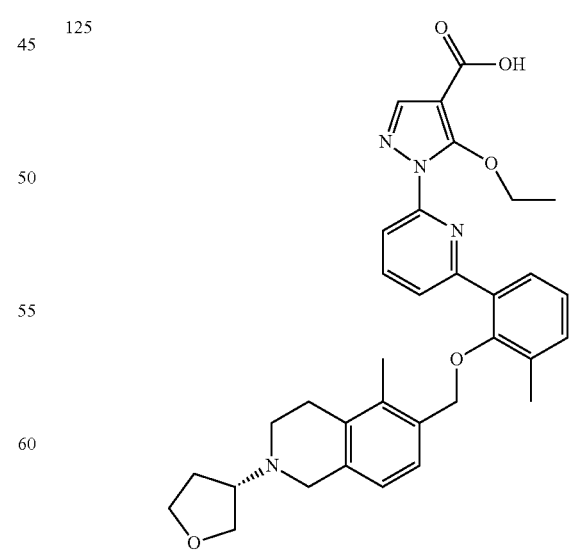

TABLE 1-continued

| Cpd No. | Structure |
|---|---|
| 126 | 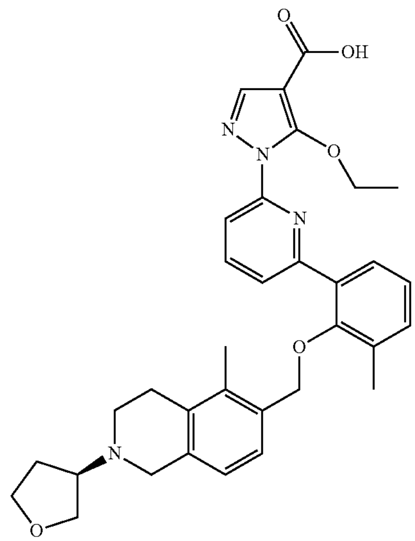 |
| 127 | 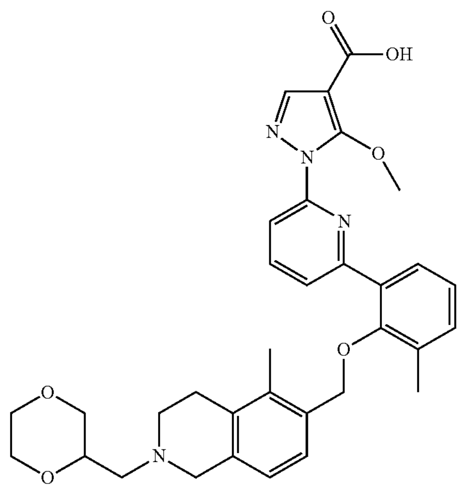 [SMILES: COc1c(C(=O)O)cnn1-c1cccc(-c2cccc(C)c2OCc2ccc3c(c2C)CCN(CC2COCCO2)C3)n1] |
| 128 | 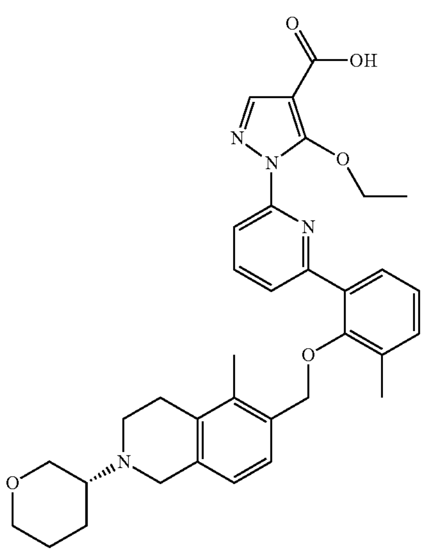 [SMILES: CCOc1c(C(=O)O)cnn1-c1cccc(-c2cccc(C)c2OCc2ccc3c(c2C)CCN([C@@H]2CCCOC2)C3)n1] |
| 129 | 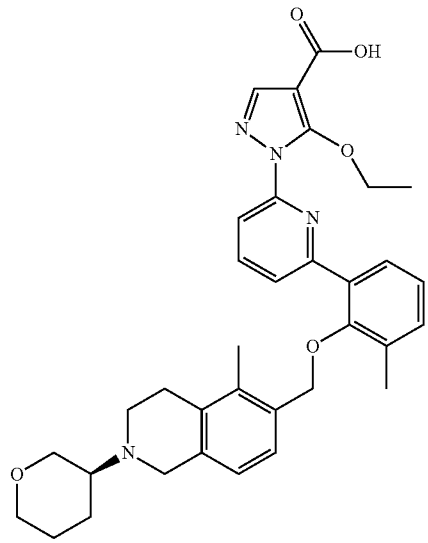 [SMILES: CCOc1c(C(=O)O)cnn1-c1cccc(-c2cccc(C)c2OCc2ccc3c(c2C)CCN([C@H]2CCCOC2)C3)n1] |
| 130 | 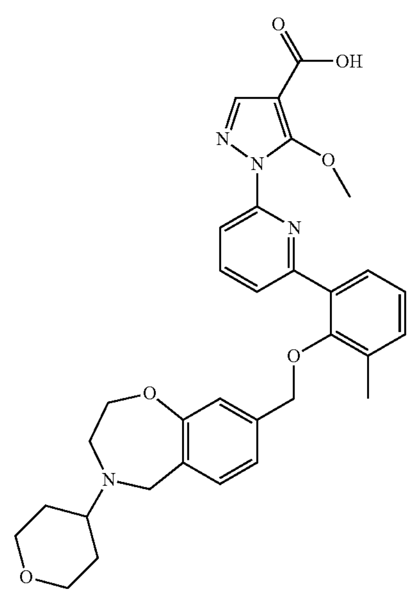 [SMILES: COc1c(C(=O)O)cnn1-c1cccc(-c2cccc(C)c2OCc2ccc3c(c2)OCCN(C2CCOCC2)C3)n1] |

TABLE 1-continued
| Cpd No. | Structure |
|---|---|
| 131 | 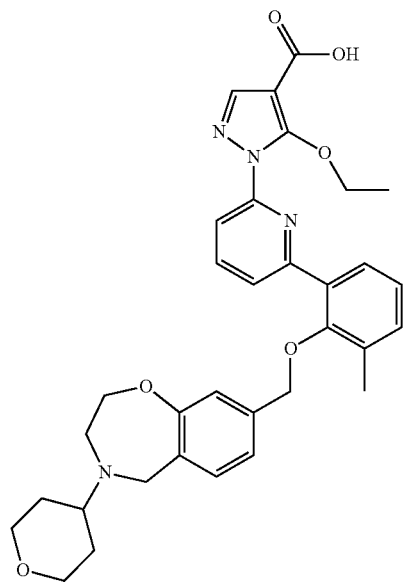 [SMILES: CCOc1c(C(=O)O)cnn1-c1cccc(-c2cccc(C)c2OCc2ccc3c(c2)OCCN(C2CCOCC2)C3)n1] |
| 132 | 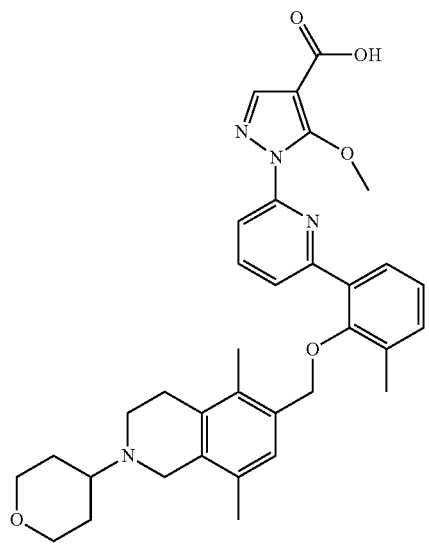 [SMILES: COc1c(C(=O)O)cnn1-c1cccc(-c2cccc(C)c2OCc2cc(C)c3c(c2C)CCN(C2CCOCC2)C3)n1] |
| 133 | 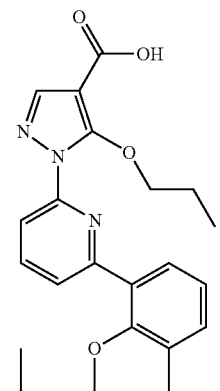 |
| 134 | 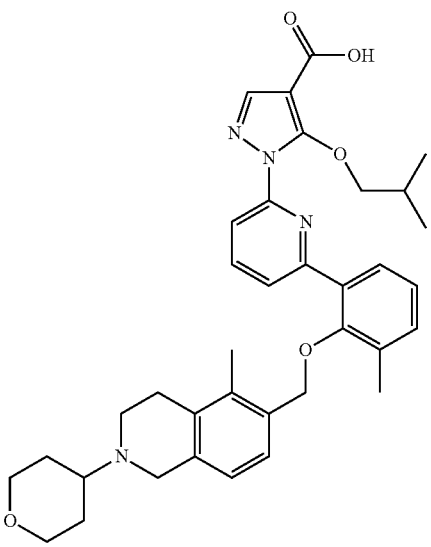 [SMILES: Cc1cccc(-c2cccc(-n3ncc(C(=O)O)c3OCC(C)C)n2)c1OCc1ccc2c(c1C)CCN(C1CCOCC1)C2] |

TABLE 1-continued
| Cpd No. | Structure |
|---|---|
| 135 | 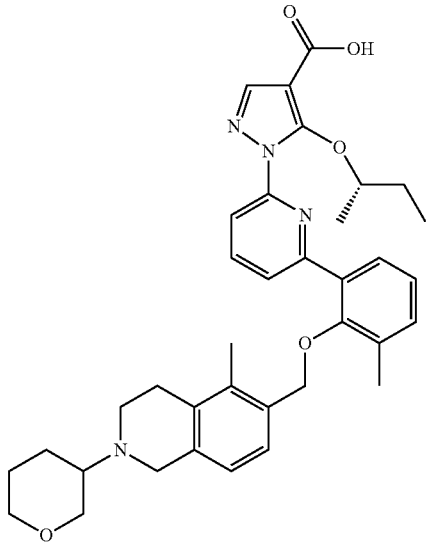 [SMILES: CC[C@H](C)Oc1c(C(=O)O)cnn1-c1cccc(-c2cccc(C)c2OCc2ccc3c(c2C)CCN(C2CCCOC2)C3)n1] |
| 136 | 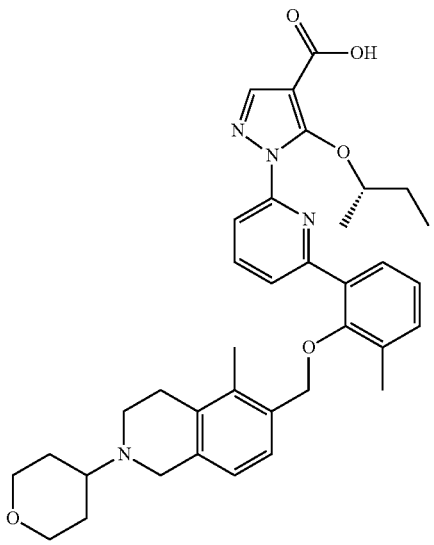 [SMILES: CC[C@H](C)Oc1c(C(=O)O)cnn1-c1cccc(-c2cccc(C)c2OCc2ccc3c(c2C)CCN(C2CCOCC2)C3)n1] |
| 137 | 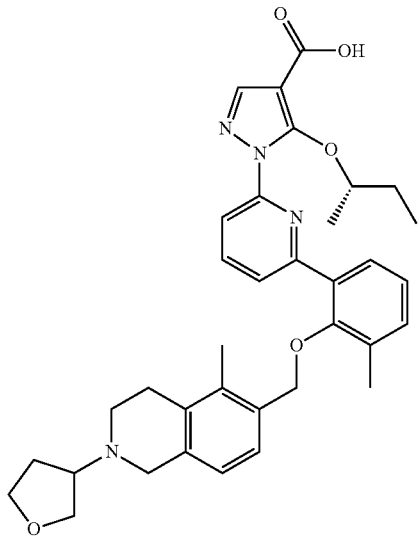 [SMILES: CC[C@H](C)Oc1c(C(=O)O)cnn1-c1cccc(-c2cccc(C)c2OCc2ccc3c(c2C)CCN(C2CCOC2)C3)n1] |
| 138 | 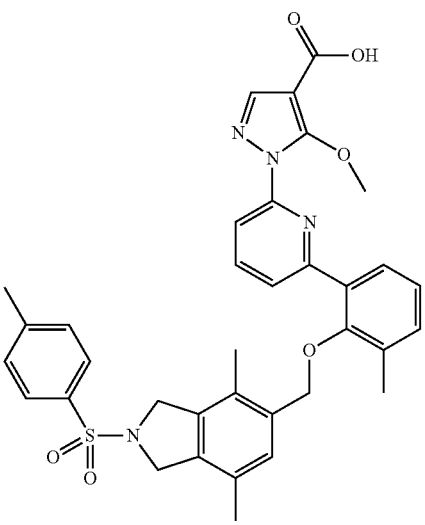 [SMILES: COc1c(C(=O)O)cnn1-c1cccc(-c2cccc(C)c2OCc2cc(C)c3c(c2C)CN(S(=O)(=O)c2ccc(C)cc2)C3)n1] |
| 139 | 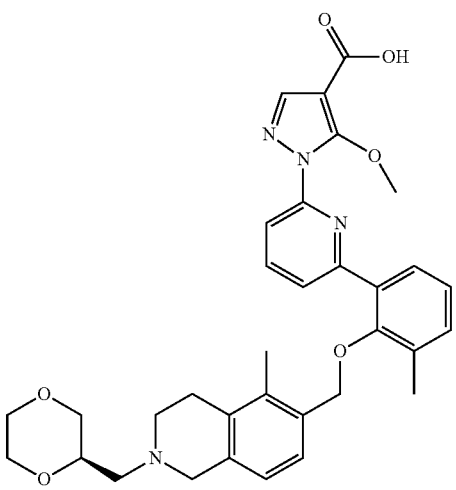 [SMILES: COc1c(C(=O)O)cnn1-c1cccc(-c2cccc(C)c2OCc2ccc3c(c2C)CCN(C[C@@H]2COCCO2)C3)n1] |

TABLE 1-continued

| Cpd No. | Structure |
|---|---|
| 140 | 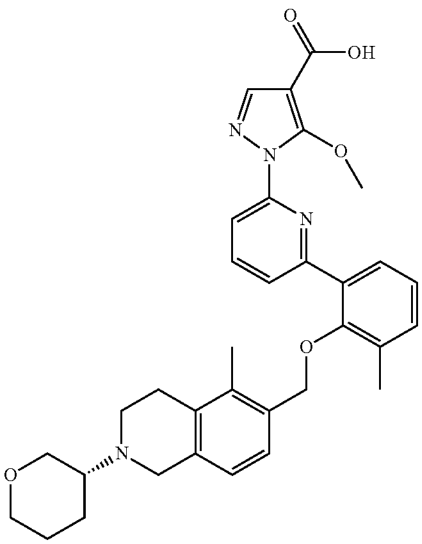 |
| 141 | 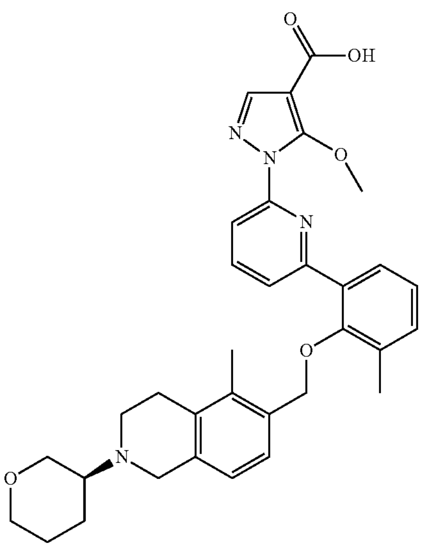 [SMILES: COc1c(C(=O)O)cnn1-c1cccc(-c2cccc(C)c2OCc2ccc3c(c2C)CCN([C@H]2CCCOC2)C3)n1] |
| 142 | 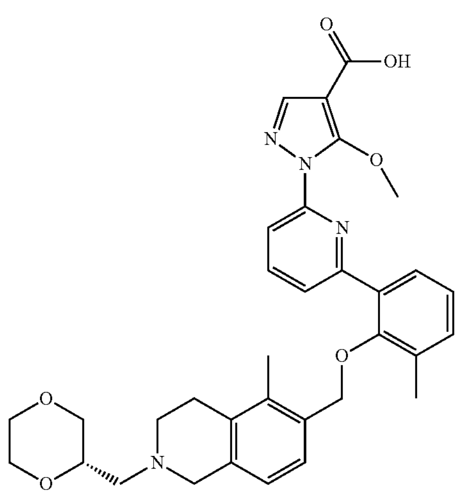 [SMILES: COc1c(C(=O)O)cnn1-c1cccc(-c2cccc(C)c2OCc2ccc3c(c2C)CCN(C[C@H]2COCCO2)C3)n1] |
| 143 | |
| 144 | |
| 145 | |

TABLE 1-continued

| Cpd No. | Structure |
|---|---|
| 146 | 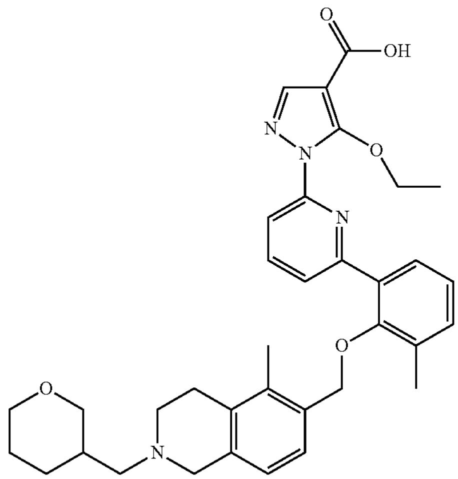 [SMILES: CCOc1c(C(=O)O)cnn1-c1cccc(-c2cccc(C)c2OCc2ccc3c(c2C)CCN(CC2CCCOC2)C3)n1] |
| 147 | 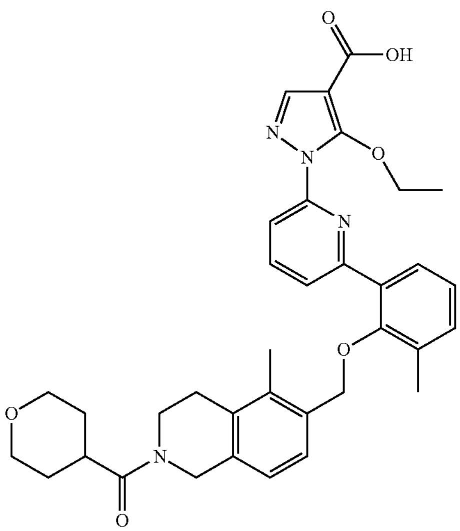 [SMILES: CCOc1c(C(=O)O)cnn1-c1cccc(-c2cccc(C)c2OCc2ccc3c(c2C)CCN(C(=O)C2CCOCC2)C3)n1] |
| 148 | 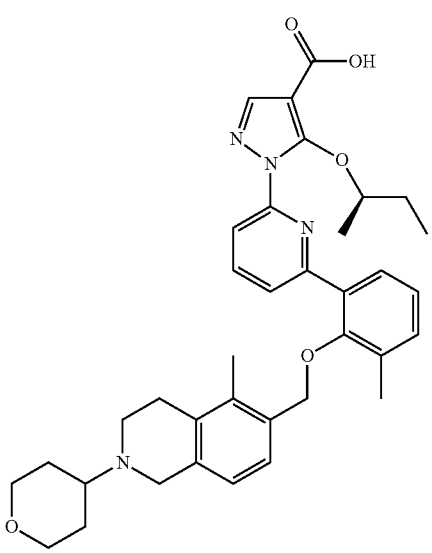 [SMILES: CC[C@@H](C)Oc1c(C(=O)O)cnn1-c1cccc(-c2cccc(C)c2OCc2ccc3c(c2C)CCN(C2CCOCC2)C3)n1] |
| 149 | |
| 150 | |

TABLE 1-continued

| Cpd No. | Structure |
|---|---|
| 151 | 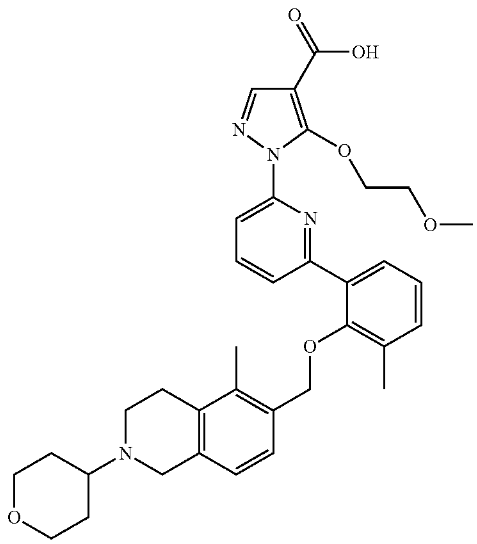 [SMILES: COCCOc1c(C(=O)O)cnn1-c1cccc(-c2cccc(C)c2OCc2ccc3c(c2C)CCN(C2CCOCC2)C3)n1] |
| 152 | 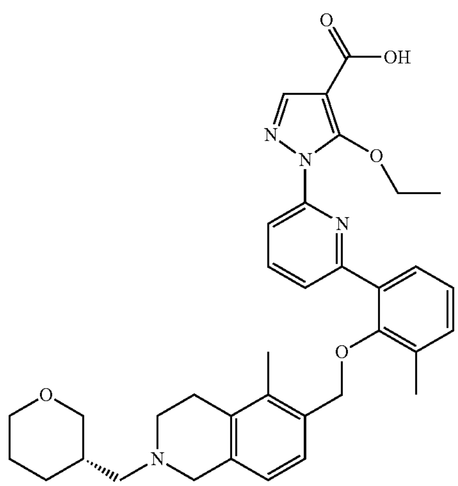 [SMILES: CCOc1c(C(=O)O)cnn1-c1cccc(-c2cccc(C)c2OCc2ccc3c(c2C)CCN(C[C@@H]2CCCOC2)C3)n1] |
| 153 | 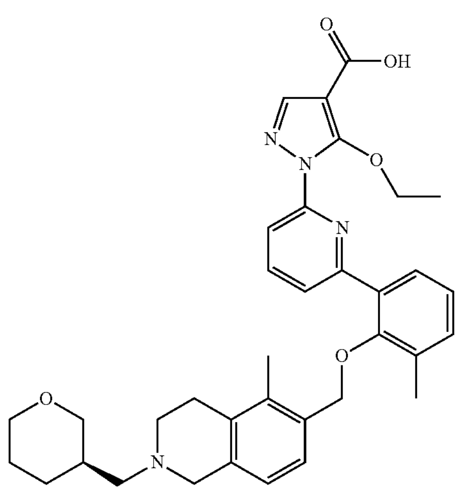 [SMILES: CCOc1c(C(=O)O)cnn1-c1cccc(-c2cccc(C)c2OCc2ccc3c(c2C)CCN(C[C@H]2CCCOC2)C3)n1] |
| 154 | 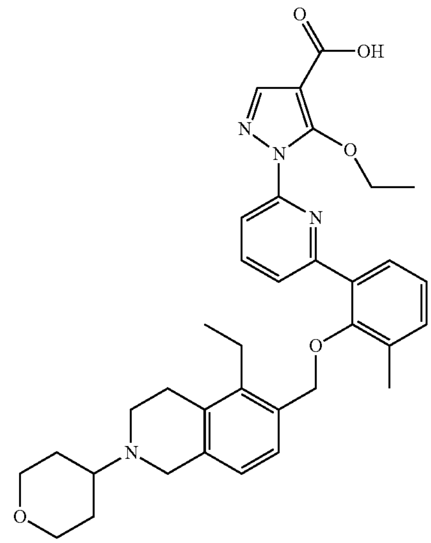 [SMILES: CCOc1c(C(=O)O)cnn1-c1cccc(-c2cccc(C)c2OCc2ccc3c(c2CC)CCN(C2CCOCC2)C3)n1] |
| 155 | 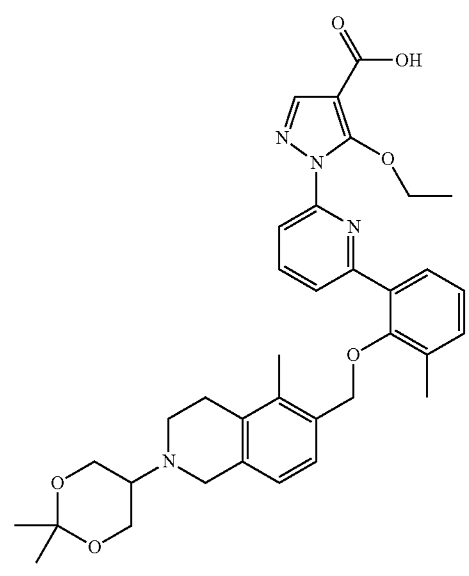 [SMILES: CCOc1c(C(=O)O)cnn1-c1cccc(-c2cccc(C)c2OCc2ccc3c(c2C)CCN(C2COC(C)(C)OC2)C3)n1] |

TABLE 1-continued

| Cpd No. | Structure |
|---|---|
| 156 | (structure) |
| 157 | (structure) |
| 158 | (structure) |
| 159 | (structure) |
| 160 | (structure) |

TABLE 1-continued
| Cpd No. | Structure |
|---|---|
| 161 | 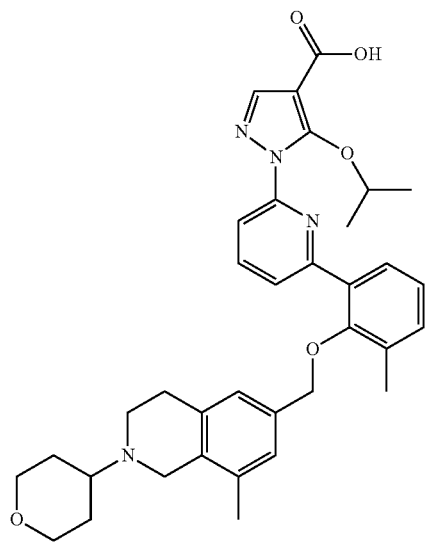 [SMILES: Cc1cc(COc2c(C)cccc2-c2cccc(-n3ncc(C(=O)O)c3OC(C)C)n2)cc2c1CN(C1CCOCC1)CC2] |
| 162 | 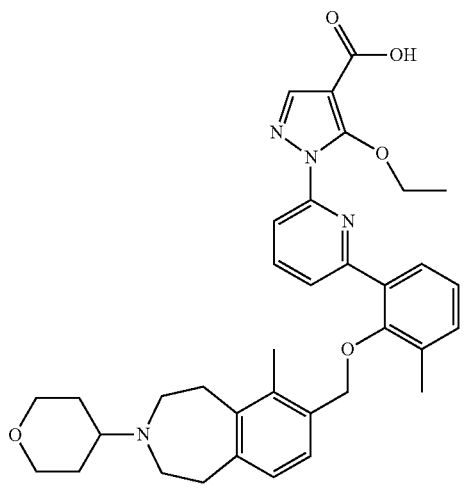 [SMILES: CCOc1c(C(=O)O)cnn1-c1cccc(-c2cccc(C)c2OCc2ccc3c(c2C)CCN(C2CCOCC2)CC3)n1] |
| 163 | 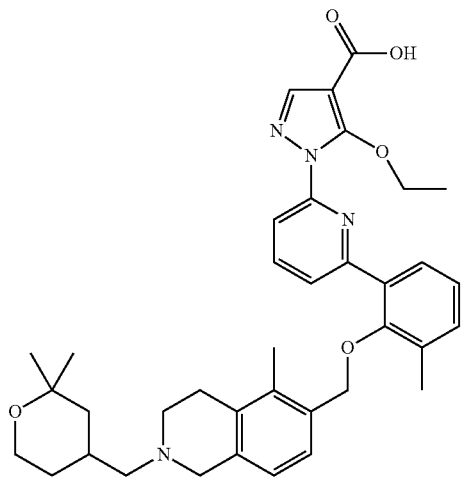 [SMILES: CCOc1c(C(=O)O)cnn1-c1cccc(-c2cccc(C)c2OCc2ccc3c(c2C)CCN(CC2CCOC(C)(C)C2)C3)n1] |
| 164 | 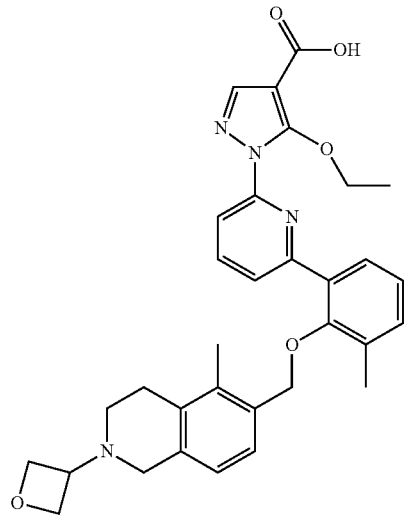 [SMILES: CCOc1c(C(=O)O)cnn1-c1cccc(-c2cccc(C)c2OCc2ccc3c(c2C)CCN(C2COC2)C3)n1] |
| 165 | 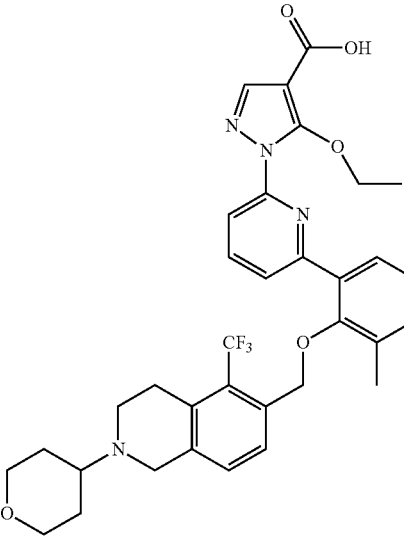 |
| 166 | 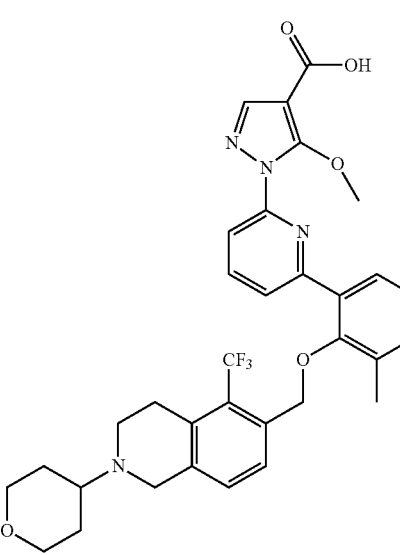 |

TABLE 1-continued

| Cpd No. | Structure |
|---|---|
| 167 | *(chemical structure)* |
| 168 | *(chemical structure)* |
| 169 | *(chemical structure)* |
| 170 | *(chemical structure)* |
| 171 | *(chemical structure)* |
| 172 | *(chemical structure)* |

TABLE 1-continued

| Cpd No. | Structure |
|---|---|
| 173 | 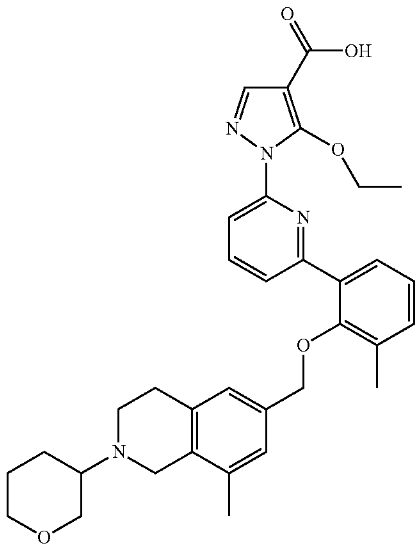 [SMILES: CCOc1c(C(=O)O)cnn1-c1cccc(-c2cccc(C)c2OCc2cc(C)c3c(c2)CCN(C2CCCOC2)C3)n1] |
| 174 | 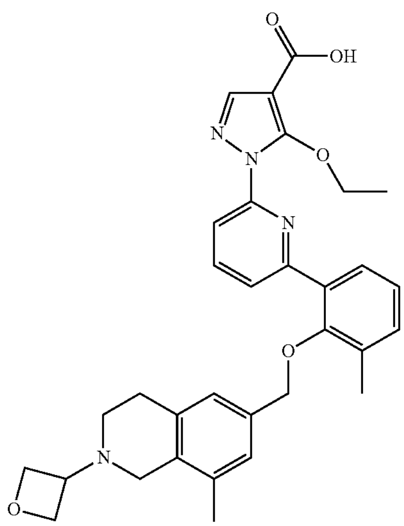 [SMILES: CCOc1c(C(=O)O)cnn1-c1cccc(-c2cccc(C)c2OCc2cc(C)c3c(c2)CCN(C2COC2)C3)n1] |
| 175 | 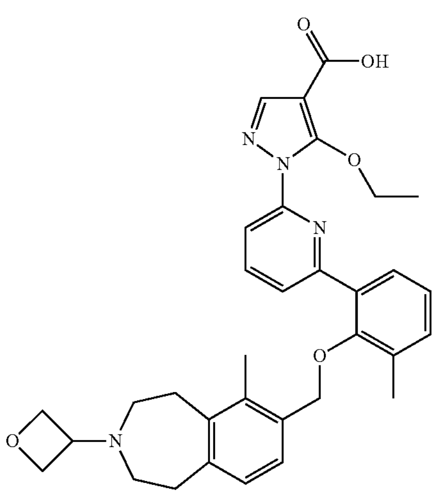 |
| 176 | |
| 177 | |
| 178 | |

TABLE 1-continued
| Cpd No. | Structure |
|---|---|
| 179 | 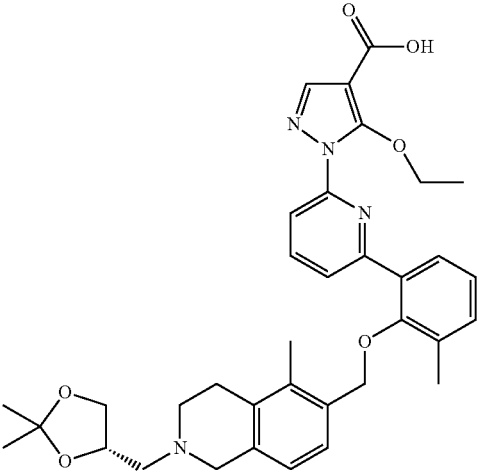 [SMILES: CCOc1c(C(=O)O)cnn1-c1cccc(-c2cccc(C)c2OCc2ccc3c(c2C)CCN(C[C@H]2COC(C)(C)O2)C3)n1] |
| 180 | 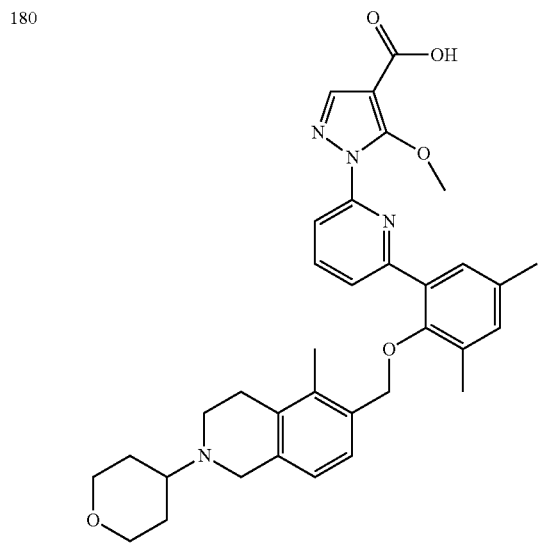 |
| 181 | 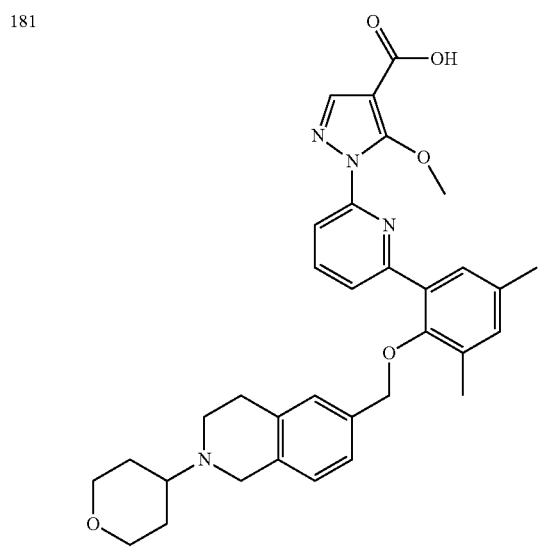 |//
TABLE 1-continued
| Cpd No. | Structure |
|---|---|
| 182 | 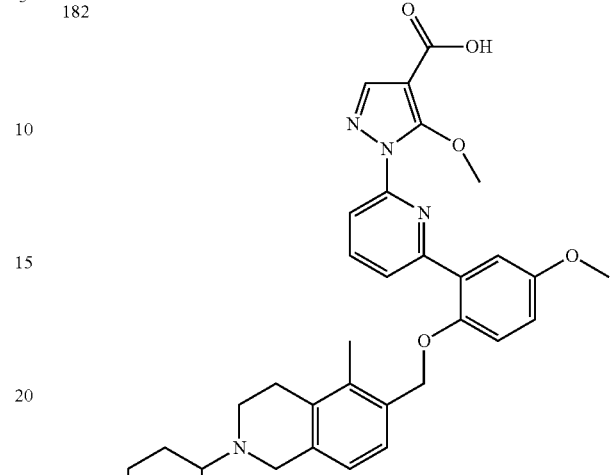 |
| 183 | 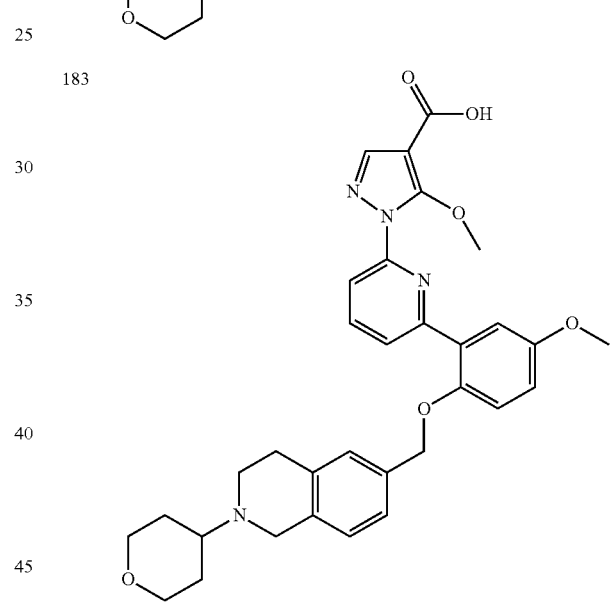 |
| 184 | 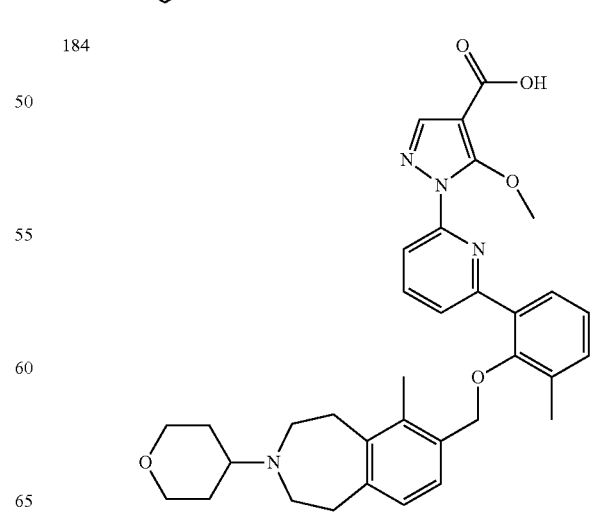 |

TABLE 1-continued
| Cpd No. | Structure |
|---|---|
| 185 | 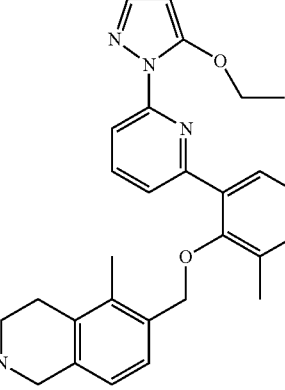 |
| 186 | 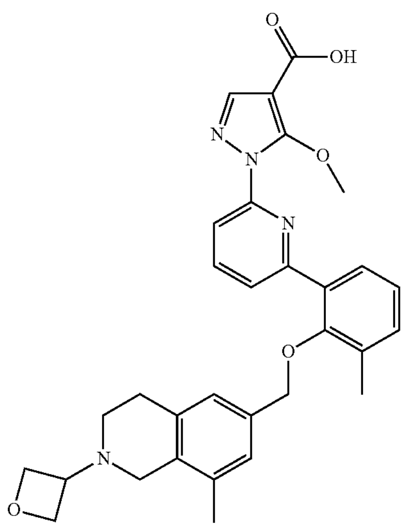 [SMILES: COc1c(C(=O)O)cnn1-c1cccc(-c2cccc(C)c2OCc2cc(C)c3c(c2)CCN(C2COC2)C3)n1] |
| 187 | 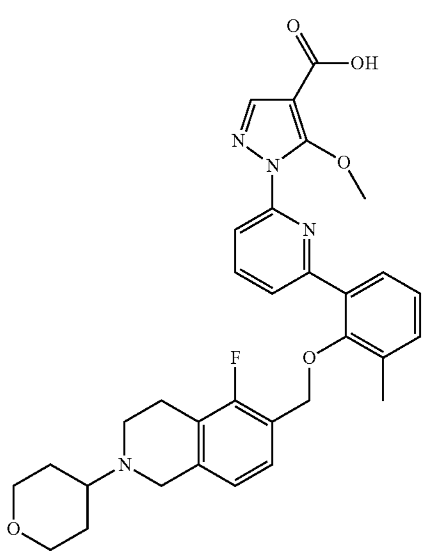 [SMILES: COc1c(C(=O)O)cnn1-c1cccc(-c2cccc(C)c2OCc2ccc3c(c2F)CCN(C2CCOCC2)C3)n1] |
| 188 | 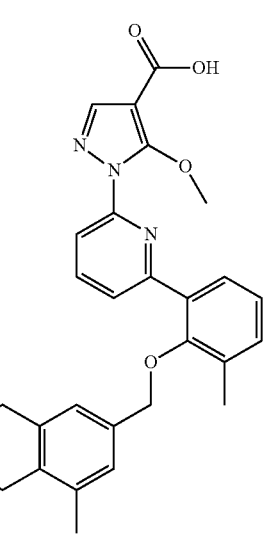 |
| 189 | |
| 190 | |

TABLE 1-continued
| Cpd No. | Structure |
|---|---|
| 191 | 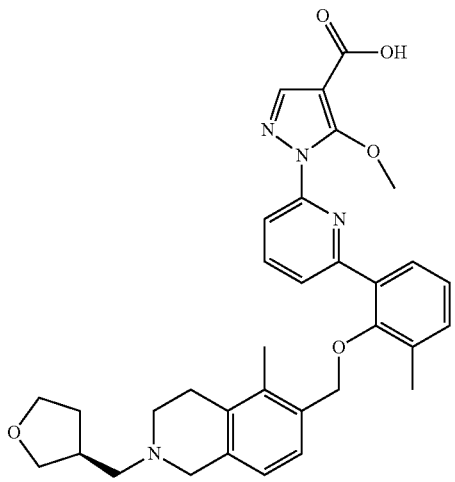 [SMILES: COc1c(C(=O)O)cnn1-c1cccc(-c2cccc(C)c2OCc2ccc3c(c2C)CCN(C[C@@H]2CCOC2)C3)n1] |
| 192 | 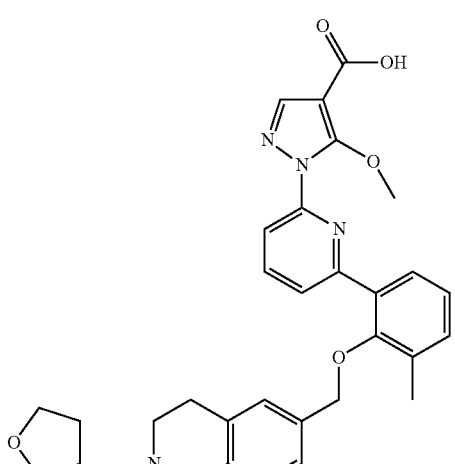 |
| 193 | 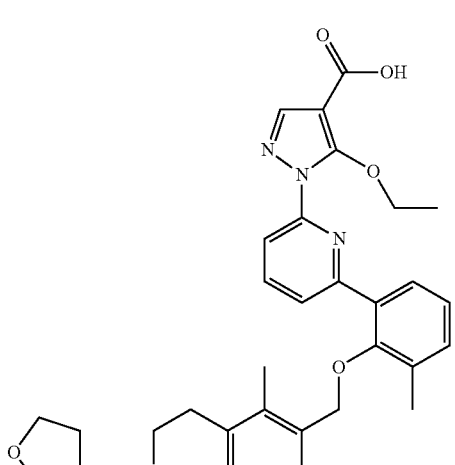 |
| 194 | 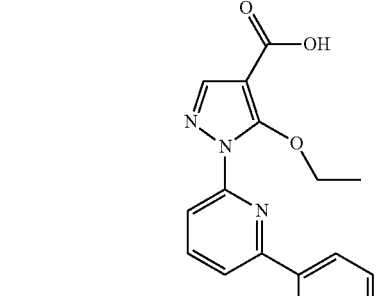 |
| 195 | 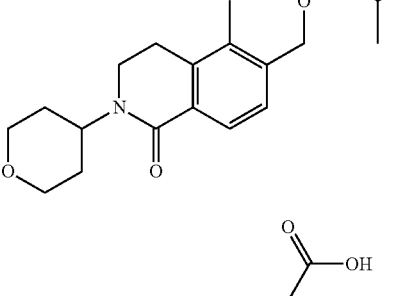 |
| 196 | 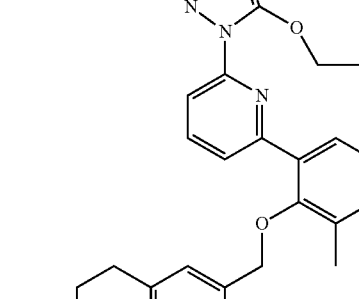 |

TABLE 1-continued
| Cpd No. | Structure |
|---|---|
| 197 | 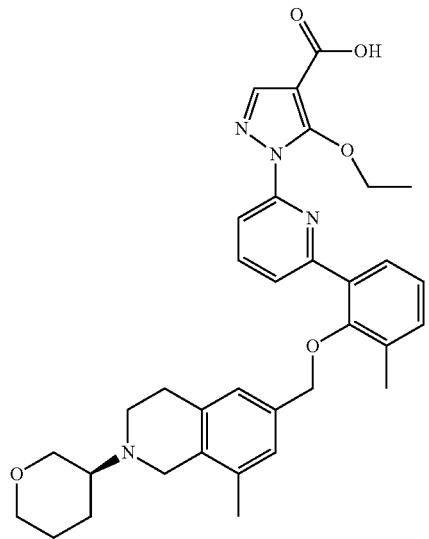 [SMILES: CCOc1c(C(=O)O)cnn1-c1cccc(-c2cccc(C)c2OCc2cc(C)c3c(c2)CCN([C@H]2CCCOC2)C3)n1] |
| 198 | 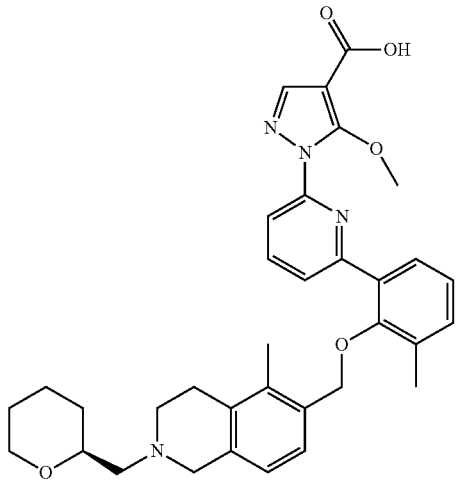 [SMILES: COc1c(C(=O)O)cnn1-c1cccc(-c2cccc(C)c2OCc2ccc3c(c2C)CCN(C[C@@H]2CCCCO2)C3)n1] |
| 199 | 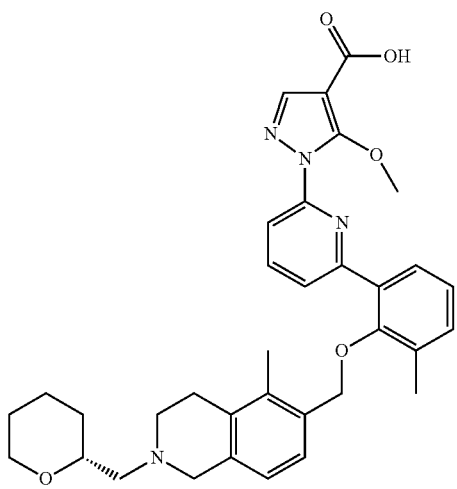 |
| 200 | 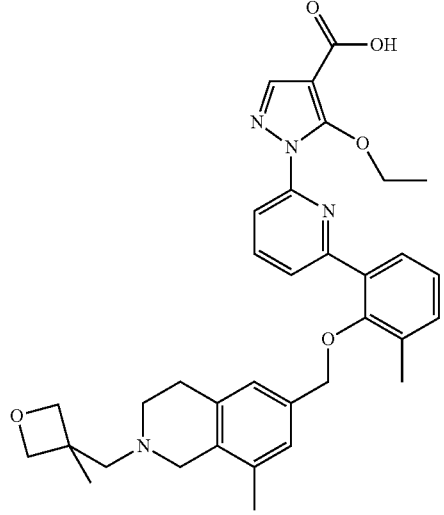 [SMILES: CCOc1c(C(=O)O)cnn1-c1cccc(-c2cccc(C)c2OCc2cc(C)c3c(c2)CCN(CC2(C)COC2)C3)n1] |
| 201 | 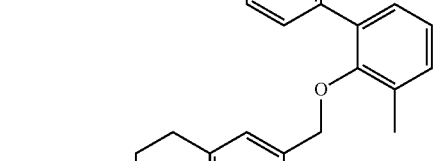 |
| 202 | 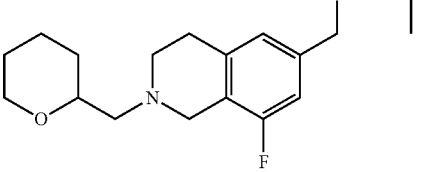 |

TABLE 1-continued

| Cpd No. | Structure |
|---|---|
| 203 | 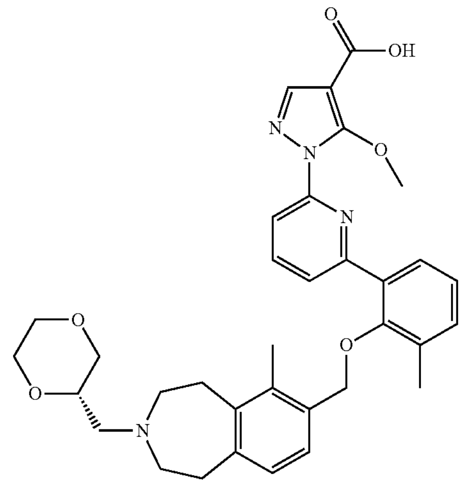 [SMILES: COc1c(C(=O)O)cnn1-c1cccc(-c2cccc(C)c2OCc2ccc3c(c2C)CCN(C[C@H]2COCCO2)CC3)n1] |
| 204 | 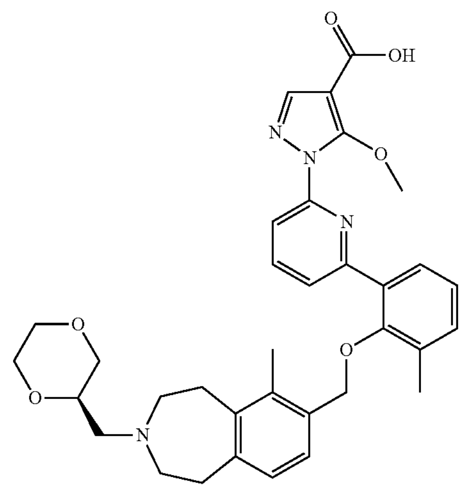 [SMILES: COc1c(C(=O)O)cnn1-c1cccc(-c2cccc(C)c2OCc2ccc3c(c2C)CCN(C[C@@H]2COCCO2)CC3)n1] |
| 205 | 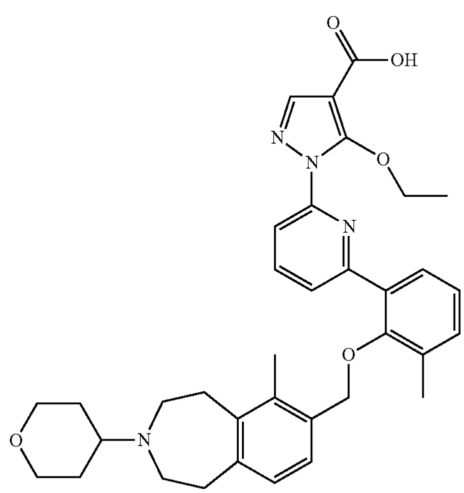 [SMILES: CCOc1c(C(=O)O)cnn1-c1cccc(-c2cccc(C)c2OCc2ccc3c(c2C)CCN(C2CCOCC2)CC3)n1] |
| 206 | |
| 207 | |
| 208 | |

TABLE 1-continued
| Cpd No. | Structure |
|---|---|
| 209 | 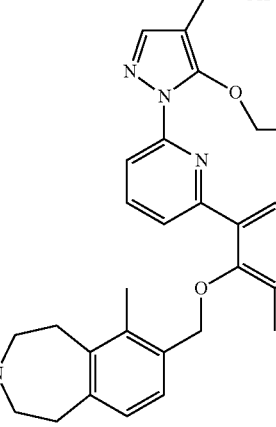 |
| 210 | 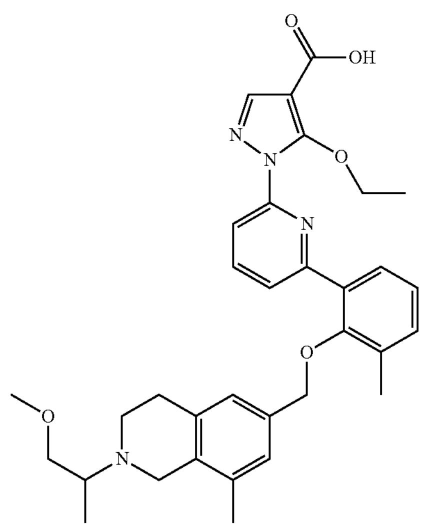 [SMILES: CCOc1c(C(=O)O)cnn1-c1cccc(-c2cccc(C)c2OCc2cc(C)c3c(c2)CCN(C(C)COC)C3)n1] |
| 211 | 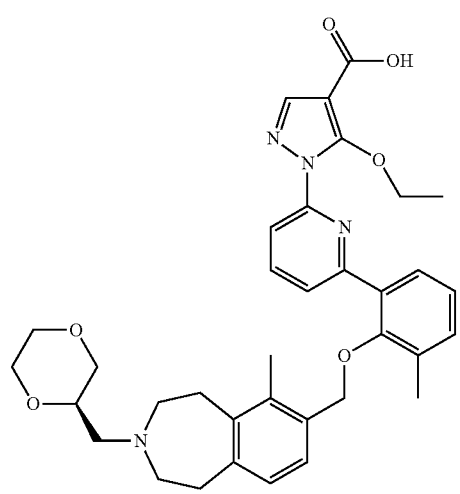 |
TABLE 1-continued
| Cpd No. | Structure |
|---|---|
| 212 | 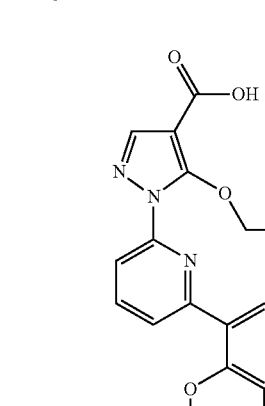 |
| 213 | 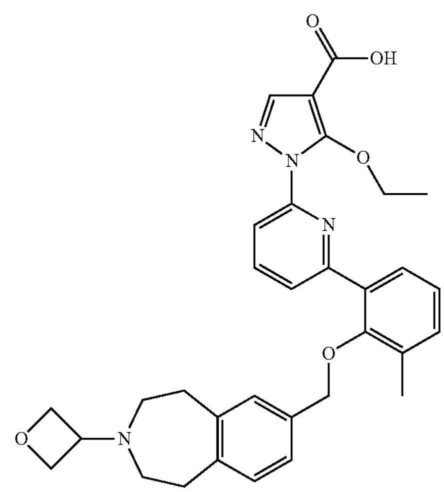 |
| 214 | 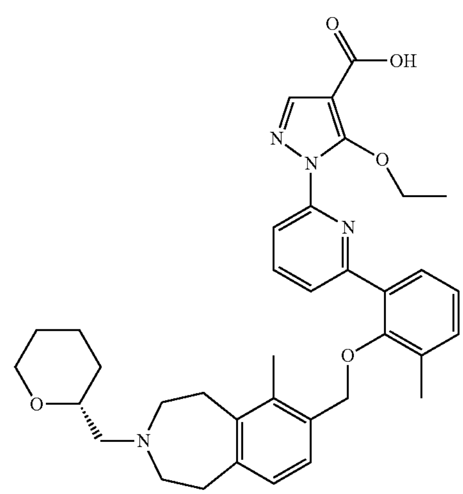 [SMILES: CCOc1c(C(=O)O)cnn1-c1cccc(-c2cccc(C)c2OCc2ccc3c(c2C)CCN(C[C@H]2COCCO2)CC3)n1] |

TABLE 1-continued

| Cpd No. | Structure |
|---|---|
| 215 | 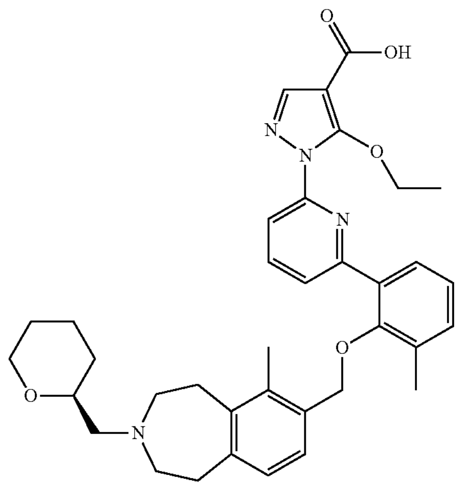 [SMILES: CCOc1c(C(=O)O)cnn1-c1cccc(-c2cccc(C)c2OCc2ccc3c(c2C)CCN(C[C@@H]2CCCCO2)CC3)n1] |
| 216 | 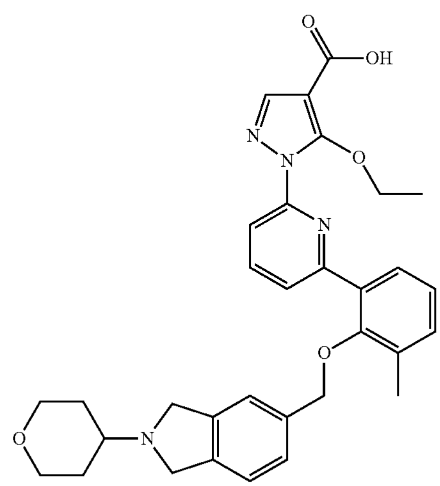 [SMILES: CCOc1c(C(=O)O)cnn1-c1cccc(-c2cccc(C)c2OCc2ccc3c(c2)CN(C2CCOCC2)C3)n1] |
| 217 | 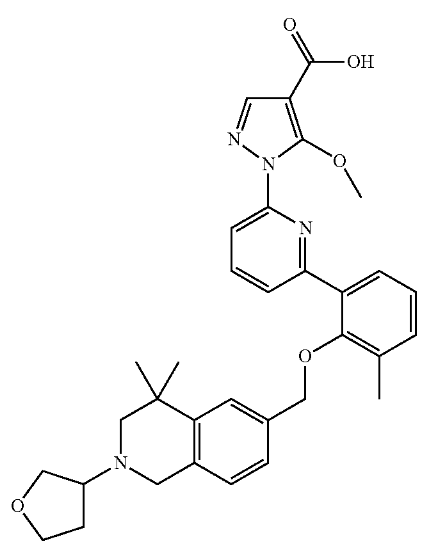 [SMILES: COc1c(C(=O)O)cnn1-c1cccc(-c2cccc(C)c2OCc2ccc3c(c2)C(C)(C)CN(C2CCOC2)C3)n1] |
| 218 | |
| 219 | |
| 220 | |

TABLE 1-continued

| Cpd No. | Structure |
|---|---|
| 221 | 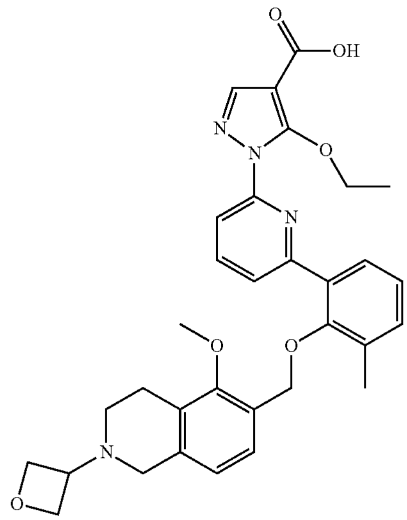 [SMILES: CCOc1c(C(=O)O)cnn1-c1cccc(-c2cccc(C)c2OCc2ccc3c(c2OC)CCN(C2COC2)C3)n1] |
| 222 | 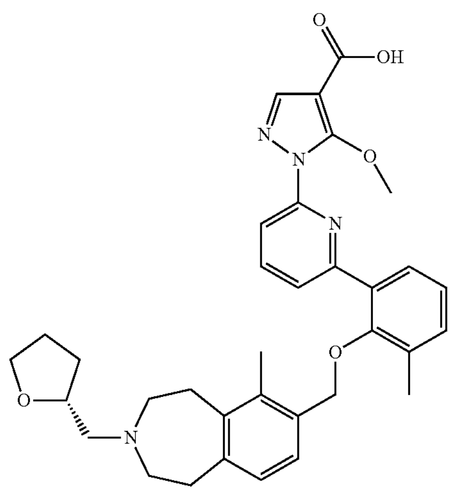 [SMILES: COc1c(C(=O)O)cnn1-c1cccc(-c2cccc(C)c2OCc2ccc3c(c2C)CCN(C[C@H]2CCCO2)CC3)n1] |
| 223 | 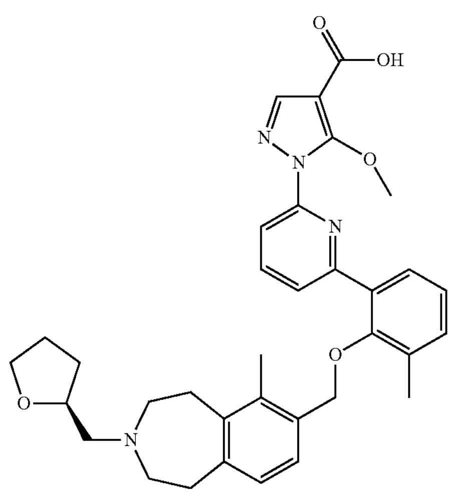 [SMILES: COc1c(C(=O)O)cnn1-c1cccc(-c2cccc(C)c2OCc2ccc3c(c2C)CCN(C[C@@H]2CCCO2)CC3)n1] |
| 224 | |
| 225 | |
| 226 | |

TABLE 1-continued

| Cpd No. | Structure |
|---|---|
| 227 | 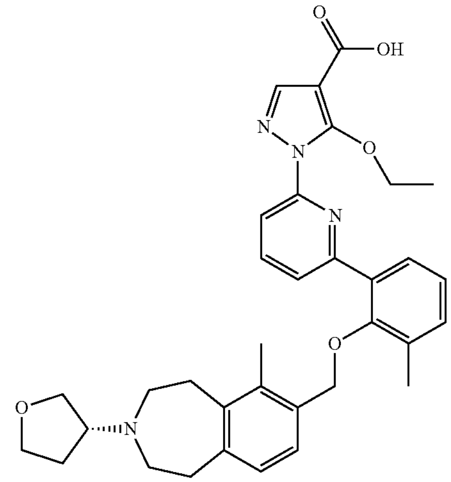 [SMILES: CCOc1c(C(=O)O)cnn1-c1cccc(-c2cccc(C)c2OCc2ccc3c(c2C)CCN([C@@H]2CCOC2)CC3)n1] |
| 228 | 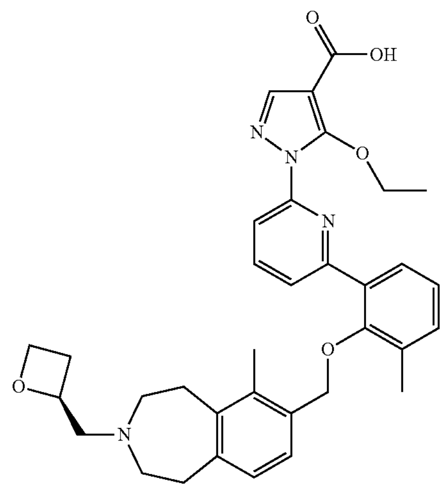 [SMILES: CCOc1c(C(=O)O)cnn1-c1cccc(-c2cccc(C)c2OCc2ccc3c(c2C)CCN(C[C@@H]2CCO2)CC3)n1] |
| 229 | 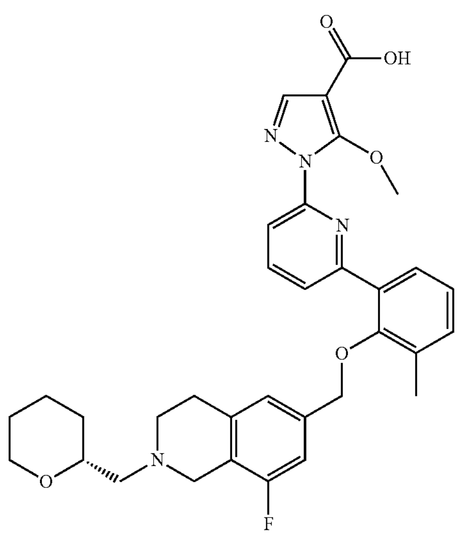 [SMILES: COc1c(C(=O)O)cnn1-c1cccc(-c2cccc(C)c2OCc2cc(F)c3c(c2)CCN(C[C@H]2CCCCO2)C3)n1] |
| 230 | 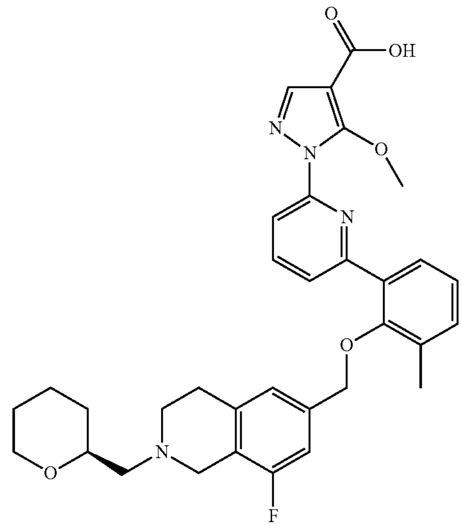 [SMILES: COc1c(C(=O)O)cnn1-c1cccc(-c2cccc(C)c2OCc2cc(F)c3c(c2)CCN(C[C@@H]2CCCCO2)C3)n1] |
| 231 | 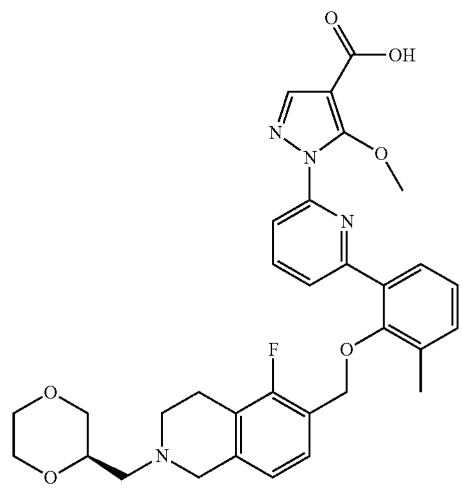 [SMILES: COc1c(C(=O)O)cnn1-c1cccc(-c2cccc(C)c2OCc2ccc3c(c2F)CCN(C[C@@H]2COCCO2)C3)n1] |
| 232 | 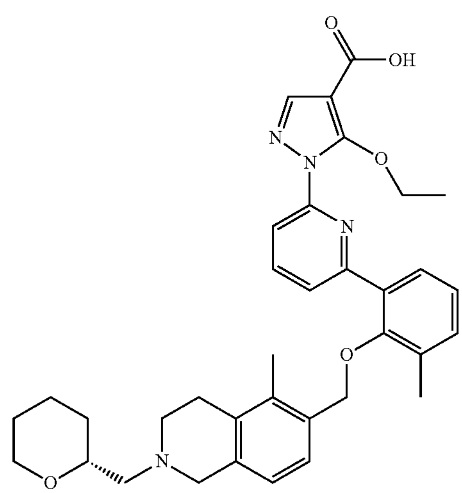 |

TABLE 1-continued

| Cpd No. | Structure |
|---|---|
| 233 | 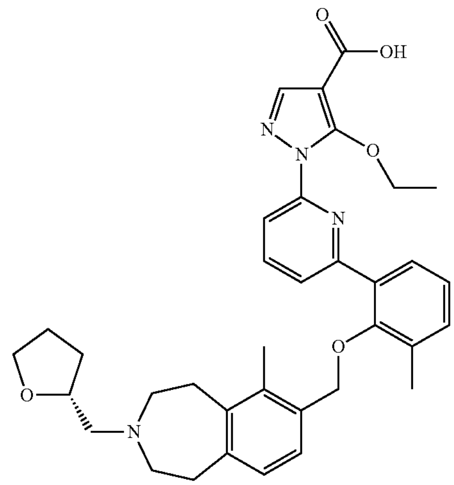 [SMILES: CCOc1c(C(=O)O)cnn1-c1cccc(-c2cccc(C)c2OCc2ccc3c(c2C)CCN(C[C@H]2CCCO2)CC3)n1] |
| 234 | 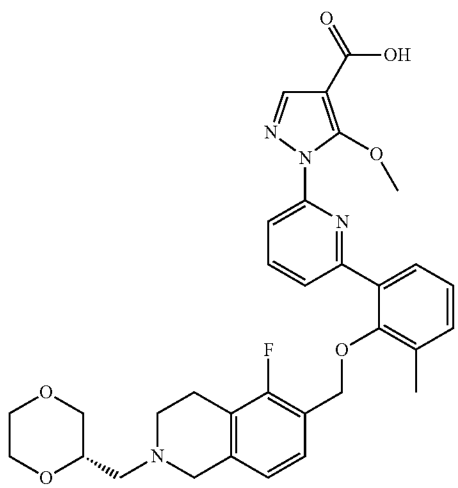 [SMILES: COc1c(C(=O)O)cnn1-c1cccc(-c2cccc(C)c2OCc2ccc3c(c2F)CCN(C[C@H]2COCCO2)C3)n1] |
| 235 | 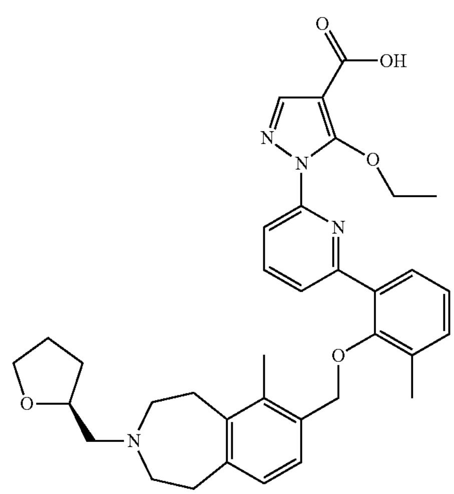 [SMILES: CCOc1c(C(=O)O)cnn1-c1cccc(-c2cccc(C)c2OCc2ccc3c(c2C)CCN(C[C@@H]2CCCO2)CC3)n1] |
| 236 | |
| 237 | |
| 238 | |

TABLE 1-continued
| Cpd No. | Structure |
|---|---|
| 239 | 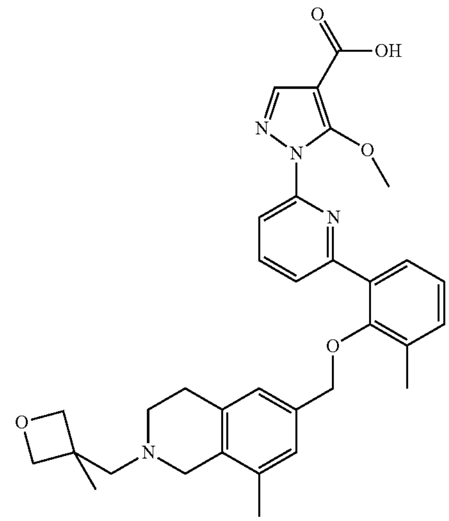 [SMILES: COc1c(C(=O)O)cnn1-c1cccc(-c2cccc(C)c2OCc2cc(C)c3c(c2)CCN(CC2(C)COC2)C3)n1] |
| 240 | 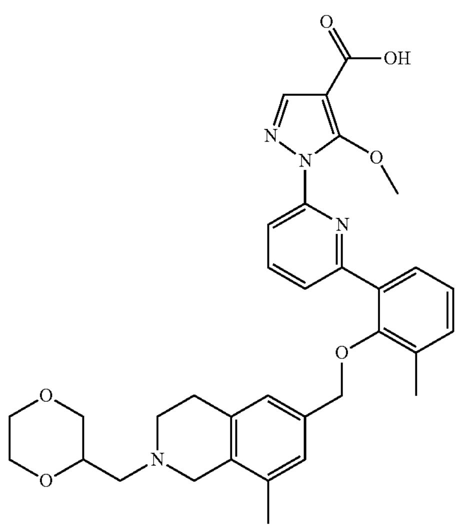 [SMILES: COc1c(C(=O)O)cnn1-c1cccc(-c2cccc(C)c2OCc2cc(C)c3c(c2)CCN(CC2COCCO2)C3)n1] |
| 241 | 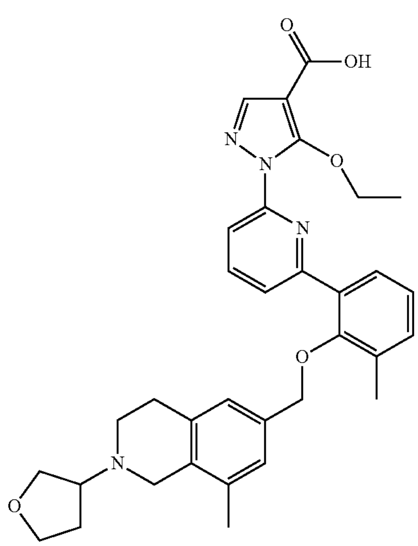 [SMILES: CCOc1c(C(=O)O)cnn1-c1cccc(-c2cccc(C)c2OCc2cc(C)c3c(c2)CCN(C2CCOC2)C3)n1] |
| 242 | 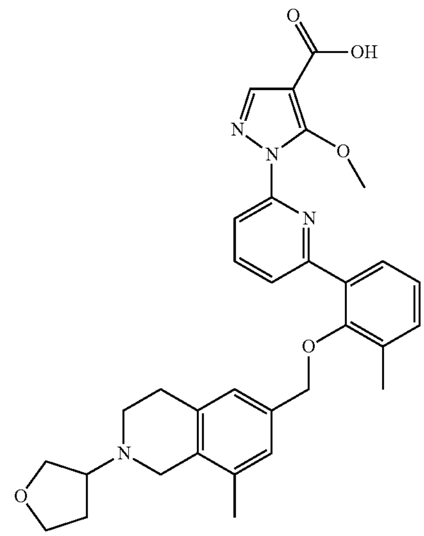 [SMILES: COc1c(C(=O)O)cnn1-c1cccc(-c2cccc(C)c2OCc2cc(C)c3c(c2)CCN(C2CCOC2)C3)n1] |
| 243 | 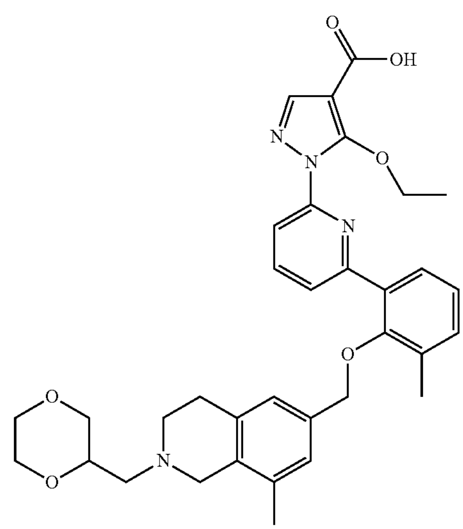 [SMILES: CCOc1c(C(=O)O)cnn1-c1cccc(-c2cccc(C)c2OCc2cc(C)c3c(c2)CCN(CC2COCCO2)C3)n1] |
| 244 | 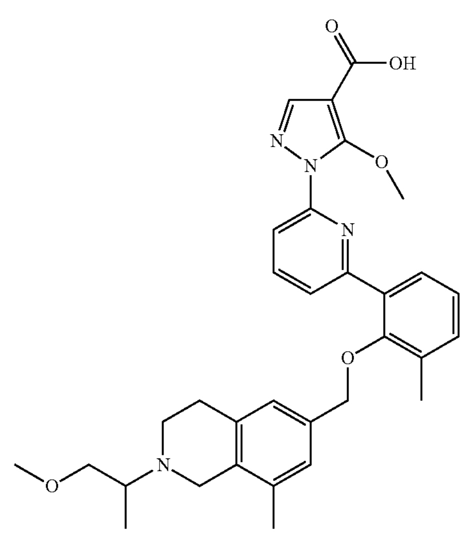 [SMILES: COCC(C)N1CCc2cc(COc3c(C)cccc3-c3cccc(-n4ncc(C(=O)O)c4OC)n3)cc(C)c2C1] |

TABLE 1-continued

| Cpd No. | Structure |
|---|---|
| 245 | 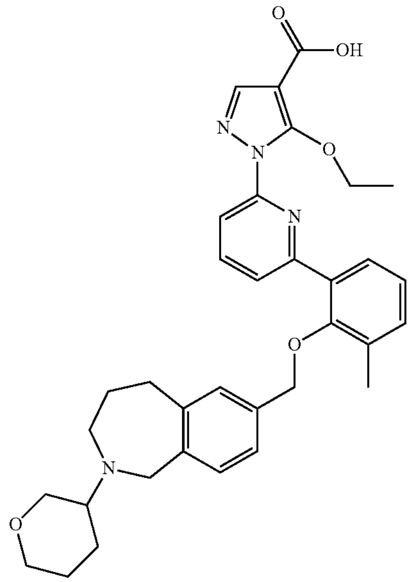 [SMILES: CCOc1c(C(=O)O)cnn1-c1cccc(-c2cccc(C)c2OCc2ccc3c(c2)CCCN(C2CCCOC2)C3)n1] |
| 246 | 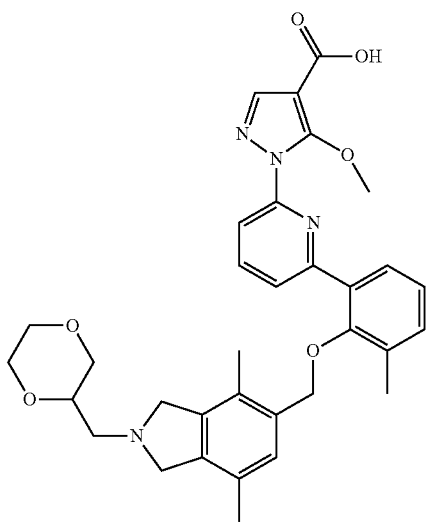 [SMILES: COc1c(C(=O)O)cnn1-c1cccc(-c2cccc(C)c2OCc2cc(C)c3c(c2C)CN(CC2COCCO2)C3)n1] |
| 247 | 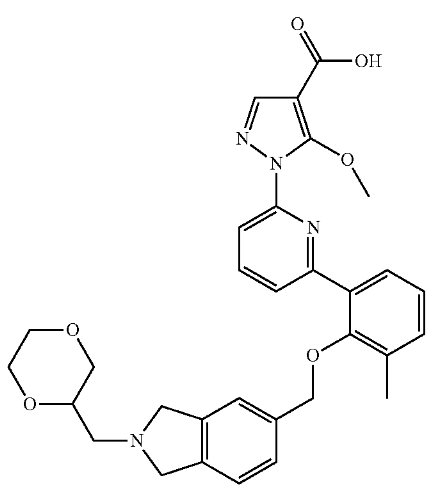 [SMILES: COc1c(C(=O)O)cnn1-c1cccc(-c2cccc(C)c2OCc2ccc3c(c2)CN(CC2COCCO2)C3)n1] |
| 248 | |
| 249 | |

TABLE 1-continued
| Cpd No. | Structure |
|---|---|
| 250 | 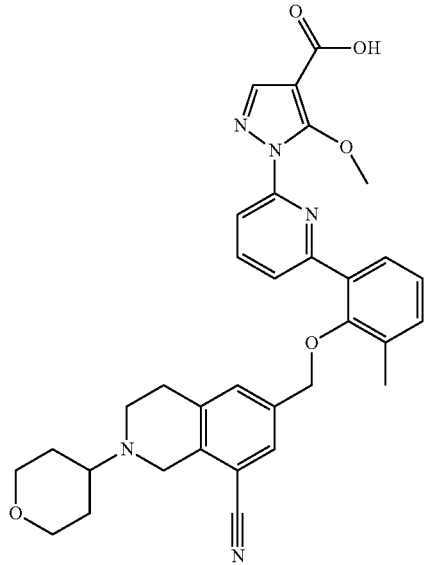 [SMILES: COc1c(C(=O)O)cnn1-c1cccc(-c2cccc(C)c2OCc2cc(C#N)c3c(c2)CCN(C2CCOCC2)C3)n1] |
| 251 | 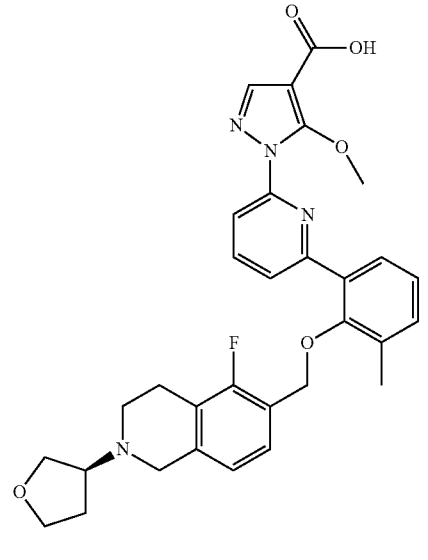 [SMILES: COc1c(C(=O)O)cnn1-c1cccc(-c2cccc(C)c2OCc2ccc3c(c2F)CCN([C@H]2CCOC2)C3)n1] |
| 252 | 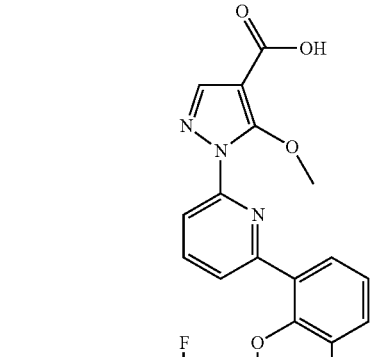 |
| 253 | 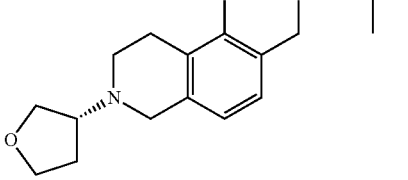 |
| 254 | 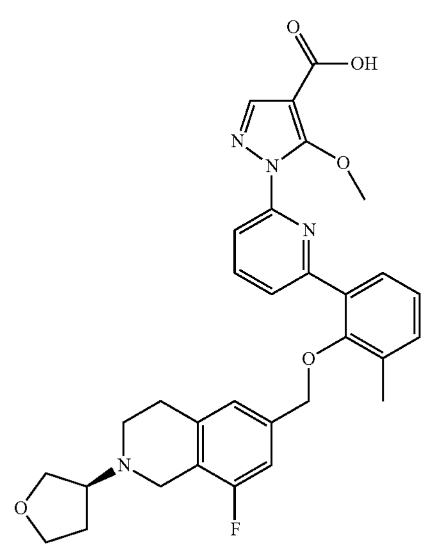 [SMILES: COc1c(C(=O)O)cnn1-c1cccc(-c2cccc(C)c2OCc2cc(F)c3c(c2)CCN([C@H]2CCOC2)C3)n1] |

TABLE 1-continued

| Cpd No. | Structure |
|---|---|
| 255 | 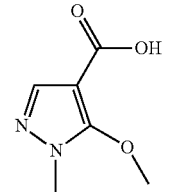 |
| 256 | 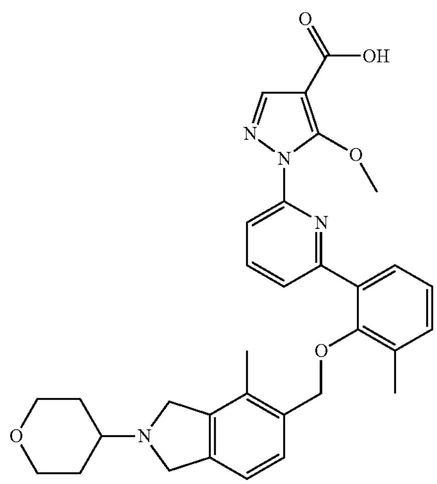 [SMILES: COc1c(C(=O)O)cnn1-c1cccc(-c2cccc(C)c2OCc2ccc3c(c2C)CN(C2CCOCC2)C3)n1] |
| 257 | 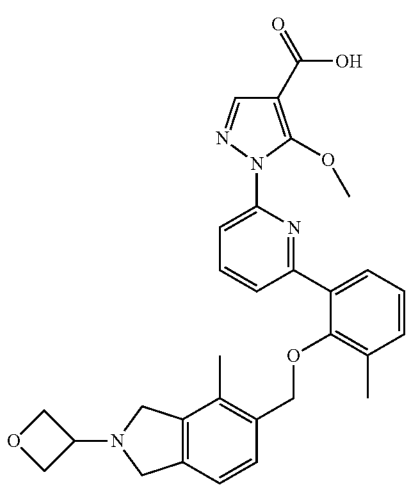 [SMILES: COc1c(C(=O)O)cnn1-c1cccc(-c2cccc(C)c2OCc2ccc3c(c2C)CN(C2COC2)C3)n1] |
| 258 | 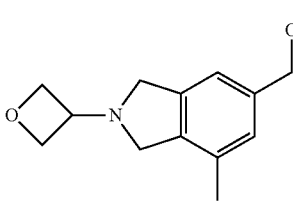 |

In one embodiment, the sCG activator used in the methods of the invention is selected from any of compounds depicted in Table 1 above, and the pharmaceutically acceptable salts thereof.

In another embodiment, the sCG activator used in the methods of the invention is selected from the group consisting of compound number 1, 2, 3, 4, 5, 7, 8, 9, 12, 15, 16, 18, 21, 27, 28, 30, 31, 35, 36, 39, 41, 42, 44, 45, 46, 47, 48, 57, 59, 62, 68, 77, 78, 79, 80, 82, 83, 84, 85, 86, 88, 92, 93, and 94 and the pharmaceutically acceptable salts thereof, as such compounds are depicted in Table 1.

In another embodiment, the sCG activator used in the methods of the invention is selected from the group consisting of compound number 95, 97, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 136, 137, 139, 140, 141, 142, 145, 146, 152, 153, 154, 155, 157, 158, 159,161, 162, 163, 164, 165, 166, 167, 169, 170, 171, 172, 173, 174, 175, 176, 177, 178, 179, 180, 181, 184, 185, 186, 187, 188, 189, 191, 193, 194, 195, 196, 197, 198, 199, 201, 202, 203, 204, 205, 206, 207, 208, 210, 211, 212, 213, 214, 215, 216, 220, 222, 223, 224, 225, 227, 229, 230, 231, 232, 233, 234, 235, 236, 237, 238, 239, 240, 241, 242, 243, 244, 246, 247, 248, 249, 250, 251, 252, 253, 254, 255, 256, 257 and the pharmaceutically acceptable salts thereof, as such compounds are depicted in Table 1.

In one embodiment, the SLGT2 inhibitor, when used in the methods of the invention, is selected from the group consisting of empagliflozin, dapagliflozin and canagliflozin.

In another embodiment, the SLGT2 inhibitor, when used in the methods of the invention, is empagliflozin.

BRIEF DESCRIPTION OF THE SEVERAL VIEW OF THE DRAWINGS

FIG. 1 shows a trial design schematic for a four arm clinical trial to investigate the effects of an oral sGC activator of the invention alone and in combination with empagliflozin on portal hypertension after 8 weeks treatment in patients with clinically significant portal hypertension (CSPH) in compensated cirrhosis. As shown in FIG. 1, the four arms or treatment groups are as follows: HBV arm (BID treatment with sGC activator alone); HCV arm (BID treatment with sGC activator alone), NASH arm without type 2 diabetes mellitus (BID treatment with sGC activator alone); and NASH arm with type 2 diabetes mellitus (BID treatment with sGC activator alone and QD treatment with empagliflozin).

DETAILED DESCRIPTION OF THE INVENTION

Abbreviations

| | |
|---|---|
| ALT | Alanine Aminotransferase |
| ARLD | Alcohol-related liver disease |
| AST | Aspartate aminotransferase |
| AUC | Area under the curve |
| BID | Bis in die (twice daily dosing) |
| BNP | Brain natriuretic peptide |
| CAP | Controlled attenuation parameter |
| CKD | Chronic kidney disease |
| CSPH | Clinically significant portal hypertension |
| CTCAE | Common Terminology Criteria for Adverse Events |
| DN | Diabetic nephropathy |
| eGFR | Estimated glomular filtration rate |
| EOT | End of treatment |
| ELF | Enhanced liver fibrosis |
| EOS | End of study |
| FHVP | Free hepatic venous pressure |
| γ-GT | Gamma-glutamyltransferase |
| HBV | Hepatitis B virus |
| HCV | Hepatitis C virus |
| HE | Hepatic encephalopathy |
| HOMA-IR | Homeostatic Model Assessment for Insulin Resistance |
| hs-CRP | High-sensitivity C-reactive protein |
| HVPG | Hepatic venous pressure gradient |
| ICH-GCP | International Council for Harmonisation of Technical Requirements for Pharmaceuticals for Human Use - Good Clinical Practice |
| IRT | Interactive response technology |
| LADA | Latent autoimmune diabetes in adults |
| NAFLD | Non-alcoholic fatty liver disease |
| NASH | Non-Alcoholic Steatohepatitis |
| NSBB | Non-selective beta-blocker |
| PD | Pharmacodynamic |
| PH | Portal hypertension |
| PK | Pharmacokinetic |
| PRO-C3 | N-terminal propeptide of type III collagen |
| QID | Quater in die (four times a day) |
| QD | Quaque Die (once a day) |
| sGC | Soluble guanylate cyclase |
| SGLT1 | Sodium-glucose cotransporter-1 (SGLT1) |
| SGLT2 | Sodium-glucose cotransporter-2 (SGLT2) |
| TID | Ter in Die (three times a day) |
| T2DM | Type 2 diabetes mellitus |
| VCTE ™ | Vibration controlled transient elastography |
| VH | Variceal haemorrhage |
| WHVP | Wedged hepatic venous pressure |
| WOCBP | Women of childbearing potential |

As used herein, the term "compensated cirrhosis" refers to absence of clinically evident decompensating events such as, for example, ascites [more than perihepatic ascites], variceal haemorrhage (VH) and/or apparent hepatic encephalopathy (HE).

As used herein, the term "clinically significant portal hypertension" (CSPH) refers to a hepatic venous pressure gradient (HVPG) greater than or equal to 10 mm Hg. In addition to this quantitative measurement of CSPH, the term "CSPH" may also refers to clinical signs of CSPH such as esophogastral varices, splenomegaly, low platelet count, porto-systemic shunts, and further clinical signs of CSPH. Methods of measuring HVPG, esophogastral varices, splenomegaly, low platelet count, porto-systemic shunts, and further clinical signs of CSPH are known in the art and/or described herein.

Unless specifically indicated, throughout the specification and the appended claims, a given chemical formula or name shall encompass tautomers and all stereo, optical and geometrical isomers (e.g. enantiomers, diastereomers, E/Z isomers ,etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound. Some of the compounds of formula (I) can exist in more than one tautomeric form. The invention includes methods for using all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g., trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

For all compounds disclosed herein above in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes $—(CH_2)—$, $—(CH_2—CH_2)—$, $—(CH(CH_3))—$, $—(CH_2—CH_2—CH_2)—$, $—(C(CH_3)_2)—$, $—(CH(CH_2CH_3))—$, $—(CH(CH_3)—CH_2)—$, $—(CH_2—CH(CH_3))—$, $—(CH_2—CH_2—CH_2—CH_2)—$, $—(CH_2—CH_2—CH(CH_3))—$, $—(CH(CH_3)—CH_2—CH_2)—$, $—(CH_2—CH(CH_3)—CH_2)—$, $—(CH_2—C(CH_3)_2)—$, $—(C(CH_3)_2—CH_2)—$, $—(CH(CH_3)—CH(CH_3))—$, $—(CH_2—CH(CH_2CH_3))—$, $—(CH(CH_2CH_3)—CH_2)—$, $—(CH(CH_2CH_2CH_3))—$, $—(CHCH(CH_3)_2)—$ and $—C(CH_3)(CH_2CH_3)—$.

The term "$C_{3-n}$-cycloalkyl", wherein n is an integer 4 to n, either alone or in combination with another radical denotes a cyclic, saturated, unbranched hydrocarbon radical with 3 to n C atoms. For example, the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—$R_a$ may be represented as phenyl-S(O)$_m$— when $R_a$ is phenyl and where m is 0, 1 or 2.

General Synthetic Methods

The compounds of formula (I) used in the methods of the invention may be prepared by the methods and examples described in WO 2014/039434.

Methods of Therapeutic Use

For therapeutic use, each of the compounds of formula (I) and the SGLT2 inhibitor, when used, mcly be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compound of formula (I) and the SGLT2 inhibitor, when used, may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regimen.

In one embodiment, the invention relates to a method for treating compensated cirrhosis, comprising administering to a patient in need thereof a pharmaceutical composition comprising a pharmaceutically effective amount of the sGC activator of the invention, or a pharmaceutically acceptable salt thereof.

In another embodiment, the invention relates to a pharmaceutical composition comprising the sGC activator of the invention for use in the treatment of a patient with compensated cirrhosis.

As mentioned above, dosage forms of the compound of formula (I) of this invention and the SGLT2 inhibitor, when used, may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)).

Specific dosage and treatment regimens will depend on factors such as the patient's general health profile, the severity and course of the patient's disorder or disposition thereto, and the judgment of the treating physician.

Within this invention it is to be understood that the combinations or combined uses of a sGC activator and SGLT2 inhibitor according to this invention may envisage the simultaneous, sequential or separate administration of the therapeutic components.

In this context, "combination" or "combined" within the meaning of this invention may include, without being limited, fixed and non-fixed (e.g. free) forms (including kits, or other administration, application or dosage forms) and uses, such as e.g. the simultaneous, sequential or separate use of the sGC activator and SGLT2 inhibitor. In this context, "combination" or "combined" within the meaning of this invention may further include additional therapeutic agents or concomitant therapies as described herein, The combined administration or application of this invention may take place by administering the therapeutic components together, such as e.g. by administering them simultaneously in one single or in two separate formulations. Alternatively, the administration may take place by administering the therapeutic components sequentially, such as e.g. successively in two separate formulations.

For the combination therapy of this invention the therapeutic components may be administered separately (which implies that they are formulated separately) or formulated altogether (which implies that they are formulated in the same preparation). Hence, the administration of one element of the combination of the present invention may be prior to, concurrent to, or subsequent to the administration of the other element of the combination.

In one embodiment, the methods of the invention comprise administering to the patient a daily amount of from 0.1 mg to about 50 mg of a sGC activator of the invention, or a pharmaceutically acceptable salt thereof.

In another embodiment, the methods of the invention comprise administering to the patient a daily amount of from 1 mg to about 30 mg of a sGC activator of the invention, or a pharmaceutically acceptable salt thereof.

In another embodiment, the sGC activator of the invention, or a pharmaceutically acceptable salt thereof, is administered to the patient in a daily amount of from 0.1 to 100 mg; or 1 to 25 mg; or 1 to 10 mg; or 2 to 5 mg, or a pharmaceutically acceptable salt thereof.

In another embodiment, the sGC activator of the invention, or a pharmaceutically acceptable salt thereof, is administered to the patient in an amount selected from the group consisting of 1 mg, 1.5 mg, 2 mg, 2.5 mg, 3 mg, 3.5 mg, 4, mg, 4.5 mg, 5 mg, 5.5 mg, 6 mg, 6.5 mg, 7 mg, 7.5 mg, 8 mg, 8.5 mg, 9 mg, 9.5 mg, and 10 mg.

In another embodiment, the sGC activator of the invention, or a pharmaceutically acceptable salt thereof, is administered to the patient in an amount selected from the group consisting of 1, 2, 3, 4, 5, 6, 7, 8, 9 or 10 mg.

In another embodiment, the methods of the invention comprise administering to the patient up to 3 mg of a sGC activator of the invention, or a pharmaceutically acceptable salt thereof.

In another embodiment, the methods of the invention comprise administering to the patient 1 mg of a sGC activator of the invention, or a pharmaceutically acceptable salt thereof.

In another embodiment, the methods of the invention comprise administering to the patient 2 mg of a sGC activator of the invention, or a pharmaceutically acceptable salt thereof.

In another embodiment, the methods of the invention comprise administering to the patient 3 mg of a sGC activator of the invention, or a pharmaceutically acceptable salt thereof.

The vasodilatation of the sGC activator may lead to orthostatic dysregulation and hypotensive episodes. Titration of the sGC activator may allow the total daily exposure of sGC activator to be further increased while high peak concentrations are avoided.

In one embodiment, the invention relates to a method for preventing or reducing the severity of orthostatic dysregulation caused by, due to, or related to administration of a sGC activator, or a pharmaceutically acceptable salt thereof, the method comprising administering the daily dose of the sGC activator to the patient BID, TID or QID.

In another embodiment, the invention relates to the method described immediately above, wherein the sGC activator is administered BID.

In another embodiment, the methods of the invention comprise a twice daily administration to a patient of up to 3 mg of a sGC activator of the invention, or a pharmaceutically acceptable salt thereof.

In another embodiment, the methods of the invention comprise a twice daily administration to a patient of 3 mg of a sGC activator of the invention, or a pharmaceutically acceptable salt thereof, to provide a total daily amount of 6 mg of sGC activator.

In another embodiment, the methods of the invention comprise a twice daily administration to a patient of 2 mg of a sGC activator of the invention, or a pharmaceutically acceptable salt thereof, to provide a total daily amount of 4 mg of sGC activator.

In another embodiment, the methods of the invention comprise a twice daily administration to a patient of 1 mg of a sGC activator of the invention, or a pharmaceutically acceptable salt thereof, to provide a total daily amount of 2 mg of sGC activator.

In another embodiment, the methods of the invention comprise administering to the patient 3 mg of a sGC activator of the invention, or a pharmaceutically acceptable salt thereof.

In one embodiment, the SGLT2 inhibitor, when used, is administered to the patient in a daily amount of 0.1 to 500 mg.

In another embodiment, the SLGT2 inhibitor, when used, is empagliflozin.

In another embodiment, empagliflozin, when used, is administered to the patient in a daily amount of 1, 2.5, 5, 10 or 25 mg.

In another embodiment, empagliflozin, when used, is administered to the patient in a daily amount of 10 or 25 mg.

In another embodiment, empagliflozin, when used, is administered to the patient in a daily amount of 10.

In another embodiment, empagliflozin, when used, is administered to the patient in an amount of 5 mg twice daily, to provide a total daily amount of 10 mg of empagliflozin.

In another embodiment, the invention relates to a method for treating a type 2 diabetes mellitus patient with CSPH in compensated cirrhosis due to NASH, the method comprising administering to the patient up to 3 mg twice daily of a sGC activator of the invention, or a pharmaceutically acceptable salt thereof, in combination with empagliflozin.

In another embodiment, the invention relates to the method described immediately above, wherein the empagliflozin is administered in a daily amount of 10 mg; or in an amount of 5 mg administered twice daily.

Patients being treated with the sCG activator of the invention, or a combination of the sGC activator and SGLT2 inhibitor, may be treated with one or more additional therapeutic agents. Nonlimiting examples of such one or more additional therapeutic agents include compounds for improving the metabolic (e.g., obesity, diabetic, inflammatory) condition of the patient. Nonlimiting examples of such compounds include, e.g., DPP-IV inhibitors (e.g., linagliptin, sitagliptin, saxagliptin, vildagliptin, and alogliptin), glitazones/thiazolidinediones (e.g., pioglitazone and rosiglitazone), glucagon-like peptide 1 (GLP-1)-based therapies (e.g., GLP-1 receptor agonists), metformin, insulin, and other metabolic disease drugs such as anti-hypertensives (e.g., diuretics, calcium channel blockers, angiotensin-converting enzyme (ACE) inhibitors, angiotensin II receptor antagonists (ARBs), adrenergic receptor antagonists, vasodilators, renin inhibitors, aldosterone receptor antagonist, and alpha-2 adrenergic receptor agonists) and statins (e.g., atorvastatin, lovastatin, pitavastatin, pravastatin, rosuvastatin and simvastatin).

For patients having NASH, treatment with the sGC activator of the invention, or a combination of the sGC activator and SGLT2 inhibitor, may further comprise treatment with compounds useful for treating NASH/including metabolism modulators RAAS inhibitors, lipid modulators anti-fibrotic agents, anti-inflammatory agents, and immunomodulating agents Nonlimiting examples of such NASH combination partners include:

PF-05221304 (Pfizer), Obeticholic acid (Intercept), GS-0976 (Gilead), GS-9674 (Gilead), LJN452 (Novartis), LMB763 (Novartis), MSDC-0602K/Metabolic Solutions (Octeca), EDP-305 (Enanta), INT-767 (Intercept), O304 (Betagenon), PF-06835919 (Pfizer), Semaglutide (Novo Nordisk), BMS-986036 (BMS), NGM282 (NGM), BMS-986171 (BMS), PF-06865571 (Pfizer), LIK066 (Novartis), ORMD 0801 (Oramed), CER-209 (Cerenis), TVB-2640 (3-V Bioscience), DS102 (Afimmune), MGL-3196 (Madrigal, Roche), VK2809 (Viking), Volixibat (Sanofi, Shire), IONIS-DGAT2Rx (Ionis), AKCEA-ANGPTL3-LRx (Akcea), Gemcabene (Gemphire), MT-3995 (Mitsubishi Tanabe), DUR-928 (Durect), CORT118335 (Corcept), amacizumab (BirdRock/Janssen), Elafibranor (Genfit), GRI-0621 (GRI Bio), Selonsertib (Gilead), Cenicriviroc (Takeda, Allergan), JKB 121 (Taiwan), Saroglitazar (Zydus), IMM-124E (Immuron), Lanifibranor(IVA337) (Inventiva), GR-MD-02 (Galectin), Emricasan(VAY785) (Novartis), Tipelukast (Kyorin, MediciNova), BMS986263 (ND-L02-s201) (BMS), PF-06667272 (Pfizer), Foralumab (Tiziana), and DRX-065 (DeuteRx).

In another embodiment, the NASH combination partner is selected from:

acetyl-CoA carboxylase (ACC) inhibitors (e.g., GS-0976);

amine oxidase, copper containing 3 (AOC3) inhibitors (e.g., BI 1467335 (formerly known as PXS-4728A));
farnesoid X receptor (FXR) agonists (e.g. obeticholic acid);
apoptosis signal-regulating kinase 1 (ASK1) inhibitors (e.g. selonsertib);
C-C chemokine receptor types 2 (CCR2) and 5 (CCR5) antagonists (e.g. ceniriviroc);
caspase inhibitors (e.g. emricasan);
peroxisome proliferator-activated receptor-gamma (PPAR) agonists (e.g. elafibranor);
stearoyl CoA desaturase-1 inhibitors (e.g., aramchol);
vascular adhesion protein-1 (VAP-1) inhibitors (e.g., PXS4728A); and
pioglitazone/vitamin.

Clinical Trial Protocol

Clinical Trial

The below describes a clinical trial protocol directed to treatment of patients with CSPH in compensated cirrhosis due to HBV, HCV and NASH with or without T2DM.

Trial Objectives and Endpoints

Main Objectives, Primary and Secondary Endpoints

Main Objectives

The trial will investigate the safety and tolerability of a sGC activator in patients with CSPH in compensated cirrhosis due to HBV, HCV and NASH with or without T2DM and the combination of a sGC activator and empagliflozin in patients with CSPH in compensated cirrhosis due to NASH with T2DM, on top of standard of care respectively. The primary objective is to estimate the percentage change in HVPG from baseline measured after 8 weeks. The primary analysis will be made for treated patients with baseline HVPG measurements (Full Analysis Set, FAS) as if all patients took treatment for the duration of the trial.

Primary Endpoint(s)

The primary endpoint is the percentage change in HVPG from baseline (measured in mmHg) after 8 weeks of treatment.

Secondary Endpoint(s)

Secondary endpoints include:
occurrence of a response, which is defined as >10% reduction from baseline HVPG (measured in mmHg) after 8 weeks of treatment
occurrence of one or more decompensation events (i.e. ascites, VH, and/or overt HE) during the 8-week treatment period
occurrence of CTCAE grade 3 (or higher) hypotension or syncope based on Investigator judgement, during the 8-week treatment period occurrence of discontinuation due to hypotension or syncope during the 8-week treatment period Further Objectives and Further Endpoints Further Objectives In addition to the main objectives defined above, further objectives of this trial include an evaluation of general safety, PK, PD, disease activity biomarkers, and to gain further insight into the use of non-invasive methods to investigate liver function and portal pressure.

Further Endpoints

Further endpoints include (but will not be limited to) those shown below.
change from baseline in spleen stiffness (kPa), by FibroScan® Expert 630, after 8 weeks of treatment
change from baseline in liver fat content (dB/m) by FibroScan® Expert 630 CAP, after 8 weeks of treatment
change from baseline in liver stiffness (kPa) by FibroScan® Expert 630 LSM, after 8 weeks of treatment
change from baseline in metabolic function after 8 weeks of treatment measured by:
HbA1c
plasma glucose
HOMA-IR
change from baseline in body weight after 8 weeks of treatment
change from baseline in hepatic function after 8 weeks of treatment measured by:
PT/INR, aPTT
bilirubin (direct and indirect)
liver enzymes (ALT, AST, $\gamma$-GT and alkaline phosphatase) albumin
change from baseline in renal function after 8 weeks of treatment, measured by eGFR
change from baseline across disease-specific and mode of action exploratory biomarkers after 8 weeks of treatment and at EoS
Fibrosis markers (e.g. PRO-C3, ELF score)
Inflammation markers (e.g. hs-CRP)
Cardiac and renal biomarkers (e.g. Brain Natriuretic Peptide (BNP), Troponin I, eGFR, creatinine)
PK endpoints of the sCG activator and empagliflozin will be determined if feasible:
$C_{max}$ (maximum measured concentration of the analyte in plasma)
$t_{max}$ (time from dosing to maximum measured concentration of the analyte in plasma)
$AUC_{t1-t2}$ (area under the concentration-time curve of the analyte in plasma over the time interval t1 to t2 after single dose administration)
$C_{max,N}$ (maximum measured concentration of the analyte in plasma following N doses)
$t_{max,N}$ (time from last dosing to maximum measured concentration of the analyte in plasma after administration of N doses)
$AUC_{t1-t2,N}$ (area under the concentration-time curve of the analyte in plasma over the time interval t1 to t2 after administration of Nth dose)
$C_{max,ss}$ (maximum measured concentration of the analyte in plasma at steady state over a uniform dosing interval $\tau$)
$t_{max,ss}$ (time from last dosing to maximum measured concentration of the analyte in plasma at steady state over a uniform dosing interval $\tau$)
$AUC_{t1-t2,ss}$ (area under the concentration-time curve of the analyte in plasma over the time interval t1 to t2 at steady state)
$C_{pre,N}$ (predose concentration of the analyte in plasma immediately before administration of the Nth dose after N−1 doses were administered)
$C_{pre,ss}$ (predose concentration of the analyte in plasma at steady state immediately before administration of the next dose)
$C_{t,N}$ (concentration of the analyte in plasma at time t following N doses)
Further PK parameters may be calculated as appropriate.

The following further endpoint will be measured based on data collected in countries where respective Regulatory requirements are in place and implementation occurs via a country specific local amendment to this protocol:

change from baseline in liver function after 8 weeks of treatment measured by the disease severity index (DSI) and related parameters using the HepQuant® Dual Cholate Clearance Test Additional further endpoints may be defined in the Trial Statistical Analysis Plan (TSAP).

Description of Design and Trial Population

Overall Trial Design

This phase II multi-national, randomised, open-label and parallel group trial to investigate the effects of oral sGC activator alone and in combination with empagliflozin on portal hypertension after 8 weeks treatment in patients with clinically significant portal hypertension (CSPH) in compensated cirrhosis.

Patients will be enrolled in the trial and screened for eligibility once they have signed the informed consent. The screening period consists of up to 3 visits (Visits 1a, b and c) and will last a maximum of 4 weeks. Patients will be able to progress from one visit to the next when eligibility of the previous visit is confirmed. Assessments will include a gastroscopy, ultrasound of the liver and spleen, FibroScan® of the liver and spleen, and measurement of HVPG. Patients who remain eligible and who successfully complete this period will proceed to the 8-week open label, active treatment period. In total, 80 patients will enter the trial with 20 patients in the HBV arm (treatment group 1), 20 patients in the HCV arm (treatment group 2) and 40 patients in the NASH arms (treatment group 3 and 4).

Two types of NASH patients (either with or without a diagnosis of T2DM) will enter treatment group 3 or 4. NASH patients without diagnosis of T2DM can only enter treatment group 3 (high dose BID of sGC activator alone) at Visit 2. NASH patients with diagnosis of T2DM will be randomized at visit 2 in a 1:1 ratio into either treatment group 3 (high dose BID of sGC activator alone) or treatment group 4 (high dose BID of GC activator+empagliflozin QD). Once the number of patients reaches 20 in treatment group 3, the enrollment of NASH patients without T2DM will be stopped and only NASH patients with T2DM will be enrolled into treatment group 4, until the number of patients in this group reaches 20. Although randomization is applied, the patients, investigators and sponsors will stay unblinded due to the open-label nature of this trial.

Following enrollment and randomization at visit 2, patients will begin the intake of trial medication(s) and will enter a dose-titration period of sGC activator. All patients in all 4 treatment groups will start this period on a low dose BID of sGC activator. If the low dose is tolerated, one week later (at Visit 3, day 8), the dose for all patients will be up-titrated to medium dose BID of sGC activator. If this medium dose is tolerated, a second up-titration to high dose BID of sGC activator will occur after another week (at Visit 4, day 15). Following the dose-titration period, and if the dose is tolerated, patients will remain on the highest dose of sGC activator for the remainder of the treatment period until they reach the End of Treatment (EoT) visit and 8 weeks of treatment. If the dose is not tolerated, trial medication may be interrupted or the dose can be reduced/down-titrated. Patients in the treatment group 4 will receive a fixed dose of empagliflozin QD in addition to sGC activator starting at visit 2. The ultrasound and FibroScan® of the liver and spleen, and the HVPG measurement will be repeated during the treatment period (see FIG. 1).

After the 8 week treatment period all patients will enter a 4 week follow-up period without trial medication. The patient's participation in the trial will be complete when they have performed the last planned visit (i.e. End of Study [EoS], 4 weeks after EoT).

Discussion of Trial Design, Including the Choice of Control Group(s)

A randomised, open-label and parallel group design has been chosen for this exploratory trial with a very short treatment period, on top of standard of care. The parallel group will enable comparison of four different patient groups and the open label design will provide benefit to all patients participating in it.

A treatment duration of 8 weeks has been chosen to allow an evaluation of short-term efficacy and indirect comparison to the week 8 results from trial NCT05161481 (first posted Dec. 17, 2021). The patient population of this trial (HBV, HCV and NASH patients with and without T2DM) has been chosen as it represents a sub-set of the intended patient population for sGC activator (patients with clinically significant portal hypertension in compensated cirrhosis due to noncholestatic liver diseases).

In Arm 4, a combination of sGC activator and empagliflozin will be investigated to assess the additional benefit of metabolic improvement by a SGLT2 inhibitor, in this study empagliflozin, in patients with NASH and T2DM.

The measurement of HVPG was chosen as the primary endpoint as it is the gold standard to estimate portal venous pressure in patients with cirrhosis, i.e. assessing the severity of sinusoidal PH (see T. Reiberger et al., "Austrian consensus guidelines on the management and treatment of portal hypertension (Billroth III)," Wien Klin Wochenschr 2017; 129(Suppl 3):5135-158)). It is used as an established surrogate marker for improvement and/or worsening of liver fibrosis/function, since a decrease in HVPG translates into a clinically meaningful benefit (see M. Mandorfer et al., "Changes in hepatic venous pressure gradient predict hepatic decompensation in patients who achieved sustained virologic response to interferon-free therapy," Hepatology 2020;71(3);1023-1036)). The prognostic value of HVPG has been underlined by several landmark studies, showing that an HVPG ≥10 mmHg (i.e. CSPH) is predictive of the formation of varices (see R. J. Groszmann et al. "Portal Hypertension Collaborative Group. Beta-blockers to prevent gastroesophageal varices in patients with cirrhosis," N Engl J Med 2005;353(21);2254-2261), while a (pharmacologically-induced) decrease of HVPG modulates the respective risk of variceal growth and decompensation (see C. Merkel et al., "Gruppo Triveneto per l'Ipertensione Portale. A placebo-controlled clinical trial of nadolol in the prophylaxis of growth of small esophageal varices in cirrhosis. Gastroenterology 2004;127(2);476-484; and M. Mandorfer et al., "Hepatic venous pressure gradient response in non-selective beta-blocker treatment—is it worth measuring?" Curr Hepatol Rep 2019;18;174-186). Hence, this also explains the choice of the secondary endpoint relating to the occurrence of one or more decompensation events.

Other secondary endpoints (occurrence of significant hypotension or syncope, and occurrence of discontinuation due to hypotension or syncope) were chosen as they are relevant based on the mechanism of action of the sGC activator.

Patients will be screened for the trial based on the eligibility criteria. These include the selection of patients with documented endoscopically proven gastro-oesophageal varices or documented endoscopic-treated oesophageal varices as preventative treatment, as varices only occur in patients with CSPH. At Visit 1c (the final visit within the screening period) patients who remain eligible following Visits 1a and 1b will undergo their first HVPG measurement. Those with an HVPG≥10 mmHg (based on a local interpretation of the pressure tracing) will remain eligible. With this approach, the trial is designed to enroll patients with CSPH but the burden of the invasive HVPG procedure will be reduced and only performed on patients who successfully reach Visit 1c, rather than on all screened patients.

Non-invasive assessments (i.e. ultrasound and Fibro-Scan® of the liver and spleen and functional liver testing) have been chosen as part of the screening procedures to further investigate the patients' status, to establish baseline values for comparison with treatment, and to gain further insight into the use of non-invasive methods to investigate liver function and portal pressure. These assessments will be repeated (see FIG. 1) to assess a time-dependency of the treatment.

Following enrollment/randomization, the trial design includes a dose-titration period. The mechanism related vasodilatation of the sGC activator can lead to orthostatic dysregulation and hypotensive episodes. The orthostatic dysregulation is dose-limiting and clinical tolerability is improved if the dose is titrated. A BID administration also allows the total daily exposure of sGC activator to be further increased while high peak concentrations are avoided. Hence, in this trial, a dose-titration regimen of low dose BID to medium dose BID to high dose BID will be followed.

Selection of Trial Population 80 patients with CSPH in compensated cirrhosis due to HBV, HCV and NASH with or without T2DM will be enrolled into the trial. Approximately 42 sites are planned across multiple countries. It is anticipated that 2 patients will be randomised at each site. If enrolment is delayed, additional sites may be recruited.

Screening of patients for this trial is competitive, i.e. screening for the trial or one of the treatment arms will stop at all sites at the same time once a sufficient number of patients have been screened to deliver the required number of randomised patients. Investigators will be notified about the screening completion and will then not be allowed to screen additional patients for this trial. Patients already in screening at this time will be allowed to continue to randomisation if eligible.

Re-testing during the screening period is allowed once (e.g. if the Investigator believes an ineligible laboratory test is the result of an error or extenuating circumstances, the test can be repeated once without the patient having to be re-screened). This excludes the gastroscopy and the HVPG measurement. Re-screening is also allowed once provided that the reasons for screen failure were reversible and have been resolved, based on Investigator judgement. A patient is considered a "re-screener" if he/she was not eligible for the trial initially and is subsequently re-screened, going through the informed consent process for a second time, receiving a new unique patient number and repeating the screening period assessments.

Main Diagnosis for Trial Entry

The trial will include patients with compensated cirrhosis due to HBV, HCV and NASH (with or without T2DM) with endoscopic proof of gastro-oesophageal varices, or endoscopic treated oesophageal varices as preventative treatment, as a sign of CSPH, together with an HVPG≥10 mmHg.

Inclusion Criteria
  Signed and dated written informed consent in accordance with ICH-GCP and local legislation prior to admission to the trial
  Male or female who is ≥18 (or who is of legal age in countries where that is greater than 18) and ≤75 years old at screening (Visit 1a)
  Clinical signs of CSPH as described by either one of the points below. Each trial patient must have a gastroscopy during the screening period (Visit 1b) or within 3 months prior to screening (Visit 1b).
    documented endoscopic proof of oesophageal varices and/or gastric varices at screening (Visit 1b) or within 3 months prior to screening (Visit 1b)
    documented endoscopic-treated oesophageal varices as preventative treatment
  CSPH defined as baseline HVPG≥10 mmHg (measured at Visit 1c), based on a local interpretation of the pressure tracing
  Diagnosis of compensated cirrhosis due to HCV, HBV, or NASH with or without T2DM. Diagnosis of cirrhosis must be based on histology (historical data is acceptable) or on clinical evidence of cirrhosis (e.g. platelet count <150×10$^9$/L [150×10$^3$/µL], nodular liver surface on imaging or splenomegaly etc.)
  Diagnosis of NASH based on either
    Current or historic histological diagnosis of NASH OR steatosis
    OR
    Clinical diagnosis of NASH based on historic or current imaging diagnosis of fatty liver (Fibro-Scan®, US, MRI, CT) AND at least 2 current or historic comorbidities of the metabolic syndrome (overweight/obesity, T2DM, hypertension, hyperlipidemia)
  Willing and able to undergo HVPG measurements per protocol (based on Investigator judgement)
  If receiving statins must be on a stable dose for at least 3 months prior to screening (Visit 1b), with no planned dose change throughout the trial
  If receiving treatment with NSBB s or carvedilol must be on a stable dose for at least 3 months prior to screening (Visit 1b), with no planned dose change throughout the trial
  If receiving pioglitazone, GLP1-agonists, or vitamin E must be on a stable dose for at least 3 months prior to screening (Visit 1b), with no planned dose change throughout the trial
  WOCBP must be ready and able to use highly effective methods of birth control per ICH M3 (R2) that result in a low failure rate of less than 1% per year when used consistently and correctly from the randomisation visit (Visit 2) until 7 days after the last treatment in this trial. The patient must agree to periodic pregnancy testing during participation in the trial.
  Men able to father a child and who have a female sexual partner of CBP, must use a condom with or without spermicide, or adopt complete sexual abstinence, or be vasectomised (with appropriate post-vasectomy documentation of the absence of sperm in the ejaculate), from the randomisation visit (Visit 2) until 7 days after the last treatment in this trial.
3.3.3 Exclusion Criteria
  Previous clinically significant decompensation events (e.g. ascites [more than perihepatic ascites], VH and/or overt/apparent HE)
  History of other forms of chronic liver disease (e.g. alcohol-related liver disease (ARLD), autoimmune liver disease, primary biliary sclerosis, primary sclerosing cholangitis, Wilson's disease, haemachromatosis, alpha-1 antitrypsin [A1At] deficiency)

Patients without adequate treatment for HBV, HCV or NASH as per local guidance (e.g. antiviral therapy for chronic HBV or HCV infection or lifestyle modification in NASH)

if received curative anti-viral therapy for HCV, no sustained virological response (SVR) or SVR sustained for less than 2 years prior to screening or if HCV RNA detectable If receiving anti-viral therapy for HBV, less than 6 months on a stable dose prior to screening, with planned dose change during the trial and HBV DNA detectable Weight change ≥5% within 6 months prior screening Must take, or wishes to continue the intake of, restricted concomitant therapy or any concomitant therapy considered likely (based on Investigator judgement) to interfere with the safe conduct of the trial SBP<100 mmHg and DBP<70 mmHg at screening (Visit 1a)

Model of End-stage Liver Disease (MELD) score of >15 at screening (Visit 1a), calculated by the central laboratory Hepatic impairment defined as a Child-Turcotte-Pugh score ≥B8 at screening (Visit 1a), calculated by the site, using central laboratory results ALT or AST >5 times upper limit of normal (ULN) at screening (Visit 1a), measured by the central laboratory eGFR (CKD-EPI formula) <20 mL/min/1.73 m2 at screening (Visit 1a), measured by the central laboratory Alpha-fetoprotein >50 ng/mL (>50 µg/L) at screening (Visit 1a), measured by the central laboratory An active infection with SARS-CoV-2 (or who is known to have a positive test from screening [Visit 1a] until randomisation [Visit 2])

Prior orthotopic liver transplantation

Prior or planned TIPS or other porto-systemic bypass procedure

Known portal vein thrombosis

History of clinically relevant orthostatic hypotension, fainting spells or blackouts due to hypotension or of unknown origin (based on Investigator judgement)

QTcF-interval >450 ms in men or >470 ms in women at screening (Visit 1a), a family history of long QT syndrome, or concomitant use of therapies with a known risk of Torsade de Pointes or planned initiation of such therapies during the trial Type 1 diabetes mellitus, or history of other autoimmune causes of diabetes mellitus (e.g. LADA)

Patients at increased risk of ketoacidosis in the opinion of the investigator.

Contraindication to any of the trial assessments (e.g. poor patient co-operation for gastroscopy, cardiac pacemakers for FibroScan® [if contraindicated based on local market approval] etc.)

Major surgery (major according to the investigator's assessment) performed within 12 weeks prior to randomisation (Visit 2) or planned during the trial, e.g. hip replacement.

Any documented active or suspected malignancy or history of malignancy within 5 years prior to screening (Visit 1a), except appropriately treated basal cell carcinoma of the skin or in situ carcinoma of uterine cervix History of (in the 6 months prior to randomisation [Visit 2]), or ongoing, chronic drug abuse, or not expected to comply with the protocol requirements for any other reason that, based on Investigator judgement, makes the patient an unreliable trial recruit or unlikely to complete the trial as scheduled Previous randomisation in this trial, previous exposure to the SCG activator, or an allergy/contraindication to the sGC activator and/or any of the excipients Currently enrolled in another investigational device or drug trial, or less than 30 days or 5 half-lives (whichever is longer) prior to randomisation (Visit 2) since ending another investigational device or drug trial, or receiving other investigational treatment(s)

Women who are pregnant, nursing, or who plan to become pregnant while in the trial Any other medical condition that, based on Investigator judgement, poses a safety risk for the patient or may interfere with the objectives of the trial Treatments The investigational medicinal products in the trial are the sGC activator and empagliflozin.

Method of Assigning Patients to Treatment Groups

After the assessment of all in- and exclusion criteria, each eligible patient will enter the treatment phase at visit 2. HBV patients will be assigned to treatment group 1 and HCV patients to treatment group 2 via an Interactive Response Technology (IRT) system. NASH patients with T2DM will be randomised to treatment group 3 or 4 in a 1:1 ratio via the IRT system. NASH patients without diagnosis of T2DM will only be assigned to treatment group 3 via IRT. Once the number of patients enrolled in treatment group 3 reaches 20, the IRT system will only continue to enroll NASH patients with T2DM to treatment group 4 until the total number of patients in this group reaches 20 as well.

Drug Assignment and Administration of Doses for Each Patient

Trial medication will be dispensed at the investigational sites in accordance with the Flow Chart. At dispensing visits patients will be given the appropriate number of medication kits for the sGC activator (range 1-2) and empagliflozin (range 1-2) depending on the interval between the visits. The last dose of the sGC activator will be administered in the evening of the day before the EoT visit and the last dose of empagliflozin in the morning of the day before the EoT visit.

All patients will start on a dose of low dose of sGC activator BID at Visit 2. Treatment group 4 will receive a fixed dose of empagliflozin QD in addition. 7 days later, at Visit 3, and again at Visit 4, 7 days after Visit 3, all patients will be up-titrated to a medium dose of sGC activator BID, and then to the maintenance high dose of sGC activator BID.

Patients will be informed of the dose titration period and will be made aware that up-titration for the sGC activator is being used. From Visit 4 onwards, patients of the treatment group 1, 2, 3 and 4 will continue to receive the maximum dose of high dose of sGC activator (plus empagliflozin QD for group 4 only) until reaching the EoT visit (8 weeks after starting the trial medication).

From the start of the treatment period (i.e. from Visit 2), and until reaching the EoT visit 8 weeks later, patients will be instructed to take the sGC activator orally twice a day (BID) and empagliflozin orally once a day (QD). Each dose of the sGC activator will consist of one film-coated tablet. It is recommended that the first daily dose is taken in the morning, and the second dose in the evening. Ideally there should be at least 10 hours in between the intake of each dose. The sGC activator should be taken at approximately the same time every day. If a dose is missed this must not be rectified by taking two doses (i.e. double doses) at the next time point; if a dose is missed by more than 6 hours, that dose should be skipped altogether and the next dose taken as scheduled. Trial medication should be taken with a glass of water and can be taken with or without food.

Patients in the treatment group 4 will be taking in addition one film-coated tablet of empagliflozin together with the first daily dose of the sGC activator in the morning. To ensure a dose interval of about 24 hours for empagliflozin the medication should be taken in the morning approximately the same time every day. If a dose of empagliflozin is missed by more than 12 hours, that dose should be skipped and the next dose should be taken as scheduled. No double doses should be taken. Both medications should be taken together with a glass of water and can be taken with or without food.

Restrictions

Restrictions Regarding Concomitant Treatment

The following concomitant therapies must not be administered to patients with diagnosis of NASH. These restrictions apply from within 5 half-lives after the concomitant therapy has been stopped prior to enrolment (Visit 2), until the EoS visit.
  other SGLT2 or SGLT-1/2 inhibitors
The concomitant therapies mentioned below must not be co-administered with the sGC activator.
  NO-sGC-cGMP pathway activating therapies like NO-donors (e.g. glyceryl trinitrate, isosorbide di- or mono-nitrate, molsidomine), PDE-5-inhibitors (e.g. sildenafil, tadalafil, and vardenafil), non-specific PDE inhibitors such as dipyridamole and theophylline, or sGC-stimulators (e.g. riociguat): These restrictions apply from within 5 half-lives after the concomitant therapy has been stopped prior to enrolment (visit 2), until the EoS visit.
  Concomitant therapies with a known risk of Torsade de Pointes: These restrictions apply from screening Visit 1a, until the EoS visit. In the event of temporary concomitant use of such a therapy, the trial medication must be temporarily stopped and can then be re-started at least 5 half-lives after the concomitant therapy with the known risk of Torsade de Pointes has been stopped.
Co-administration of the following concomitant therapies along with either trial medication, the sGC activator and empagliflozin, is not permitted within 5 half-lives after the concomitant therapy has been stopped prior to enrolment (visit 2), until the EoS visit.
  clinically relevant OATP1B1/3 inhibitors
  clinically relevant concomitant therapies known to inhibit or induce UGT enzymes
In the event of temporary concomitant use of medication that is not permitted, the sGC activator and/or empagliflozin must be temporarily stopped and can be re-started after a period of at least 5 half-lives after the concomitant therapy has been stopped. If permanent use of any of the above-mentioned prohibited therapy is required, both trial medications should be stopped.

Furthermore, patients who are receiving statins, or treatment with NSBBs/carvedilol, pioglitazone, GLP1-agonists, or vitamin E, must be on a stable dose for at least 3 months prior to screening (Visit 1b), with no planned dose change throughout the trial. In addition, these concomitant therapies should not be initiated during the trial as they will interfere with the efficacy of the trial medication.

If receiving anti-viral therapy for HBV, patients must be on a stable dose for at least 6 months prior to screening, with no planned dose change throughout the trial.

Close Monitoring for AEs Based on Concomitant Therapy

If a patient is taking concomitant therapy that is metabolised by CYP3A4, which has a narrow therapeutic index and/or is a sensitive substrate, close monitoring for AEs is recommended in this trial.

Assessments

Assessment of Efficacy
Hepatic Venous Pressure Gradient

The HVPG procedure within the trial will be conducted in a standardised fashion at all sites; training will be provided. Each trial site will be asked to provide acceptable sample HVPG tracing(s) prior to commencing patient recruitment if not already provided for Trial 1366-0021. Measurements of wedged hepatic venous pressure (WHVP) and free hepatic venous pressure (FHVP) will be performed in triplicate; tracings will be provided to an external Supplier and read centrally by independent expert(s) in PH; the central read will include a subjective assessment of the overall trace quality as well as a read of the relevant pressures. The independent expert(s) will be blinded to the timepoint that the trace relates to. The central read will include the traces from Visit 1c that have also been interpreted locally. The results of the central read will be transferred to the Sponsor and will be considered the official evaluation of the trial. In case of discrepancies between a local interpretation and the central evaluation (e.g. of the Visit 1c tracing), the central evaluation will remain valid.

HVPG measurements should be performed using the same hepatic vein, prior to intake of the trial medication, after an overnight fast, and ideally in the morning. If it is not possible to perform the measurement at Visit 1c in the morning an alternative time of day can be chosen; in this case, a fast of at least four hours is required. All subsequent HVPG measurements must then be performed at approximately the same time of day as the Visit 1c measurement for a single patient. If Visit 1b and 1c are performed on the same day, the HVPG measurement must be performed after the gastroscopy (i.e. only once it is confirmed that the patient remains eligible for the trial). During the treatment period, following randomisation, HVPG measurements should be performed on the day of the scheduled visit, or within seven days (if this latter approach is taken, the measurement should still be performed after an overnight fast/after a fast of at least four hours).

A summary of the HVPG procedure is as follows (see T. Reiberger et al., "Measurement of the hepatic venous pressure gradient and transjugular liver biopsy," J Vis Exp 2020 (160); e58819)

Under local anaesthesia and ultrasound guidance, a catheter introducer sheath is placed in the right internal jugular vein. Using fluoroscopic guidance, a balloon catheter is advanced into the inferior vena cava (IVC) and inserted into a large hepatic vein. Correct and sufficient wedge position of the catheter is ensured by injecting contrast media while the balloon is blocking the outflow of the cannulated hepatic vein. After calibrating the external pressure transducer, continuous pressure recordings are obtained with triplicate recordings of the WHVP and FHVP. The difference between FHVP and WHVP is referred to as HVPG, with values ≥10 mmHg indicating CSPH. Before removing the catheter, pressure readings obtained in the IVC at the same level, as well as the right atrial pressure, are recorded.

FibroScan® Measurements

The liver and spleen will be evaluated using the FibroScan® Expert 630 device, a noninvasive advanced technique using vibration controlled transient elastography (VCTE™) technology.

FibroScan® of the liver has been available for a number of years, and is a standard procedure used for screening and management of patients with liver disease. The ability to assess spleen stiffness using FibroScan® has only recently become possible following the introduction of the FibroScan® Expert 630 model; hence, spleen stiffness measurements are not yet a standard part of clinical practice in the patient population planned for this trial.

Evaluations will be performed after an overnight. At screening the FibroScan® can be performed at either Visit 1b or 1c. During the treatment period, following randomisation, assessments should be performed on the day of the scheduled visit, or within seven days (if this latter approach is taken, the measurement must still be performed after an overnight fast).

The following assessments will be performed:
liver stiffness measurement (LSM) using VCTE™
liver fat using Controlled Attenuation Parameter (CAP)
spleen stiffness measurement using VCTE™

What is claimed is:

1. A method for treating a patient with compensated cirrhosis, comprising administering to the patient a therapeutically effective amount of a soluble guanylate cyclase (sGC) activator of formula (I),

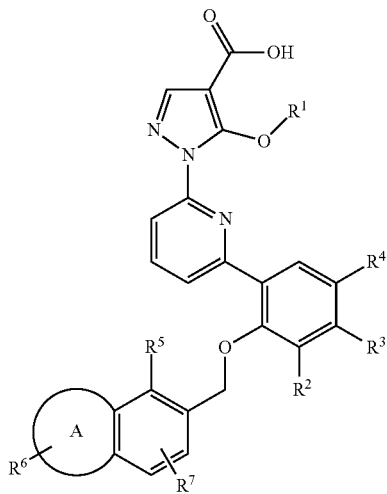

I wherein:
A is a 5-7 membered saturated heterocyclyl group containing one nitrogen and optionally one oxygen, wherein one carbon of said heterocyclyl group is optionally substituted with one or two groups selected from $C_{1-3}$alkyl and oxo ;
$R^1$ is $C_{1-4}$ alkyl optionally substituted with a methoxy group;
$R^2$ is selected from H, F, Cl, $C_{1-3}$alkyl, —CN, —OMe and —$CF_3$;
$R^3$ is selected from H and —$CH_3$;
$R^4$ is selected from H, F, —$CH_3$ and —OMe;
$R^5$ is selected from H, Cl, —$CH_3$, —$CH_2CH_3$, —$CF_3$, F, and —OMe;

$R^6$ is bonded to the nitrogen on A and is selected from H, $C_{1-6}$alkyl, —$(CH_2)_nC_{3-6}$cycloalkyl, —$C(O)C_{1-6}$alkyl, —$(CH_2)_n$-heterocyclyl, —$(CH_2)_n$-aryl, and —$(CH_2)_n$-heteroaryl, —$SO_2$aryl, $SO_2C_{1-6}$alkyl wherein said $C_{1-6}$alkyl, —$(CH_2)_n$-heterocyclyl, —$(CH_2)_n$-aryl and —$(CH_2)_n$-heteroaryl are optionally substituted with one to four groups independently selected from $C_{1-3}$alkyl, halogen, $C_{1-3}$alkoxy, —$CF_3$, —OH, oxo, —$(CH_2)_{1-3}O(CH_2)_{2-3}OH$, and —$SO_2CH_3$;
$R^7$ is selected from H, —$CH_3$, —$CH_2CH_3$, —$CF_3$, F, and —CN;
n is 0, 1 or 2;
or a pharmaceutically acceptable salt thereof.

2. The method of claim 1, wherein the patient has clinically significant portal hypertension in compensated cirrhosis.

3. The method of claim 2, wherein the compensated cirrhosis is due to or caused by Hepatitis B Virus (HBV), Hepatitis C Virus (HCV), or Non-Alcoholic Steatohepatitis (NASH).

4. The method of claim 3, wherein the compensated cirrhosis is due to or caused by HBV.

5. The method of claim 3, wherein the compensated cirrhosis is due to or caused by HCV.

6. The method of claim 3, wherein the compensated cirrhosis is due to or caused by NASH.

7. The method of claim 6, wherein the patient has type 2 diabetes mellitus.

8. The method according to claim 1, further comprising administering a pharmaceutically effective amount of a SGLT2 inhibitor to the patient, or a pharmaceutically acceptable salt thereof.

9. The method according to claim 8, wherein the SGLT2 inhibitor is selected from the group consisting of empagliflozin, dapagliflozin and canagliflozin.

10. The method according to claim 9, wherein the SGLT2 inhibitor is empagliflozin.

11. The method according to claim 8, wherein the SGLT2 inhibitor is administered to the patient twice daily.

12. The method according to claim 8, wherein the SGLT2 inhibitor is administered to the patient once daily.

13. The method according to claim 1, wherein the compound of formula (I) is selected from the group consisting of compound number 18, 27, 84, 114, 133, 134, 136, 148, 154, 165, and 167:

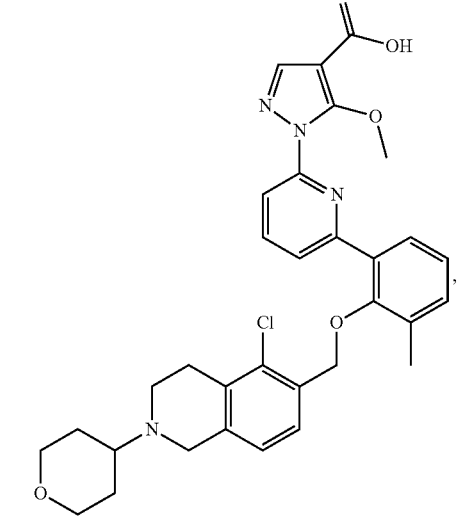

18

27
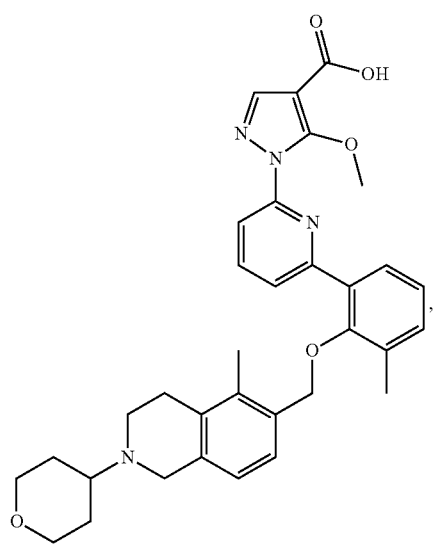
84
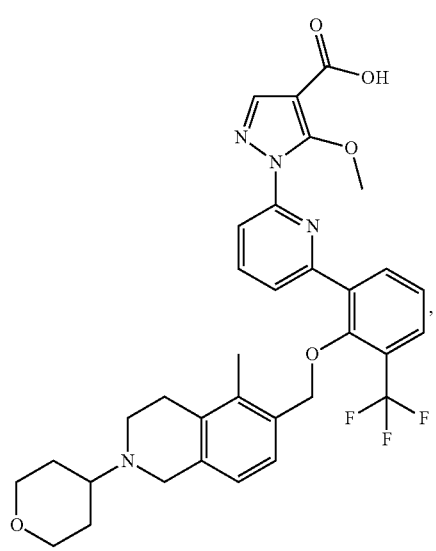
114
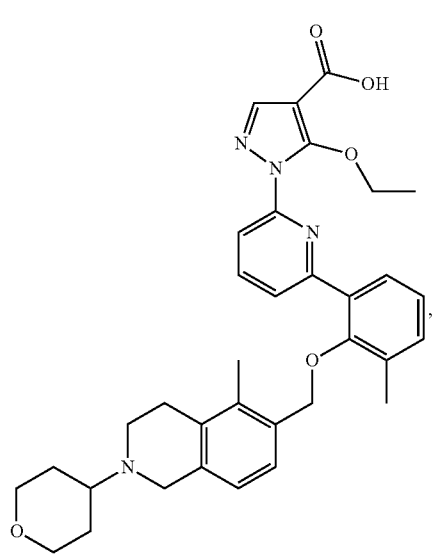
133
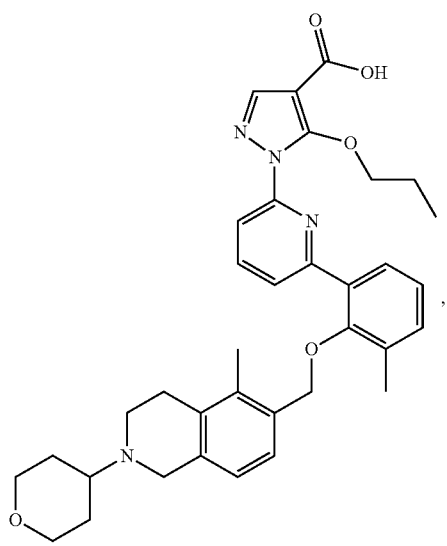
134
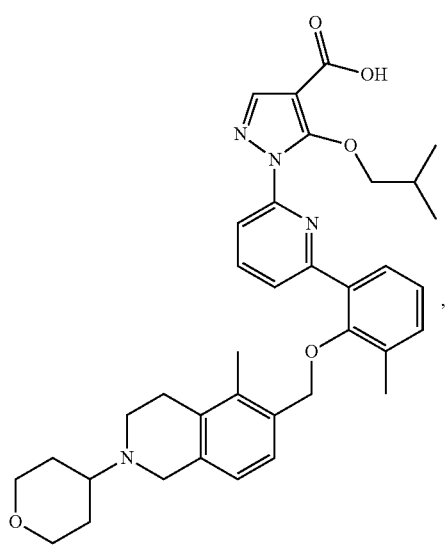
136
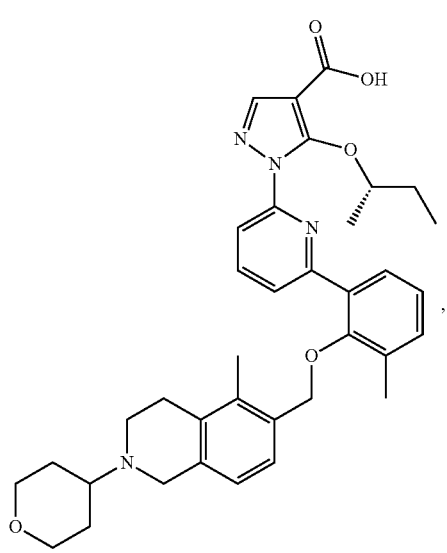

125
-continued
148
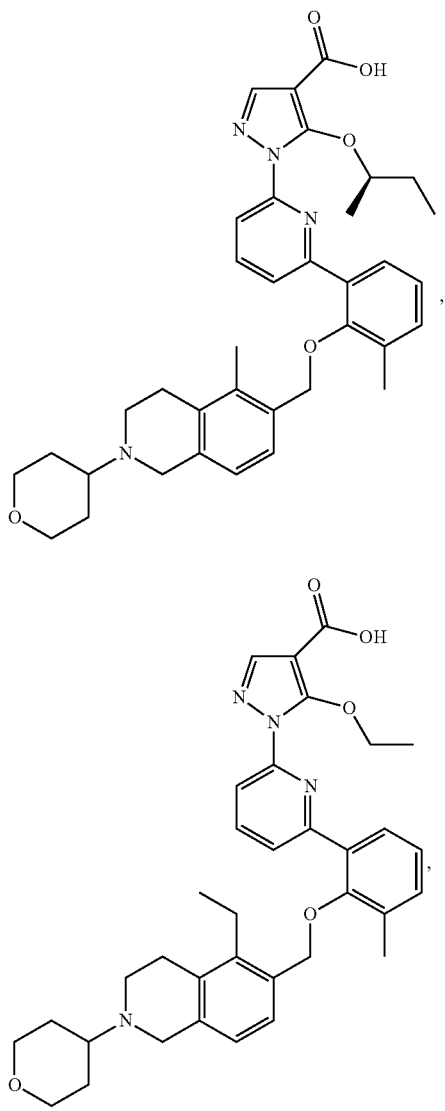
154
126
-continued
165
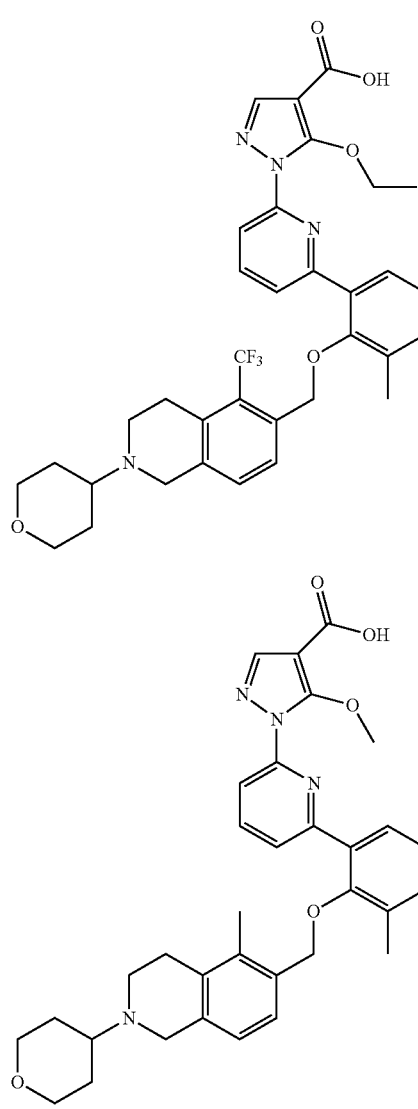
and
167
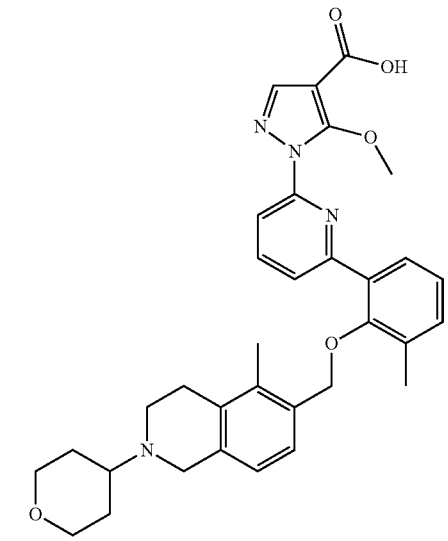
or a pharmaceutically acceptable salt thereof.
* * * * *